US008865442B2

(12) United States Patent
Chotani et al.

(10) Patent No.: US 8,865,442 B2
(45) Date of Patent: Oct. 21, 2014

(54) PRODUCTION OF ISOPRENE UNDER REDUCED OXYGEN INLET LEVELS

(71) Applicants: Danisco US Inc., Palo Alto, CA (US); The Goodyear Tire & Rubber Company, Akron, OH (US)

(72) Inventors: Gopal K. Chotani, Cupertino, CA (US); Brian Kirshner, Foster City, CA (US); Jacob Latone, San Jose, CA (US); Jeff P. Pucci, Pacifica, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 13/725,949

(22) Filed: Dec. 21, 2012

(65) Prior Publication Data

US 2013/0164809 A1   Jun. 27, 2013

Related U.S. Application Data

(60) Provisional application No. 61/580,177, filed on Dec. 23, 2011.

(51) Int. Cl.
*C12N 9/88* (2006.01)
*C12P 5/00* (2006.01)

(52) U.S. Cl.
CPC .. *C12P 5/007* (2013.01); *C12N 9/88* (2013.01)
USPC ......................... 435/170; 435/167; 435/257.2

(58) Field of Classification Search
CPC ...... C12N 9/1022; C12N 9/1205; C12N 9/88; C12N 9/90
USPC ................................ 435/167, 40.5
See application file for complete search history.

(56) References Cited

U.S. PATENT DOCUMENTS

| | | | |
|---|---|---|---|
| 7,659,097 B2 | 2/2010 | Renninger et al. | |
| 7,785,858 B2 | 8/2010 | Kozlov et al. | |
| 8,288,148 B2 * | 10/2012 | Cervin et al. | 435/252.33 |
| 8,420,360 B2 * | 4/2013 | Calabria et al. | 435/167 |
| 2005/0287655 A1 | 12/2005 | Tabata et al. | |
| 2008/0038805 A1 | 2/2008 | Melis | |
| 2009/0203102 A1 | 8/2009 | Cervin et al. | |
| 2009/0282545 A1 | 11/2009 | Eichelberger et al. | |
| 2010/0003716 A1 | 1/2010 | Cervin et al. | |
| 2010/0048964 A1 | 2/2010 | Calabria et al. | |
| 2010/0086978 A1 | 4/2010 | Beck et al. | |
| 2010/0196977 A1 | 8/2010 | Chotani et al. | |
| 2010/0285549 A1 | 11/2010 | Muramatsu et al. | |
| 2010/0297749 A1 | 11/2010 | Aravanis et al. | |
| 2011/0045563 A1 | 2/2011 | Melis | |

FOREIGN PATENT DOCUMENTS

| | | |
|---|---|---|
| JP | 2008/61506 A | 3/2008 |
| WO | WO-98/02550 A2 | 1/1998 |
| WO | WO-98/02550 A3 | 1/1998 |
| WO | WO-2004/033646 A2 | 4/2004 |
| WO | WO-2004/033646 A3 | 4/2004 |
| WO | WO-2008/003078 A2 | 1/2008 |
| WO | WO-2008/003078 A3 | 1/2008 |
| WO | WO-2008/003078 A8 | 1/2008 |
| WO | WO-2009/076676 A2 | 6/2009 |
| WO | WO-2009/076676 A3 | 6/2009 |
| WO | WO-2009/132220 A2 | 10/2009 |
| WO | WO-2009/132220 A3 | 10/2009 |
| WO | WO-2009/132220 A9 | 10/2009 |
| WO | WO-2010/003007 A2 | 1/2010 |
| WO | WO-2010/003007 A3 | 1/2010 |
| WO | WO-2010/013077 A1 | 2/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |
| WO | WO-2010/127290 A2 | 11/2010 |
| WO | WO-2010/127290 A3 | 11/2010 |
| WO | WO-2010/148150 A1 | 12/2010 |
| WO | WO-2010/148256 A1 | 12/2010 |
| WO | WO-2011/034863 A1 | 3/2011 |
| WO | WO-2011/159853 A1 | 12/2011 |

OTHER PUBLICATIONS

Ladygina et al., A review on microbial synthesis of hydrocarbons. Process Biochemistry. 41, 1001-1014, 2006.*
Sasaki et al., Gene expression and characterization of isoprene synthase from *Populus alba*. FEBS Letters. 579: 2514-2518, 2005.*
Bentley et al., Diffusion-Based Process for Carbon Dioxide Uptake and Isoprene Emission in Gaseous/Aqueous Two-Phase Photobioreactors by Photosynthetic Microorganisms. Biotechnology and Bioengineering, vol. 109, No. 1, 100-109, 2012, published on line Aug. 9, 2011.*
Xue et al., Enhancing Isoprene Production by Genetic Modification of the 1-Deoxy-d-Xylulose-5-Phosphate Pathway in *Bacillus subtilis*. App. Environ. Microbiol. 77 (7): 2399-2405. Apr. 2011.*
Whited et al., Development of a gas-phase bioprocess for isoprene-monomer production using metabolic pathway engineering. Industrial Biotechnology. 6 (3): 152-163. Jun. 2010.*
Rasulov et al., Evidence That Light, Carbon Dioxide, and Oxygen Dependencies of Leaf Isoprene Emission Are Driven by Energy Status in Hybrid Aspen. Plant Physiology. 151: 448-460. 2009.*
Andersen, et al., "New Unstable Variants of Green Fluorescent Protein for Studies of Transient Gene Expression in Bacteria," *Appl Environ Microbiol.*, 1998, 64(6), 2240-2246.
Baba, T. et al. (2006). "Construction of *Escherichia coli* K-12 In-Frame, Single-Gene Knockout Mutants: The Keio Collection," *Mol. Syst. Biol.*, 2006.0008, pp. 1-11.
Becker, D. M., et al., "High-Efficiency Transformation of Yeast by Electroporation," *Methods. Enzymol.*, 1991, 194:182-187.
Bentley, F.K. et al. (Jan. 2012, e-pub. Aug. 9, 2011). "Diffusion-Based Process for Carbon Dioxide Uptake and Isoprene Emission in Gaseous/Aqueous Two-Phase Photobioreactors by Photosynthetic Microorganisms," *Biotechnology and Bioengineering* 109:100-109.

(Continued)

*Primary Examiner* — Tekchand Saidha
*Assistant Examiner* — Rama P Ramanujam
(74) *Attorney, Agent, or Firm* — Morrison & Foerster LLP

(57) ABSTRACT

This invention relates to methods for producing isoprene by culturing recombinant cells (e.g., cells engineered to produce isoprene) under reduced oxygen inlet levels.

23 Claims, 23 Drawing Sheets

(56) References Cited

OTHER PUBLICATIONS

Berka, R.M. (1989). "The Development of Gene Expression Systems for Filamentous Fungi," *Biotechnology Advances* 7(2):127-154.
Bhayana, et al., "Amino Acid Sequence of *Escherichia coli* Citrate Synthase," *Biochemistry*, 1984, 23:2900-2905 (Figure 5).
Bologna, et al., "*Escherichia coli* Malic Enzymes: Two Isoforms with Substantial Differences in Kinetic Properties, Metabolic Regulation, and Structure," *Journal of Bacteriology*, 2007, 189:5937-5946.
Bunch, et al., "The IdhA Gene Encoding the Fermentative Lactate Dehydrogenase of *Escherichia coli*," *Microbiology*, 1997, 143:187-195.
Campbell, et al., "Improved Transformation Efficiency of *Aspergillus niger* Using the Homologous niaD Gene for Nitrate Reductase," *Current Genetics*, 1989, 16:53-56.
Chan, E. et al., "Antisense mRNA Method as an Alternative to Generate a Catalase Double Knockout Phenotype in a *Escherichia coli* katG Mutant," *J. Exp. Microbiol. Immunol.*, 2010, 14:127-134.
Cohen, S.N. et al. (Aug. 1972). "Nonchromosomal Antibiotic Resistance in Bacteria: Genetic Transformation of *Escherichia coli* by R-Factor DNA," *Proc. Natl. Acad. Sci. USA*, 69:2110-2114.
Dawes, et al., "The Route to Ethanol Formation in *Zymomonas mobilis*," *Biochem. J.*, 1966, 98:795-803.
Duckworth, et al., "Structural Basis for Regulation in Gram-Negative Bacterial Citrate Synthases," *Biochem. Soc. Symp.* 1987, 54:83-92.
Egan, et al., "Molecular Characterization of the Entner-Doudoroff Pathway in *Escherichia coli*: Sequence Analysis and Localization of Promoters for the edd-eda Operon," *J. Bact.*, 1992, 174(14):4638-4646.
Fernandez, et al., "Farnesyl Diphosphate Synthase. Altering the Catalytic Site to Select for Geranyl Diphosphate Activity," *Biochemistry*, 2000, 39(50):15316-15321.
Fowler, Z.L. et. al. (2009). "Increased Malonyl Coenzyme A Biosynthesis by Tuning the *Escherichia coli* Metabolic Network and Its Application to Flavanone Production," *Applied and Environmental Microbiology* 75(18):5831-5839.
Fujisaki, S. et al. (2005). "Disruption of the Structural Gene for Farnesyl Diphosphate Synthase in *Escherichia coli*," *J. Biochem.* 137(3):395-400.
Genbank Accession No. AB266390, "*Eucalyptus globulus* mts-1 mRNA for monoterpene synthase, complete cds," located at: http://www.ncbi.nlm.nih.gov/nuccore/AB266390, Aug. 11, 2006, 2 pages.
Genbank AB540131.1, "*Streptomyces* sp. CL190 nphT7 gene for acetyl-CoA:malonyl-CoA acyltransferase, complete cds," located at: http://www.ncbi.nlm.nih.gov/nuccore/AB540131.1, Oct. 9, 2013, 2 pages.
GenBank Accession No. AJ457070, "*Cinnamomum tenuipilum* mRNA for geraniol synthase (GerS gene)," located at: http://www.ncbi.nlm.nih.gov/nuccore/AJ457070, Apr. 15, 2005, 2 pages.
GenBank Accession No. AY182241, "*Malus×domestica* (E,E)-alpha-farnesene synthase (AFS1) mRNA, complete cds," located at: http://www.ncbi.nlm.nih.gov/nuccore/AY182241, May 4, 2004, 2 pages.
GenBank Accession No. AY279379, "*Melaleuca alternifolia* putative monoterpene synthase mRNA, complete cds," located at: http://www.ncbi.nlm.nih.gov/nuccore/AY279379, Mar. 11, 2005, 2 pages.
GenBank Accession No. AY316691, "*Pueraria montana* var. lobata isoprene synthase (IspS) gene, complete cds," located at: http://www.ncbi.nlm.nih.gov/nuccore/AY316691, Feb. 15, 2005, 2 pages.
GenBank Accession No. AY341431, *Melaleuca alternifolia* putative monoterpene synthase mRNA, complete cds, located at http://www.ncbi.nlm.nih.gov/nuccore/AY279379, Feb. 15, 2005, 2 pages.
Genbank Accession No. JN173037, "*Populus balsamifera* isoprene synthase mRNA, complete cds," located at: http://www.ncbi.nlm.nih.gov/nuccore/JN173037, Apr. 15, 2013, 2 pages.
Genbank Accession No. JN173038, "*Populus grandidentata* isoprene synthase mRNA, complete cds," located at: http://www.ncbi.nlm.nih.gov/nuccore/JN173038, Apr. 15, 2013, 2 pages.
Genbank Accession No. JN173039, "*Populus deltoides* isoprene synthase mRNA, complete cds," located at: http://www.ncbi.nlm.nih.gov/nuccore/JN173039, Apr. 15, 2013, 2 pages.
Genbank Accession No. JN173040, *Populus fremontii* isoprene synthase mRNA, complete cds, located at: http://www.ncbi.nlm.nih.gov/nuccore/JN173040, Apr. 15, 2013, 2 pages.
Genbank Accession No. JN173041, "*Robinia pseudoacacia* isoprene synthase mRNA, partial cds," located at: http://www.ncbi.nlm.nih.gov/nuccore/JN173041, Apr. 15, 2013, 2 pages.
Genbank Accession No. JN173042, "*Wisteria* sp. 101210T2Dc1 isoprene synthase mRNA, partial cds," located at: http://www.ncbi.nlm.nih.gov/nuccore/JN173042, Apr. 15, 2013, 2 pages.
Genbank Accession No. JN173043, *Salix* sp. DG-2011 isoprene synthase mRNA, partial cds, located at: http://www.ncbi.nlm.nih.gov/nuccore/JN173043, Apr. 15, 2013, 2 pages.
GenBank NC_001416 (SEQ ID No. 10), "Enterobacteria phage lambda, complete genome," located at: http://www.ncbi.nlm.nih.gov/nuccore/NC_001416, Mar. 11, 2011, 42 pages.
Hedl, et al. "*Enterococcus faecalis* Acetoacetyl-Coenzyme A Thiolase/3-Hydroxy-3-Methyglutaryl-Coenzyme A Reductase, a Dual-Function Protein of Isopentenyl Diphosphate Biosynthesis," *Journal of Bacteriology*, Apr. 2002, 184(8):2116-2122.
Hinnen, A. et al., "Transformation of Yeast," *Proc. Natl. Acad. Sci. USA*, 1978, 75:1929-1933.
Ito, H. et al. (Jan. 1983). "Transformation of Intact Yeast Cells Treated with Alkali Cations," *J. Bacteriol.* 153:163-168.
Iwakura, M. et al. (1979). "Studies on Regulatory Functions of Malic Enzymes," *J. Biochem.* 85:1355-1365.
Kakuda, et al., "Identification and Characterization of the ackA (Acetate Kinase A)-pta (Phosphotransacetylase) Operon and Complementation Analysis of Acetate Utilization by an ackA-pta Deletion Mutant of *Escherichia coli*," *J. Biochem.*, 1994, 116:916-922.
Kim, J.Y.H. et al. (Sep. 30, 2003, e-pub. Jun. 23, 2003). "Down-Regulation of Acetate Pathway Through Antisense Strategy in *Escherichia coli*: Improved Foreign Protein Production," *Biotechnology and Bioengineering* 83(7):841-853.
Kotlarz, et al., "Regulation of the Amount and of the Activity of Phosphofructokinases and Pyruvate Kinases in *Escherichia coli*," *Biochim. Biophys. Acta*, 1975, 381:257-268.
Koyama, et al., "Thermostable Farnesyl Diphosphate Synthase of *Bacillus stearothermophilus*: Molecular Cloning, Sequence Determination, Overproduction, and Purification," *J. Biochem.*, 1993, 113:355-363.
Lindberg, et al., "Engineering a Platform for Photosynthetic Isoprene Production in Cyanobacteria, Using *Synechocystis* as the Model Organism," *Metab. Eng.*, 2010, 12(1):70-79.
Maurus, et al., "Insights into the Evolution of Allosteric Properties. The NADH Binding Site of Hexameric Type II Citrate Synthases," *Biochemistry*, 2003, 42:5555-5565.
Meile, et al., "Characterization of the D-Xylulose 5-Phosphate/D-Fructose 6-Phosphate Phosphoketolase Gene (xfp) from *Bifidobacterium lactis*," *J. Bact.*, 2001, 183:2929-2936.
Miller, B. et al. (2001, e-pub. May 10, 2001). "First Isolation of an Isoprene Synthase Gene from Poplar and Successful Expression of the Gene in *Escherichia coli*," *Planta* 213:483-487.
Nakashima, N. et al. (2006, e-pub. Oct. 24, 2006). "Paired Termini Stabilize Antisense RNAs and Enhance Conditional Gene Silencing in *Escherichia coli*," *Nucleic Acids Res.* 34(20): e138, 8 pages.
Ner, et al., "Complete Sequence of the glt A Gene Encoding Citrate Synthase in *Escherichia coli*," *Biochemistry*, 1983, 22:5243-5249.
Nichols, D.S. et al. (2004). "Cold Adaptation in the Antarctic Archaeon *Methanococcoides burtonii* Involves Membrane Lipid Unsaturation," *J. Bacteriol.* 186(24):8508-8515.
Ogasawara, H. et al. (2007). "PdhR (Pyruvate Dehydrogenase Complex Regulator) Controls the Respiratory Electron Transport System in *Escherichia coli*," *J. Bact.* 189:5534-5541.
Oh, M.-K. et al. (Apr. 12, 2002). "Global Expression Profiling of Acetate-Grown *Escherichia coli*," *The Journal of Biological Chemistry* 277(15):13175-13183.
Okamura, et al. (Jun. 22, 2010). "Unprecedented Acetoacetyl-coenzyme A Synthesizing Enzyme of the Thiolase Superfamily Involved in the Mevalonate Pathway," *PNAS* 107(25):11265-11270.
Peekhaus, N. et al. (Jul. 1998). "What's for Dinner?: Entner-Doudoroff Metabolism in *Escherichia coli*," *Journal of Bacteriology* 180(14):3495-3502.

(56) References Cited

OTHER PUBLICATIONS

Quant, P.A. et al. (1989). "Treatment of Rats With Glucagon or Mannoheptulose Increases Mitochondrial 3-Hydroxy-3-Methylglutaryl-CoA Synthase Activity and Decreases Succinyl-CoA Content in Liver," *Biochem. J.* 262:159-164.

Ranzer, L.K. et al. (2009). "A New Prokaryotic Farnesyldiphosphate Synthase from the Octocoral *Eunicea fusca:* Differential Display, Inverse PCR, Cloning, and Characterization," *Mar. Biotechnol.* 11:62-73.

Roberts, R.C. et al. (Apr. 1996). "Identification of a *Caulobacter crescentus* Operon Encoding hrcA, Involved in Negatively Regulating Heat-Inducible Transcription, and the Chaperone Gene grpE," *Journal of Bacteriology* 178(7):1829-1841.

Romanos, et al., "Foreign Gene Expression in Yeast: a Review," *Yeast*, 1992, 8(6):423-488.

Sanchez, et al., "Novel Pathway Engineering Design of the Anaerobic Central Metabolic Pathway in *Escherichia coli* to Increase Succinate Yield and Productivity," *Metab. Eng.*, 2005, 7:229-239.

Shao, Y. et al. (2006, e-pub. Oct. 11, 2006). "Rapid Design and Rapid Screening of Antisense Oligonucleotides for Prokaryotic Gene Modulation," *Nucleic Acids Research* 34(19):5660-5669.

Sharkey, T.D. et al. (2012). "Isoprene Synthase Genes Form a Monophyletic Clade of Acyclic Terpene Synthases in the TPS-B Terpene Synthase Family", *Evolution* pp. 1-15.

Sharkey, T.D. et al. (Feb. 2005). "Evolution of the Isoprene Biosynthetic Pathway in Kudzu," *Plant Physiology* 137:700-712.

Shimizu, et al., "Phosphotransacetylase of *Escherichia coli* B, Purification and Properties," *Biochimica et Biophysica Acta*, 1969, 191:550-558.

Silver, et al., "Characterization of Aspen Isoprene Synthase, an Enzyme Responsible for Leaf Isoprene Emission to the Atmosphere," *J. Biol. Chem.*, 1995, 270(22):13010-13016.

Song, S. et al. (Nov. 1997). "Organization and Regulation of the D-xylose Operons in *Escherichia coli* K-12: XylR Acts as a Transcriptional Activator," *Journal of Bacteriology* 179(22):7025-7032.

Sprenger, G.A. (1995). "*Escherichia coli* K-12," *Arch. Microbiol.* 164:324-330.

Stokell, D.J. et al. (Sep. 12, 2003). "Probing the Roles of Key Residues in the Unique Regulatory NADH Binding Site of Type II Citrate Synthase of *Escherichia coli*," *The Journal of Biological Chemistry* 278(37):35435-35443.

Stülke, J. et al. (2000). "Regulation of Carbon Catabolism in *Bacillus* Species," *Annu. Rev. Microbiol.* 54:849-880.

Susin, M.F. et al. (Oct. 2004). "Functional and Structural Analysis of HrcA Repressor Protein from *Caulobacter crescentus*," *Journal of Bacteriology* 186(20):6759-6767.

Tabata, K. et al. (2004). "Production of Mevalonate by a Metabolically-Engineered *Escherichia coli*," *Biotechnology Letters* 26:1487-1491.

Underwood, S.A. et al. (2002). "Flux Through Citrate Synthase Limits the Growth of Ethanologenic *Escherichia coli* KO11 During Xylose Fermentation," *Applied and Environmental Microbiology* 68(3):1071-1081.

Wiegand, G. et al. (1986). "Citrate Synthase: Structure, Control, and Mechanism," *Ann. Rev. Biophys. Biophys. Chem.* 15:97-117.

Wolfe, A.J. (2005). "The Acetate Switch," *Microbiol. Mol. Biol. Rev.* 69:12-50.

International Search Report mailed on May 17, 2013, for PCT Patent Application No. PCT/US2012/071505, filed on Dec. 21, 2012, five pages.

\* cited by examiner

US 8,865,442 B2

PRODUCTION OF ISOPRENE UNDER REDUCED OXYGEN INLET LEVELS

CROSS-REFERENCE TO RELATED APPLICATIONS

This application claims priority to U.S. Provisional Patent Application No. 61/580,177, filed Dec. 23, 2011, the disclosure of which is incorporated by reference herein in its entirety.

INCORPORATION BY REFERENCE

The Sequence Listing submitted in an ASCII text file, in accordance with 37 C.F.R. §1.821(c) and (e), is incorporated by herein by reference. The text file name is "643842004400.txt", the date of creation of the text file is Dec. 21, 2012, and the size of the ASCII text file in bytes is 24,576.

FIELD OF THE INVENTION

The present invention relates generally to improved methods for producing isoprene by culturing recombinant cells (e.g., cells engineered to produce isoprene) under reduced oxygen inlet levels.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway. However, the yield of isoprene from naturally-occurring organisms is commercially unattractive. Isoprene can also be obtained by fractionating petroleum, the purification of this material is expensive and time-consuming. Petroleum cracking of the C5 stream of hydrocarbons produces only about 15% isoprene. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Recent developments in the production of isoprene disclose methods for the production of isoprene at rates, titers, and purities that can be sufficient to meet the demands of robust commercial processes (see, for example, International Patent Application Publication No. WO 2009/076676 A2); however, alternate pathways to improve production and yields of the same are still needed. Provided herein are methods and system for producing isoprene using recombinant cells engineered to produce isoprene.

Throughout this specification, various patents, patent applications and other types of publications (e.g., journal articles) are referenced. The disclosure of all patents, patent applications, and publications cited herein are hereby incorporated by reference in their entirety for all purposes.

BRIEF SUMMARY OF THE INVENTION

The invention provided herein discloses, inter alia, methods, compositions and systems for improved production of isoprene under reduced oxygen inlet levels. Accordingly, in one aspect, the invention provides for methods for producing isoprene by (a) culturing a recombinant host cell comprising a heterologous nucleic acid encoding isoprene synthase under reduced oxygen inlet levels; and (b) producing isoprene. In another aspect, the invention provides for methods for producing isoprene by (a) culturing a recombinant host cell comprising a heterologous nucleic acid encoding isoprene synthase under reduced oxygen inlet levels wherein the cell is in fermentation or production phase; and (b) producing isoprene. In any of the aspects, the method can include further recovery of the isoprene. In some aspects, the reduced oxygen inlet level is between about 5% to about 15% oxygen. In some aspects, the reduced oxygen inlet level is between about 5% to about 11% oxygen. In some aspects, the reduced oxygen inlet level is between about 7% to about 10% oxygen. In some aspects, the reduced oxygen inlet level is between about 7% to about 10% oxygen. In some aspects, the reduced oxygen inlet level is between about 7% to about 9% oxygen. In some aspects, the reduced oxygen inlet level is about 7.7% oxygen. In some aspects, the reduced oxygen inlet level is about 9.3% oxygen.

In another aspect, the invention provides for methods for producing isoprene by (a) culturing a recombinant host cell comprising a heterologous nucleic acid encoding isoprene synthase under reduced oxygen inlet levels having an inlet airflow rate of between about 8.0 standard liter per minute (SLPM) and about 14 SLPM and (b) producing isoprene. In some aspects, the inlet airflow rate is between about 6 SLPM and 14 SLPM. In some aspects, the inlet airflow rate is between about 8 SLPM and 12 SLPM. In some aspects, the inlet airflow rate is about 10 SLPM. In some aspects, the method further comprises recovering the isoprene.

In some aspects, the isoprene synthase is a plant isoprene synthase. In some aspects, the plant isoprene synthase polypeptide is a poplar isoprene synthase polypeptide. In some aspects, the plant isoprene synthase polypeptide is a kudzu isoprene synthase polypeptide. In some aspects, the plant isoprene synthase polypeptide is a willow isoprene synthase polypeptide. In some aspects, the isoprene synthase is an isoprene synthase from *Pueraria* or *Populus* or a hybrid, *Populus alba*×*Populus tremula*. In some aspects, the isoprene synthase polypeptide is selected from the group consisting of *Pueraria montana* or *Pueraria lobata, Populus tremuloides, Populus alba, Populus nigra,* and *Populus trichocarpa*. In some aspects, the plant isoprene synthase is a poplar synthase, a kudzu isoprene synthase, a willow isoprene synthase, or a eucalyptus isoprene synthase. In some aspects, the isoprene synthase is an isoprene synthase variant.

In some aspects, the cell further comprises a heterologous nucleic acid encoding for one or more MVA pathway polypeptide and/or one or more DXP pathway polypeptide. In some aspects, the cell further comprises a heterologous nucleic acid encoding for one or more MVA pathway polypeptide and/or an endogenous nucleic acid encoding for one or more DXP pathway polypeptide. In some aspects, the cell further comprises a heterologous nucleic acid encoding for one or more IDI polypeptide.

In some aspects, one or more copies of a heterologous nucleic acid is overexpressed. In some aspects, the heterologous nucleic acid is cloned into a multicopy plasmid. In some aspects, the heterologous nucleic acid is placed under an inducible promoter or a constitutive promoter. In some aspects, one or more of the heterologous nucleic acids is integrated into the chromosome of the recombinant host cell.

In some aspects, the recombinant host cell is selected from the group consisting of bacterial, yeast, algal, and fungal cells. In some aspects, the cells are bacterial cells. In some aspects, the bacterial cells are gram-positive bacterial cells or gram-negative bacterial cells. In some aspects, the bacterial cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *P. alcaligenes*, and *Corynebacteria* sp. cells. In some aspects, the bacterial cells are *E. coli*.

In some aspects, the cells are algal cells. In some aspects, the algal cells are selected from the group consisting of green algae, red algae, glaucophytes, chlorarachniophytes, euglenids, chromista, or dinoflagellates.

In some aspects, the cells are fungal cells. In some aspects, the fungal cells are filamentous fungi. In some aspects, the cells are yeast cells. In some aspects, the yeast cells are is selected from the group consisting of *Saccharomyces* sp., *Schizosaccharomyces* sp., *Pichia* sp., or *Candida* sp. In some aspects, the yeast cells are *Saccharomyces cerevisiae*.

In some aspects, the peak instantaneous yield of isoprene is increased at least about 11% as compared to when ambient air is used for inlet gas. In some aspects, the peak cumulative yield of isoprene is increased at least about 8% as compared to when ambient air is used for inlet gas. In some aspects, the CPI is increased at least about 16% as compared to when ambient air is used for inlet gas. In some aspects, the peak specific productivity is increased at least about 26% as compared to when ambient air is used for inlet gas.

In some aspects, the reduced oxygen inlet is used when the cells are in production phase. In other aspects, the reduced oxygen inlet is used when the cells are in growth phase. In other aspects, the reduced oxygen inlet is used when the culture has cells where some cells are in growth phase and other cells are in production phase. In other aspects, the reduced oxygen inlet is used when the culture has cells where the majority of cells are in production phase.

Overall yield was calculated using the following formula:

% wt Yield on glucose=Isoprene total $(t)$/[(Feed Wt(0)−Feed Wt$(t)$+83.5)*0.59)], where 0.59 is the wt % of glucose in the glucose feed solution and 83.5 is the grams of this feed batched into the fermentor at t=0. Each feed had its weight % measured independently.

The run 20100522: CMP561 at 20.9% O2 inlet is depicted by closed black triangles. The run 20100523: CMP561 at 20.9% O2 inlet is depicted by open black triangles. The run 20110940: CMP1043 at 5.0% O2 inlet is depicted by closed black squares. The run 20110909: CMP1043 at 5.0% O2 inlet is depicted by open black squares. The run 20111019: CMP1043 at 7.7% O2 inlet is depicted by closed black diamonds. The run 20111020: CMP1043 at 7.7% O2 inlet is depicted by open black diamonds. The run 20111109: CMP1043 at 9.3% O2 inlet is depicted by closed black circles.

Figure 2:
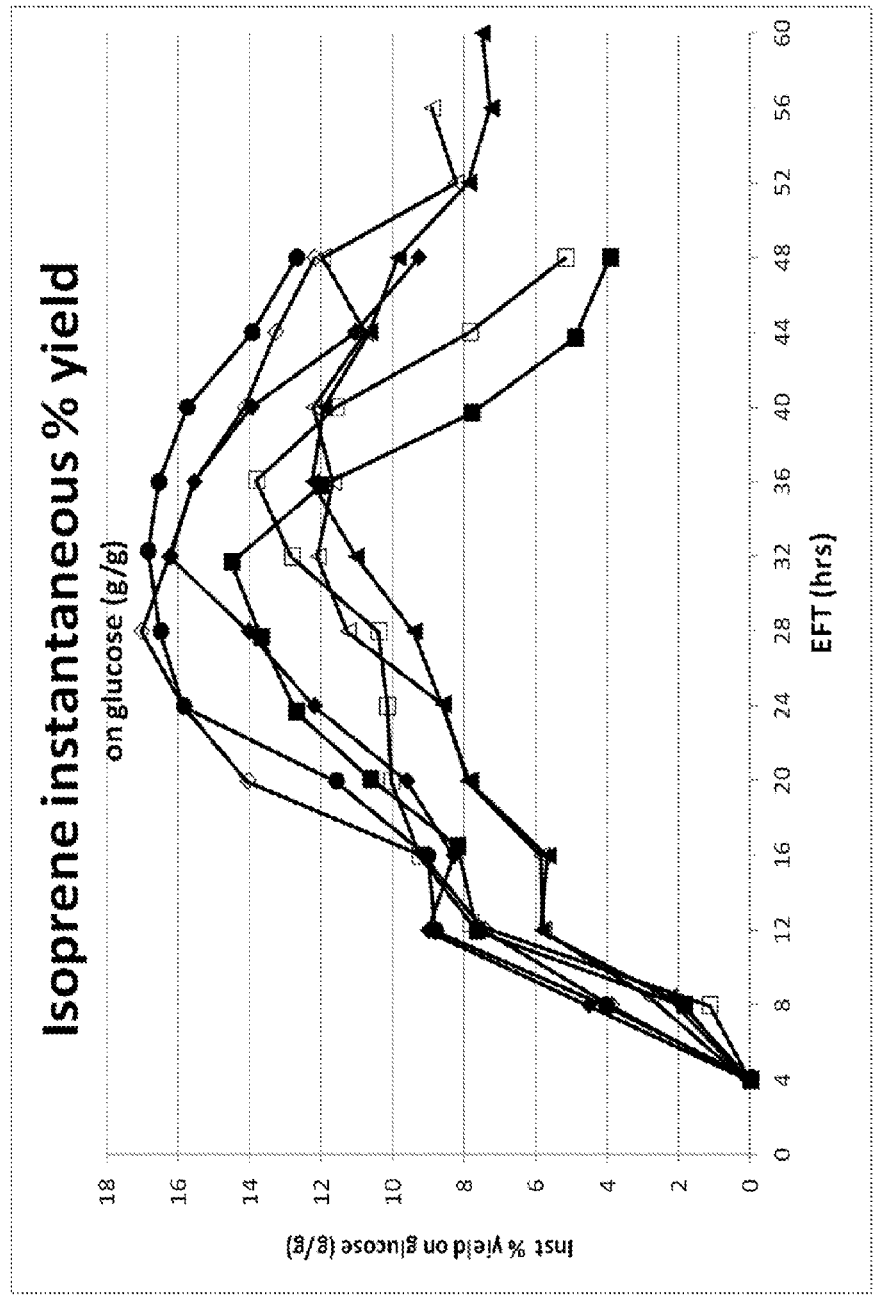

FIG. 2 depicts a graph showing instantaneous yield of isoprene on glucose achieved in each 15-L fermentation over time. All runs used a production host of the same genotype. The oxygen inlet % is listed below for each experiment. All runs using the lower oxygen inlet gas (circles, squares, and diamonds) achieved a higher peak instantaneous % yield of isoprene on glucose than the two runs using standard house air (open and closed triangles).

Isoprene Instantaneous yield was calculated using the following formula:

Isoprene Inst. yield (g/g %)=Isoprene produced $(t_1 − t_0)$/consumed glucose $(t_1−t_0)$*100.

The run 20100522: CMP561 at 20.9% O2 inlet is depicted by closed black triangles. The run 20100523: CMP561 at 20.9% O2 inlet is depicted by open black triangles. The run 20110940: CMP1043 at 5.0% O2 inlet is depicted by closed black squares. The run 20110909: CMP1043 at 5.0% O2 inlet is depicted by open black squares. The run 20111019: CMP1043 at 7.7% O2 inlet is depicted by closed black diamonds. The run 20111020: CMP1043 at 7.7% O2 inlet is depicted by open black diamonds. The run 20111109: CMP1043 at 9.3% O2 inlet is depicted by closed black circles.

Figure 3:
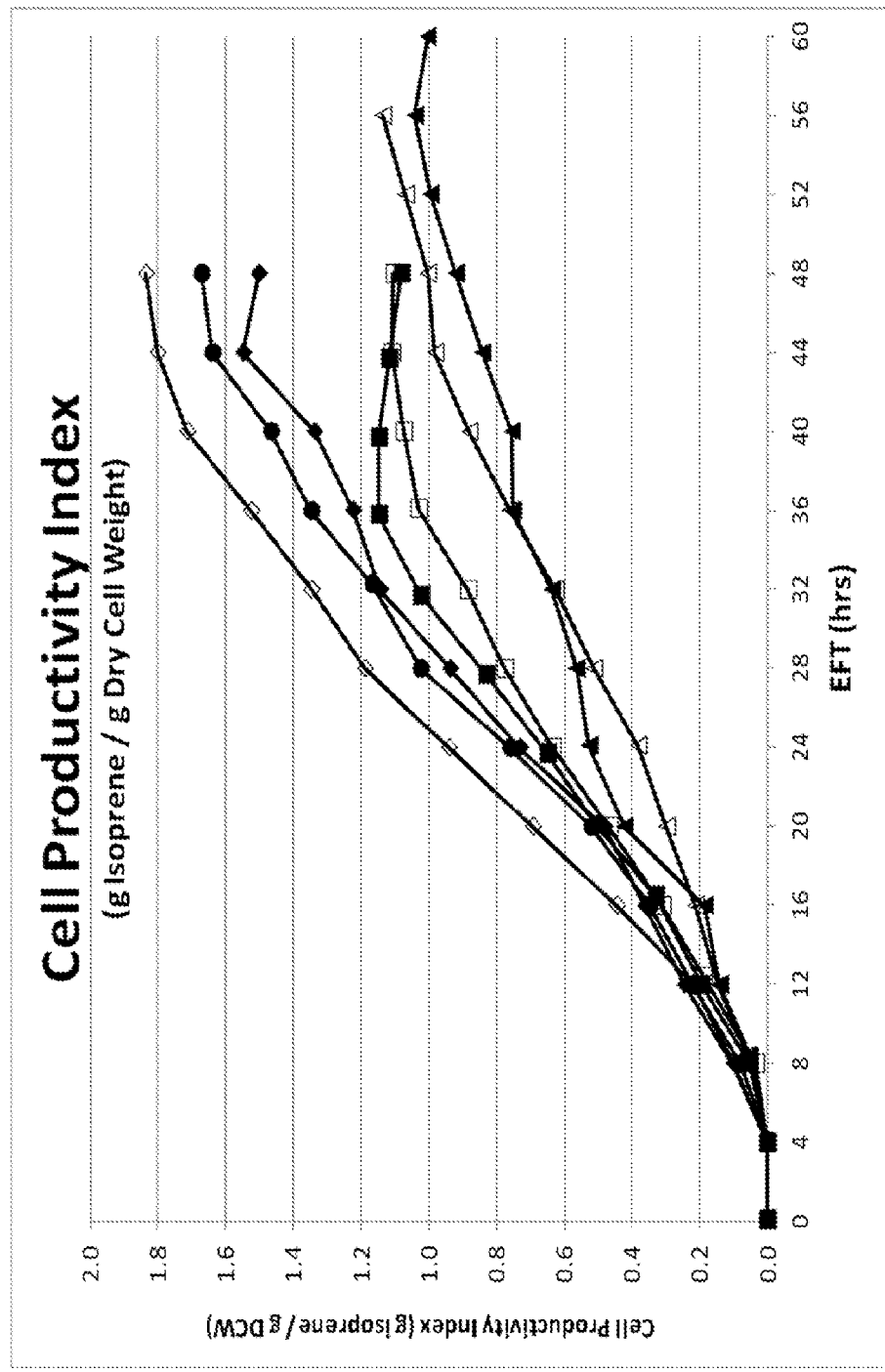

FIG. 3 depicts a graph showing cell productivity index (CPI) achieved in each 15-L fermentation over time. All runs used a production host of the same genotype. The oxygen inlet % is listed for each experiment. All runs using the lower concentration oxygen inlet gas (circles, squares and diamonds) achieved a higher cell productivity index compared to the two runs using standard house air (open and closed triangles).

Cell Productivity Index (CPI) was calculated using the following formula:

CPI=total grams Isoprene/total grams dry cell weight

The run 20100522: CMP561 at 20.9% O2 inlet is depicted by closed black triangles. The run 20100523: CMP561 at 20.9% O2 inlet is depicted by open black triangles. The run 20110940: CMP1043 at 5.0% O2 inlet is depicted by closed black squares. The run 20110909: CMP1043 at 5.0% O2 inlet is depicted by open black squares. The run 20111019: CMP1043 at 7.7% O2 inlet is depicted by closed black diamonds. The run 20111020: CMP1043 at 7.7% O2 inlet is depicted by open black diamonds. The run 20111109: CMP1043 at 9.3% O2 inlet is depicted by closed black circles.

Figure 4:
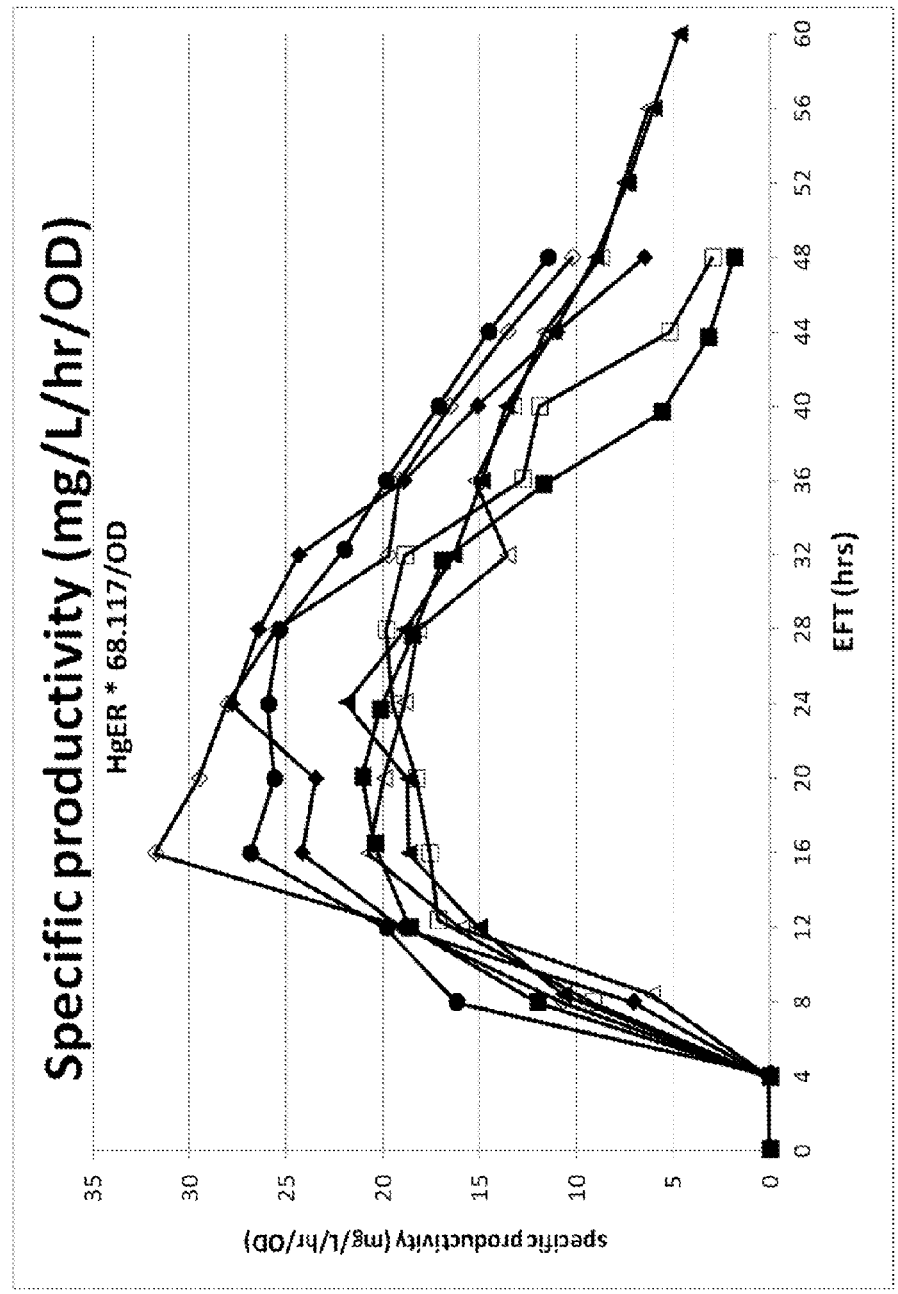

FIG. 4 depicts a graph showing specific productivity achieved in each 15-L fermentation over time. All runs used a production host of the same genotype. The oxygen inlet % is listed for each experiment. While runs using the 5.0% oxygen inlet gas (20110909, 20110940) achieved about the same specific productivity as the two runs using standard house air (20100522, 20100523), the three runs using 7.7%, 7.7% and 9.3% (20111019, 20111020, 20111109, respectively) achieved a significantly higher specific productivity of isoprene.

Specific Productivity was calculated using the following formula:

Specific productivity (mg/L/hr/OD)=HgER*68.117 g/mol/OD.

HgER is the Isoprene Evolution Rate in (mmol/L/hr).

OD=optical density=Absorbance at 550 nm*dilution factor in water

The run 20100522: CMP561 at 20.9% O2 inlet is depicted by closed black triangles. The run 20100523: CMP561 at 20.9% O2 inlet is depicted by open black triangles. The run 20110940: CMP1043 at 5.0% O2 inlet is depicted by closed black squares. The run 20110909: CMP1043 at 5.0% O2 inlet is depicted by open black squares. The run 20111019: CMP1043 at 7.7% O2 inlet is depicted by closed black diamonds. The run 20111020: CMP1043 at 7.7% O2 inlet is depicted by open black diamonds. The run 20111109: CMP1043 at 9.3% O2 inlet is depicted by closed black circles.

Figure 5:
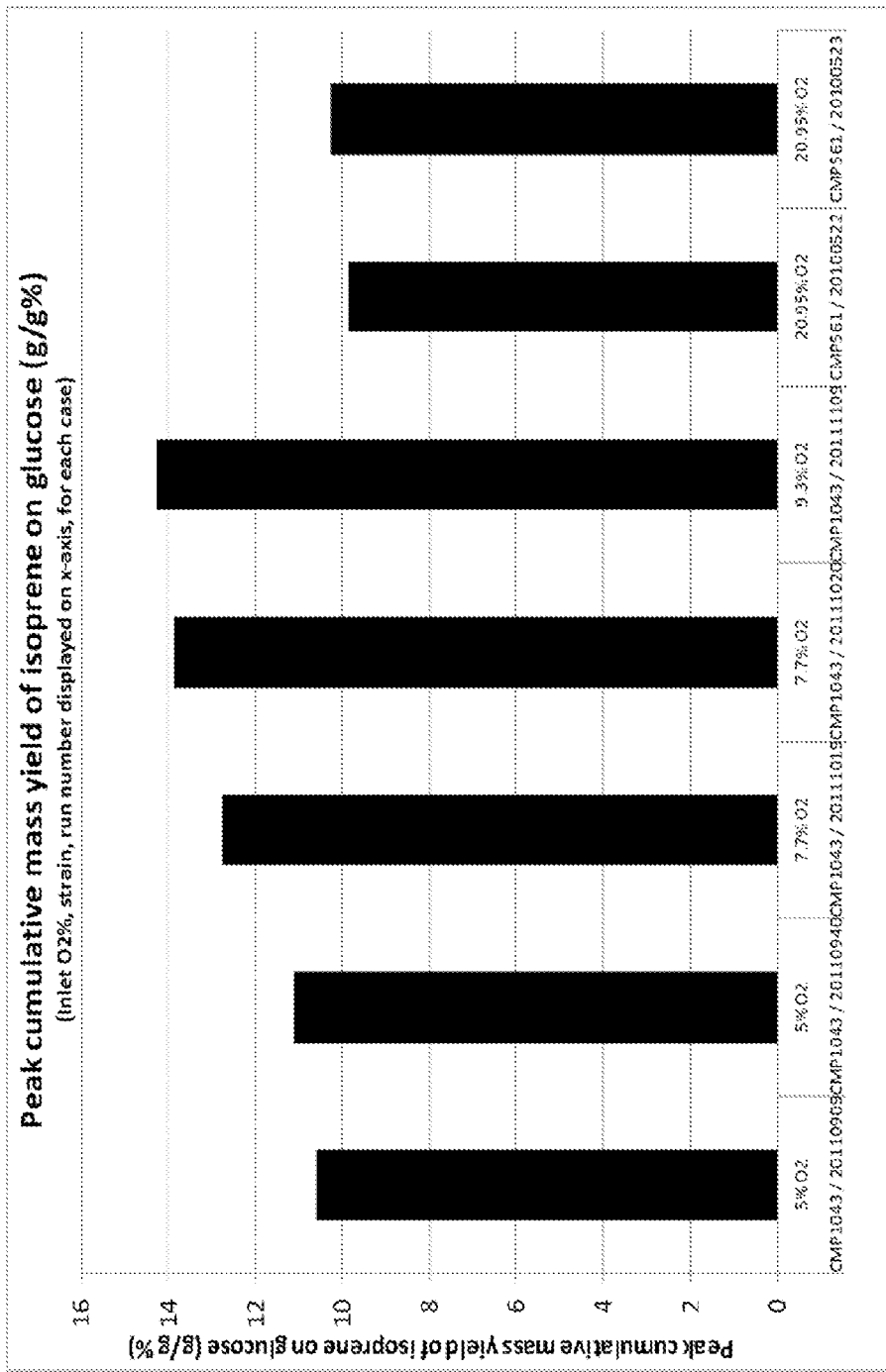

FIG. 5 is a graph where the peak cumulative mass yield data in table 1 is plotted as a bar graph. While runs using the 5.0% oxygen inlet gas (20110909, 20110940) achieved a modestly higher mass yield of isoprene on glucose than the two runs using standard house air (20100522, 20100523), the three runs using 7.7%, 7.7% and 9.3% (20111019, 20111020, 20111109, respectively) achieved a significantly higher mass yield of isoprene on glucose.

Figure 6:
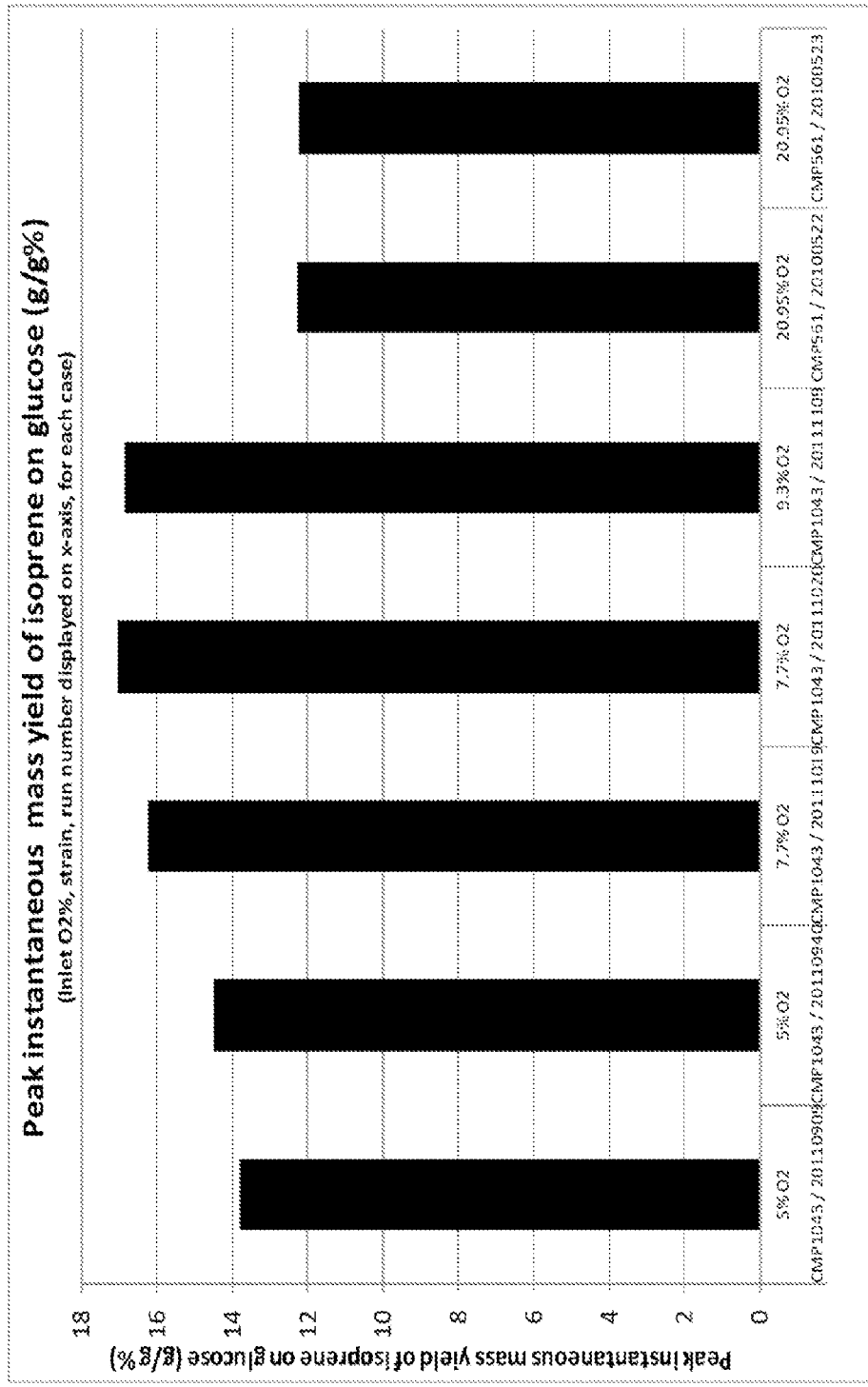

FIG. 6 is a graph where the peak instantaneous yield data in table 1 is plotted as a bar graph. All runs using the lower oxygen inlet gas (20110909, 20110940, 20111019, 20111020, 20111109) achieved a higher instantaneous % yield of isoprene on glucose than the two runs using standard house air (20100522, 20100523).

Figure 7:
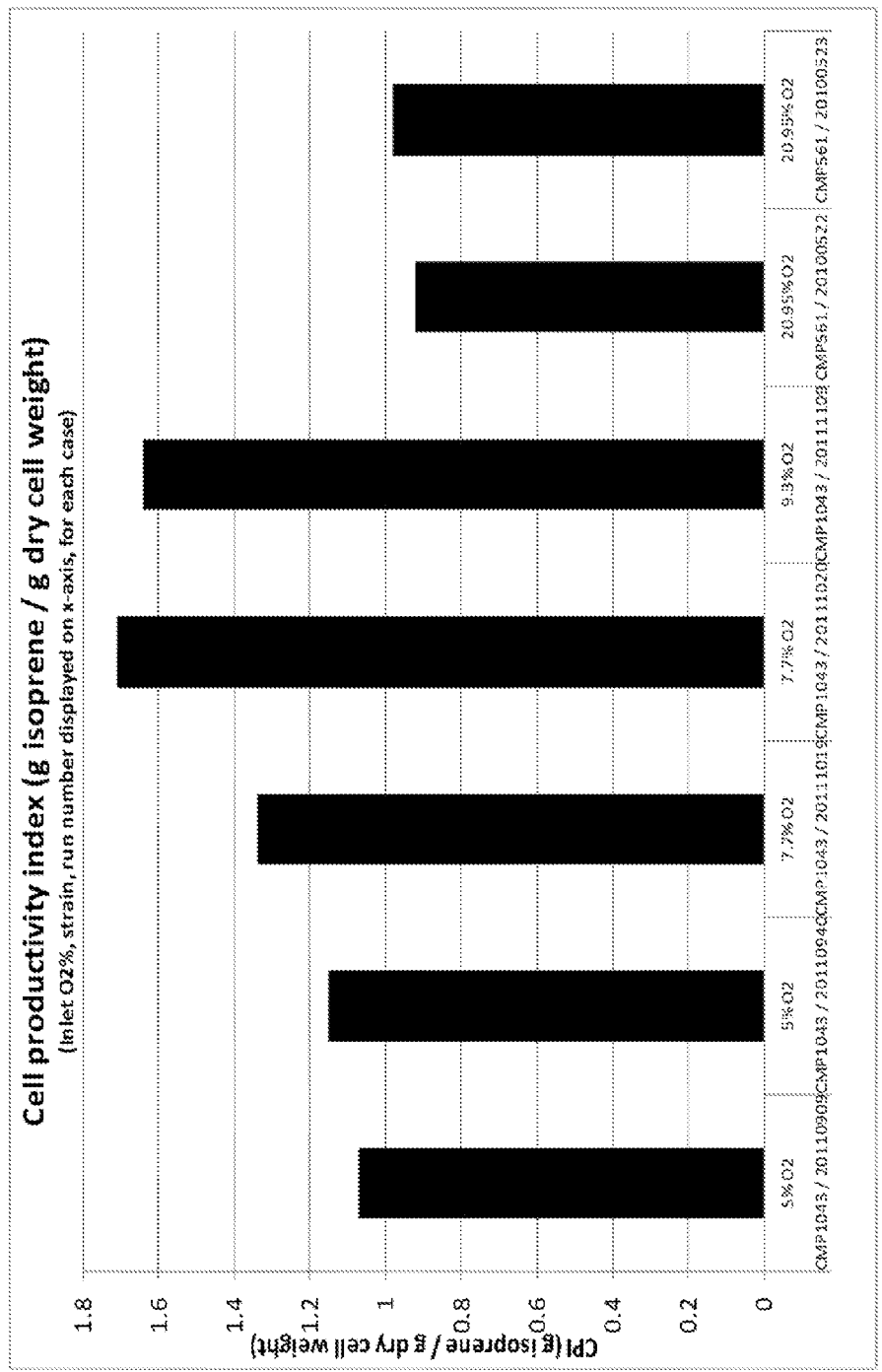

FIG. 7 is a graph where the cell productivity index data in table 1 is plotted as bar graph. All runs using the lower oxygen inlet gas (20110909, 20110940, 20111019, 20111020, 20111109) achieved a higher cell productivity index than the two runs using standard house air (20100522, 20100523).

Figure 8:
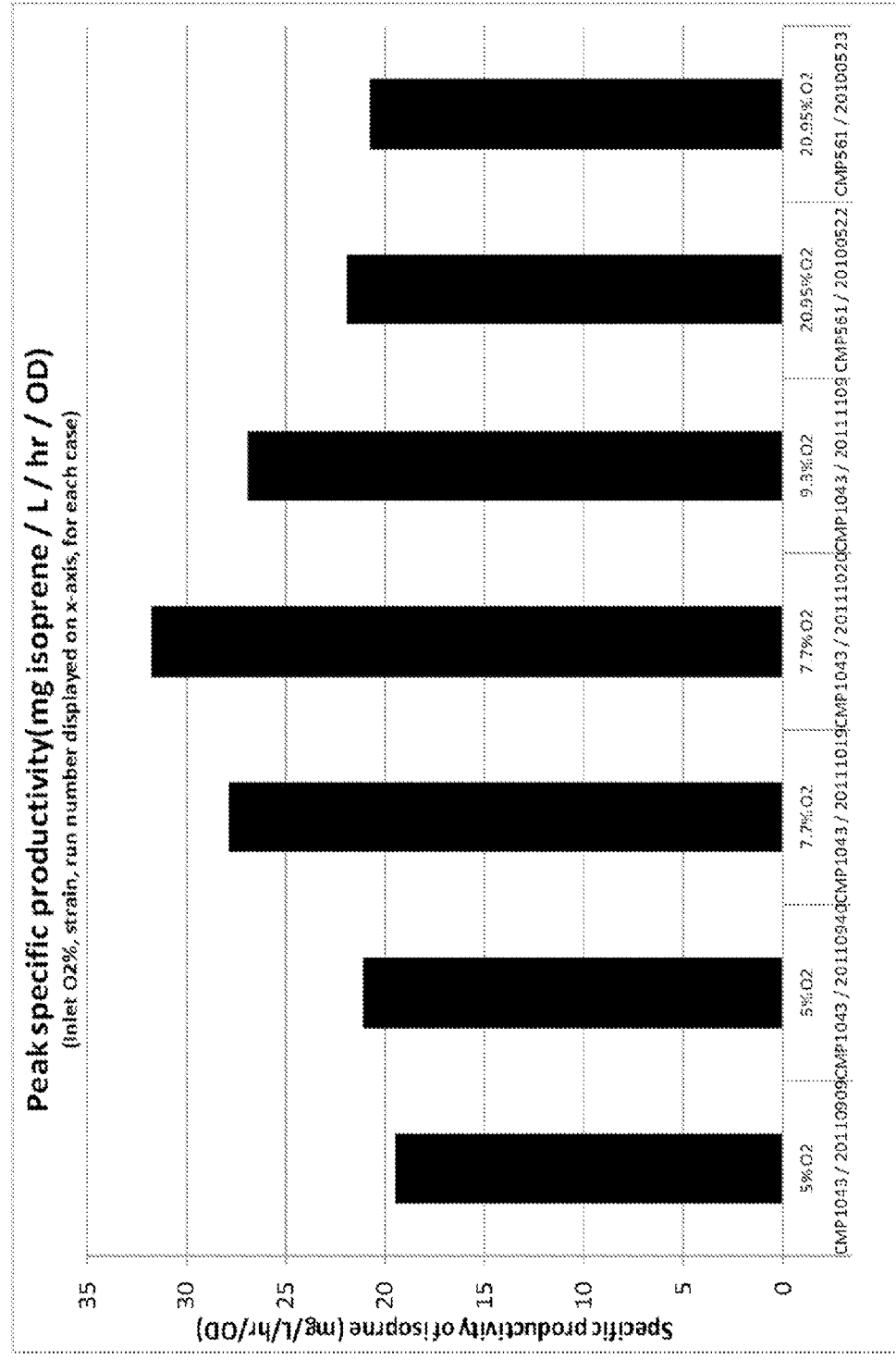

FIG. 8 is a graph where the peak specific productivity data in table 1 is plotted as bar graph. While runs using the 5.0% oxygen inlet gas (20110909, 20110940) achieved about the same specific productivity as the two runs using standard house air (20100522, 20100523), the three runs using 7.7%, 7.7% and 9.3% (20111019, 20111020, 20111109, respectively) achieved a significantly higher peak specific productivity of isoprene.

Figure 9:
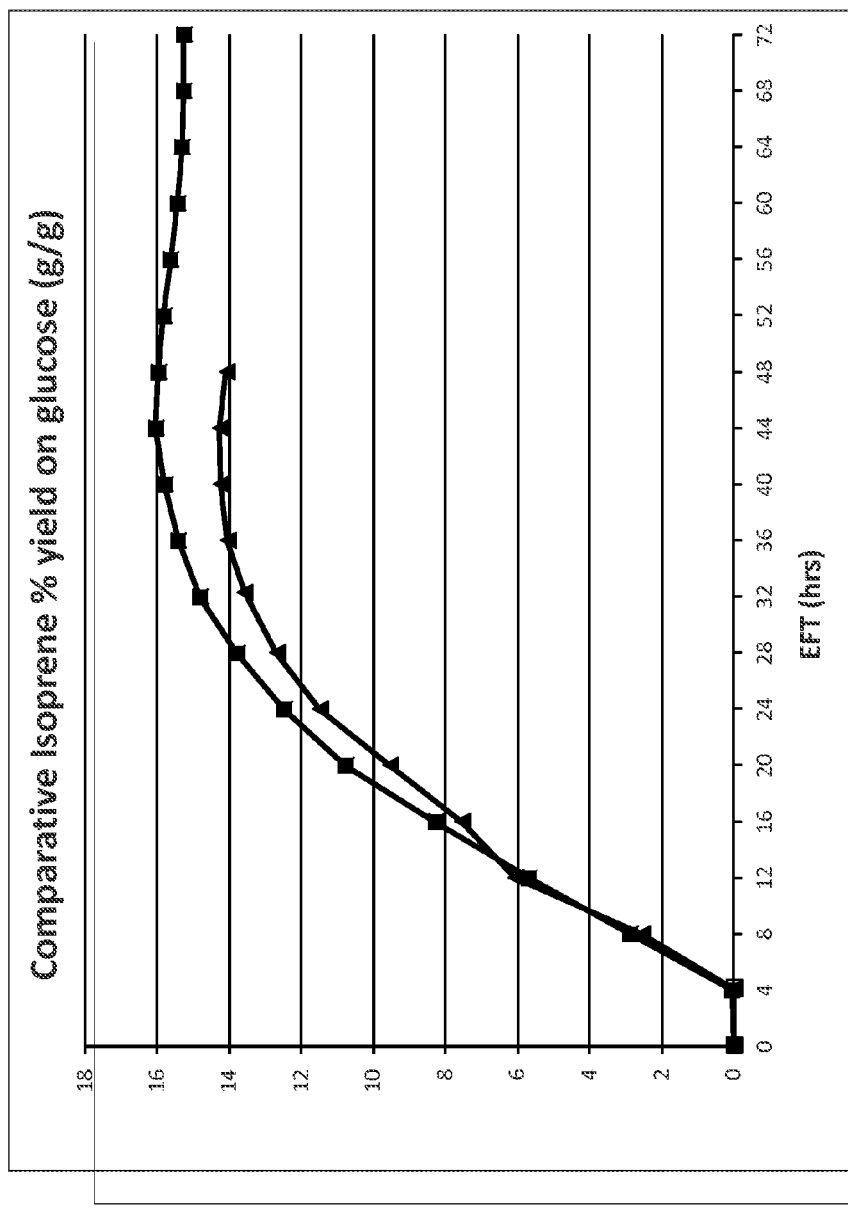

FIG. 9 depicts yield of isoprene on glucose achieved by the yddV-ispA strain CMP1082 (closed black squares), compared the control strain CMP1043 (closed triangles) in a 15-L fermentation over time.

Figure 10:
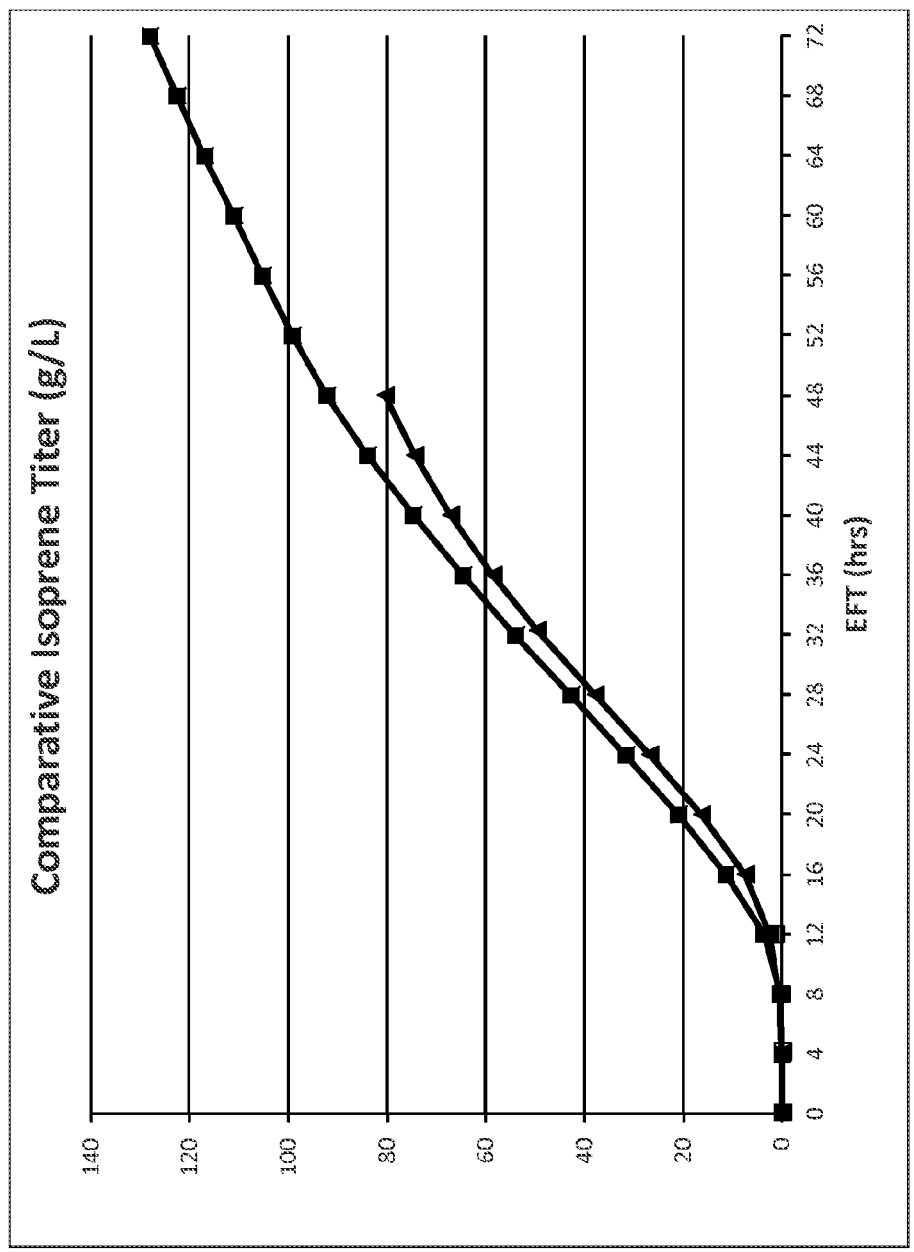

FIG. 10 depicts the isoprene titer achieved by the yddV-ispA strain CMP1082 (closed black squares), compared the control strain CMP1043 (closed triangles) in a 15-L fermentation over time.

Figure 11:
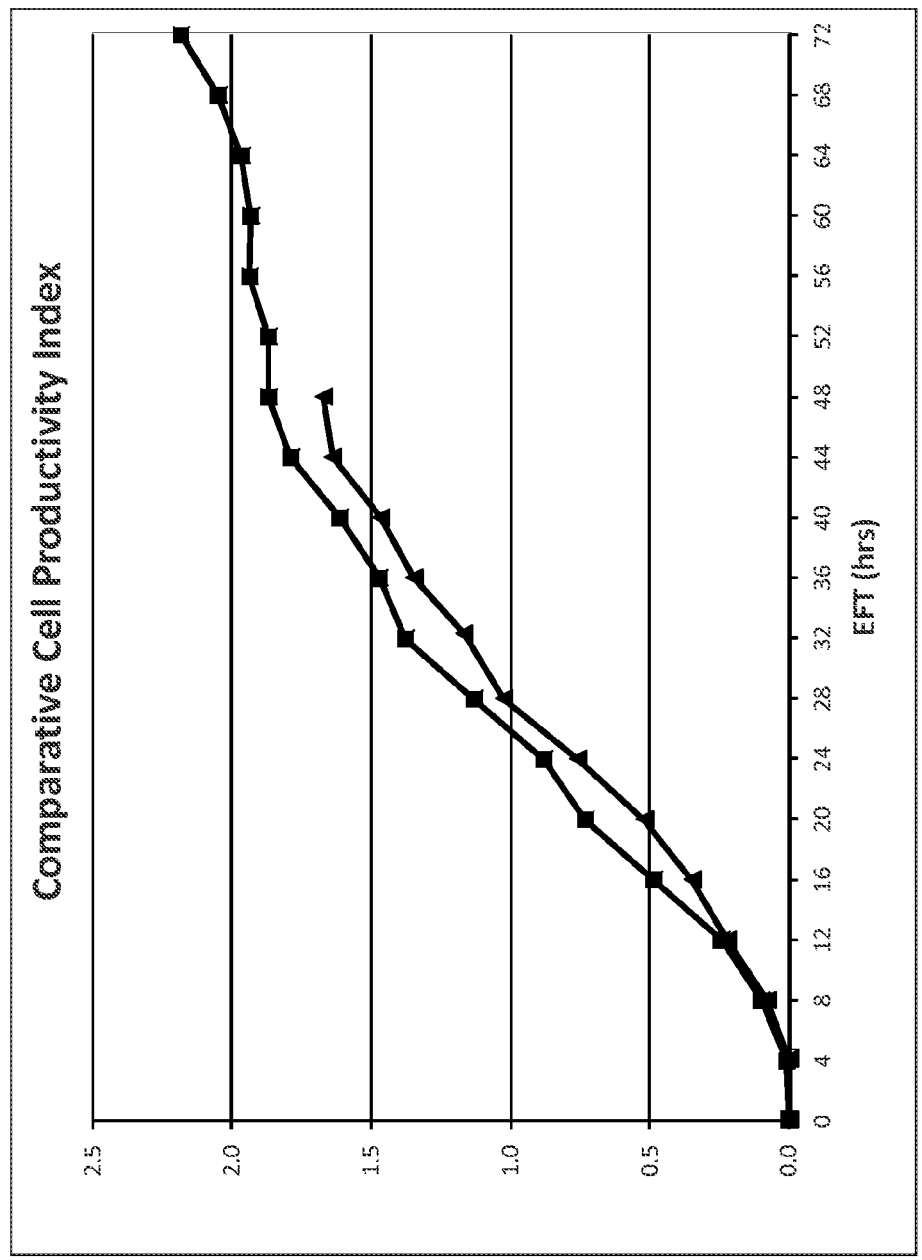

FIG. 11 depicts the Cell Productivity Index (CPI) achieved by the yddV-ispA strain CMP1082 (closed black squares), compared to the control strain CMP1043 (closed triangles) in a 15-L fermentation over time.

Figure 12:
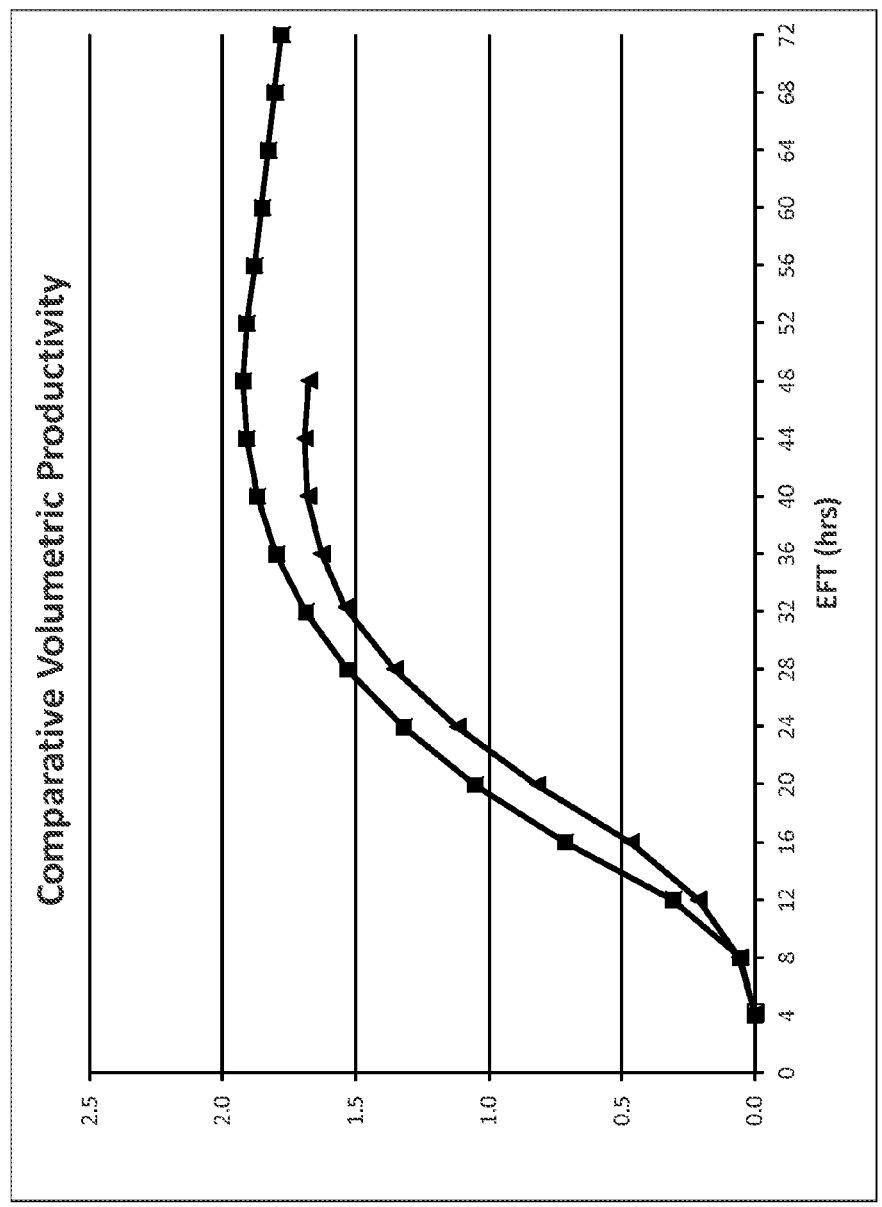

FIG. 12 depicts the volumetric productivity achieved by the yddV-ispA strain CMP1082 (closed black squares), compared the control strain CMP1043 (closed triangles) in a 15-L fermentation over time.

Figure 13:
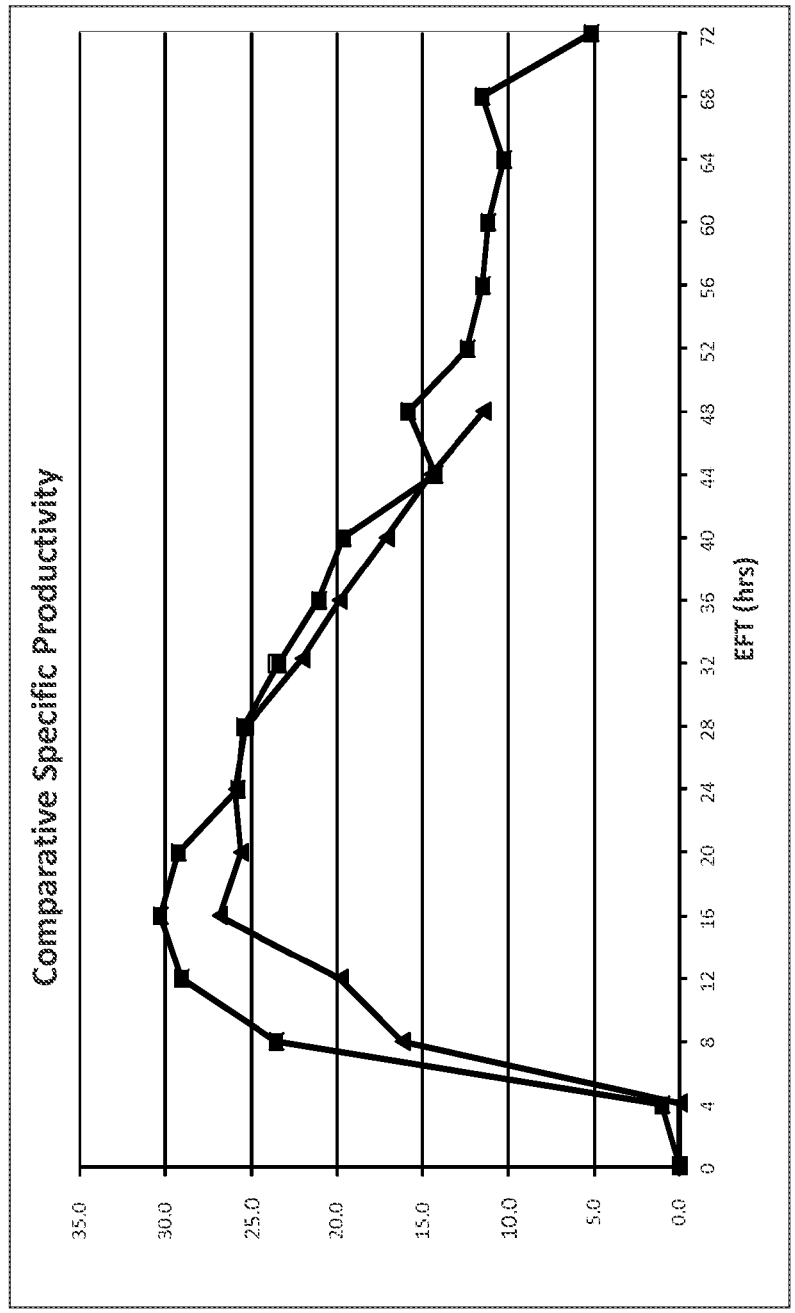

FIG. 13 depicts the specific productivity achieved by the yddV-ispA strain CMP1082 (closed black squares), compared the control strain CMP1043 (closed triangles) in a 15-L fermentation over time.

Figure 14:
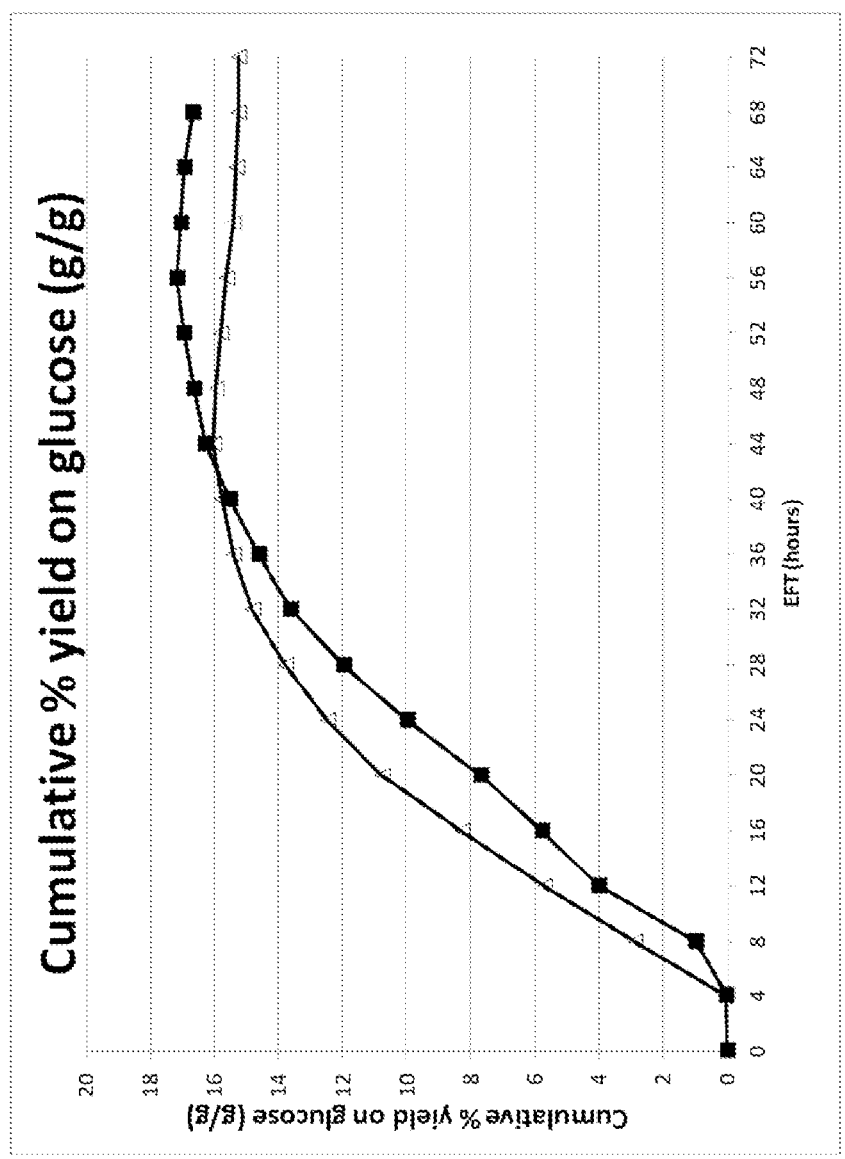

FIG. 14 depicts yield of isoprene on glucose achieved in each 15-L fermentation over time. CMP1082 (pgl+) is depicted by open triangles and CMP1043 (pgl−) is depicted by closed squares.

Figure 15:
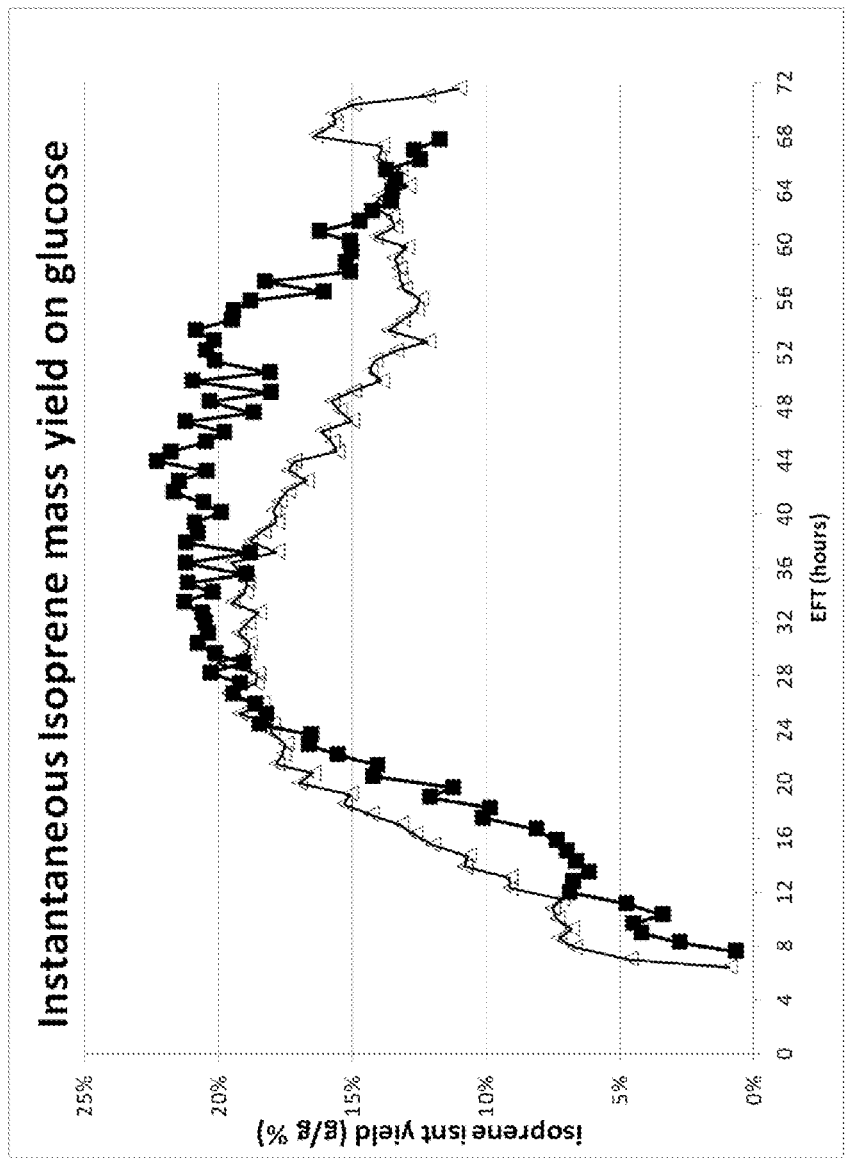

FIG. 15 depicts instantaneous yield of isoprene on glucose achieved in each 15-L fermentation over time. CMP1082 (pgl+) is depicted by open triangles and CMP1043 (pgl−) is depicted by closed squares.

Figure 16:
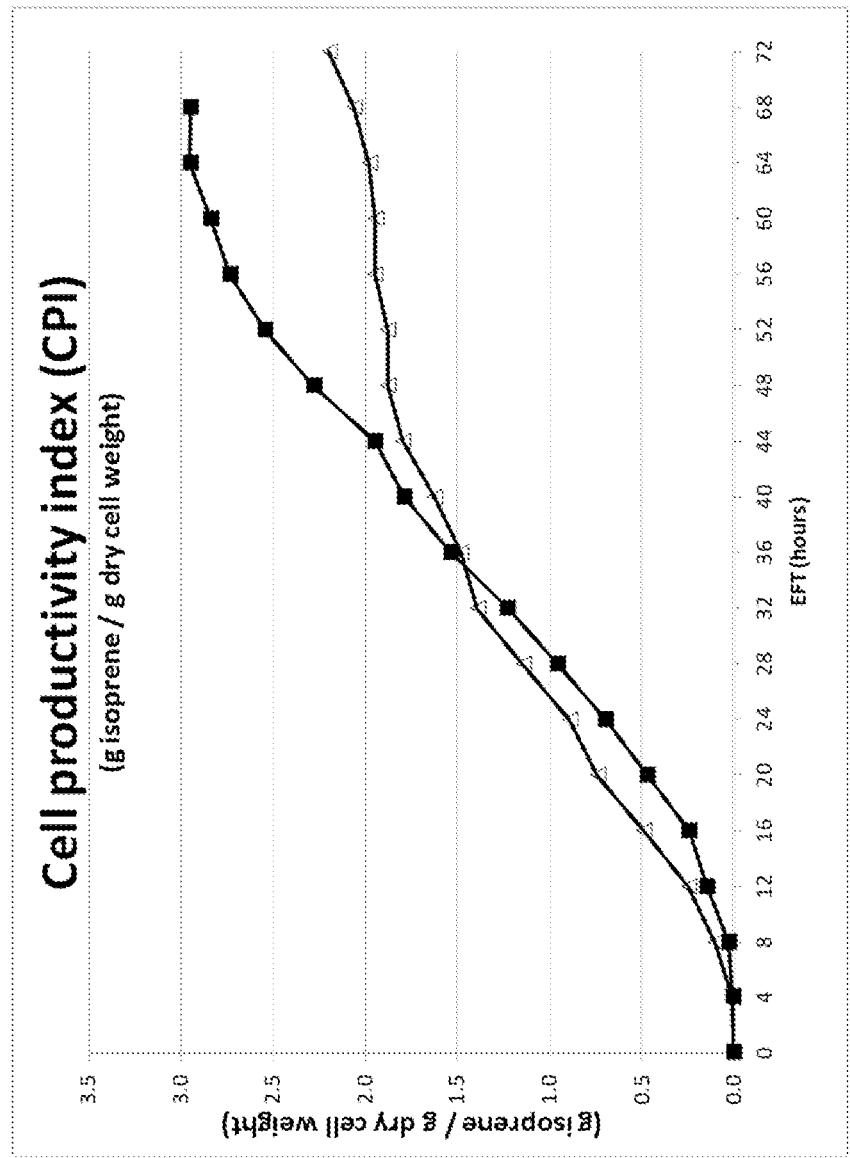

FIG. 16 depicts Cell Productivity Index (CPI) achieved in each 15-L fermentation over time. CMP1082 (pgl+) is depicted by open triangles and CMP1043 (pgl−) is depicted by closed squares.

Figure 17:
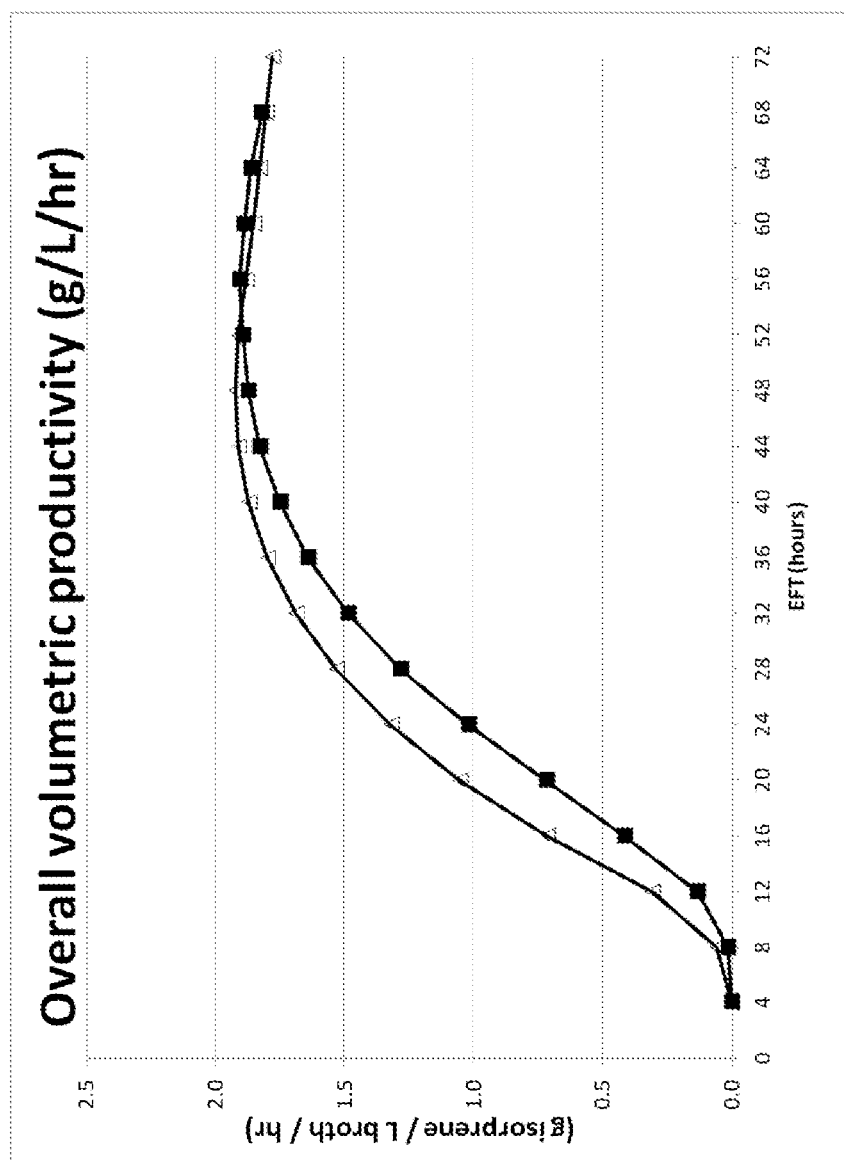

FIG. 17 depicts volumetric productivity achieved in each 15-L fermentation over time. CMP1082 (pgl+) is depicted by open triangles and CMP1043 (pgl−) is depicted by closed squares.

Figure 18:
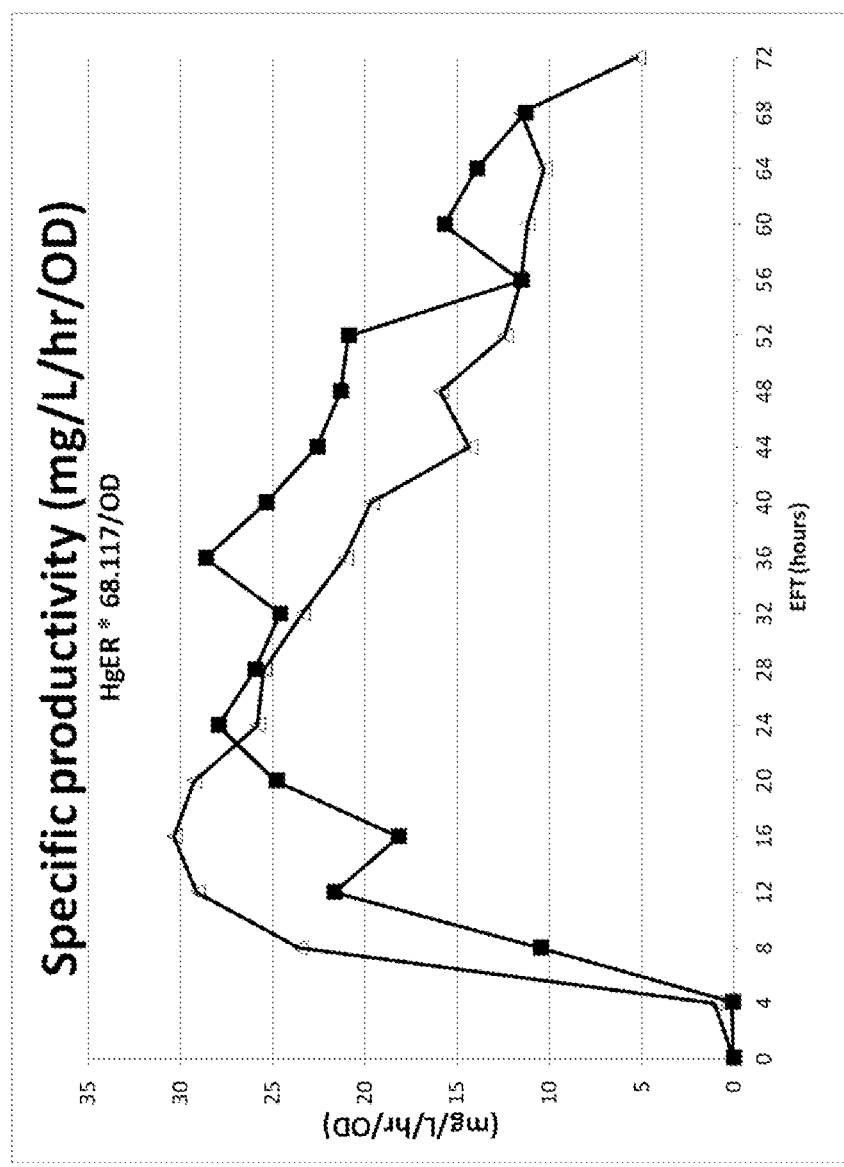

FIG. 18 depicts specific productivity achieved in each 15-L fermentation over time. CMP1082 (pgl+) is depicted by open triangles and CMP1043 (pgl−) is depicted by closed squares.

Figure 19:
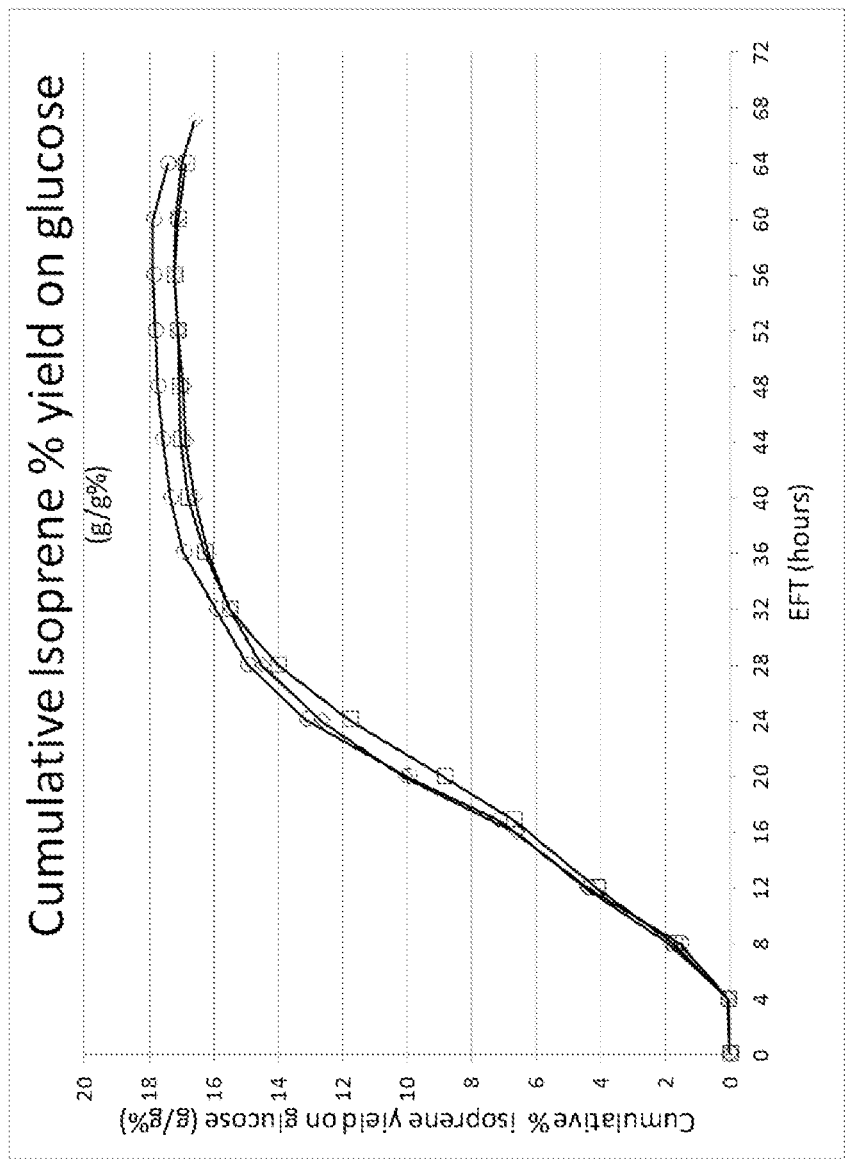

FIG. 19 depicts a graph showing yield of isoprene on glucose achieved in each 15-L fermentation over time. In run 20120522, an improved yield was observed when the inlet gas flowrate was set to 10 standard liters per minute.

Overall yield was calculated using the following formula:

$$\text{\% wt Yield on glucose} = \text{Isoprene total}(t) / [(\text{Feed Wt}(0) - \text{Feed Wt}(t) + 83.5) * 0.59],$$

where 0.59 is the wt % of glucose in the glucose feed solution and 83.5 is the grams of this feed batched into the fermentor at t=0. Each feed had its weight % measured independently.

The run 20120522: DW719 at 10 slpm inlet is depicted by open circles. The run 20120521: DW719 at 14 slpm inlet is depicted by open squares. The run 20120484: DW719 at 8 slpm inlet is depicted by open diamonds.

Figure 20:
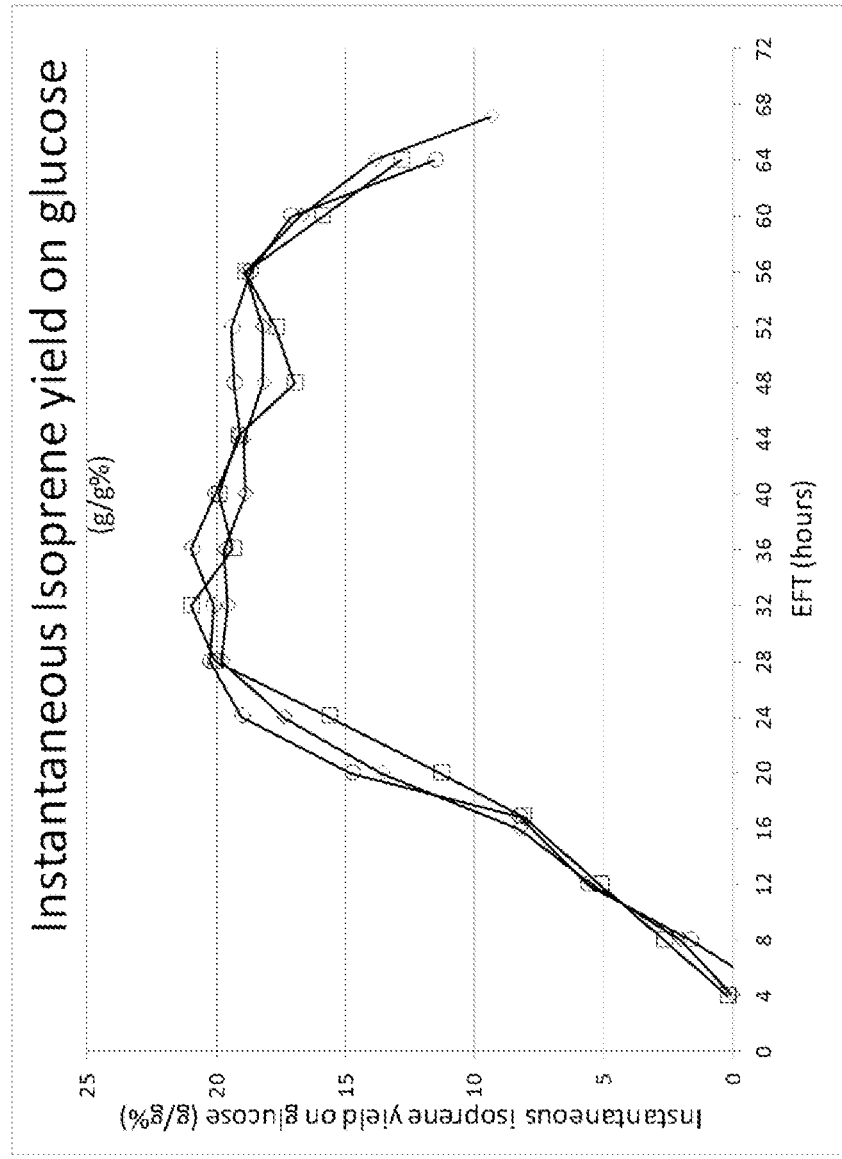

FIG. 20 depicts a graph showing instantaneous yield of isoprene on glucose achieved in each 15-L fermentation over time. In run 20120522, an improved instantaneous yield was observed when the inlet gas flowrate was set to 10 standard liters per minute.

Isoprene instantaneous yield was calculated using the following formula:

$$\text{Isoprene Inst. yield (g/g \%)} = \text{Isoprene produced}(t_1 - t_0) / \text{consumed glucose}(t_1 - t_0) * 100.$$

The run 20120522: DW719 at 10 slpm inlet is depicted by open circles. The run 20120521: DW719 at 14 slpm inlet is depicted by open squares. The run 20120484: DW719 at 8 slpm inlet is depicted by open diamonds.

Figure 21:
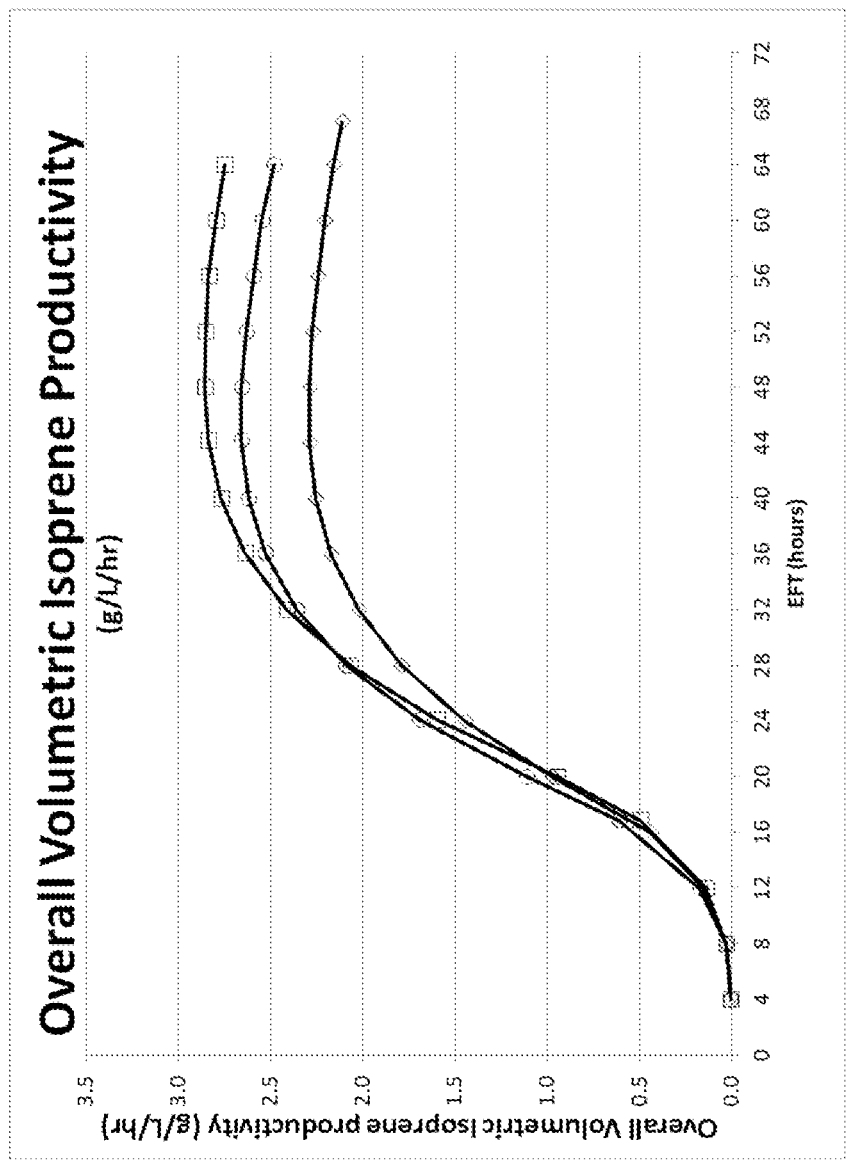

FIG. 21 depicts a graph showing the volumetric productivity achieved in each 15-L fermentation over time. This process runs dissolved oxygen limited from about 16 to 40 hrs EFT. After dissolved oxygen limitation, the oxygen uptake rate is tightly correlated with the oxygen delivery rate. With increasing inlet flow rate came increased oxygen uptake rate, and isoprene productivity correlated well with oxygen uptake rate.

Volumetric Productivity was calculated using the following formula:

$$\text{Volumetric productivity (g/L/hr)} = [\Sigma(\text{HGER}(t)/1000*68.117)]/[t-t_0],$$

where the summation is from $t_0$ to t. Tank turnaround time is not factored in.

The run 20120522: DW719 at 10 slpm inlet is depicted by open circles. The run 20120521: DW719 at 14 slpm inlet is depicted by open squares. The run 20120484: DW719 at 8 slpm inlet is depicted by open diamonds.

Figure 22:
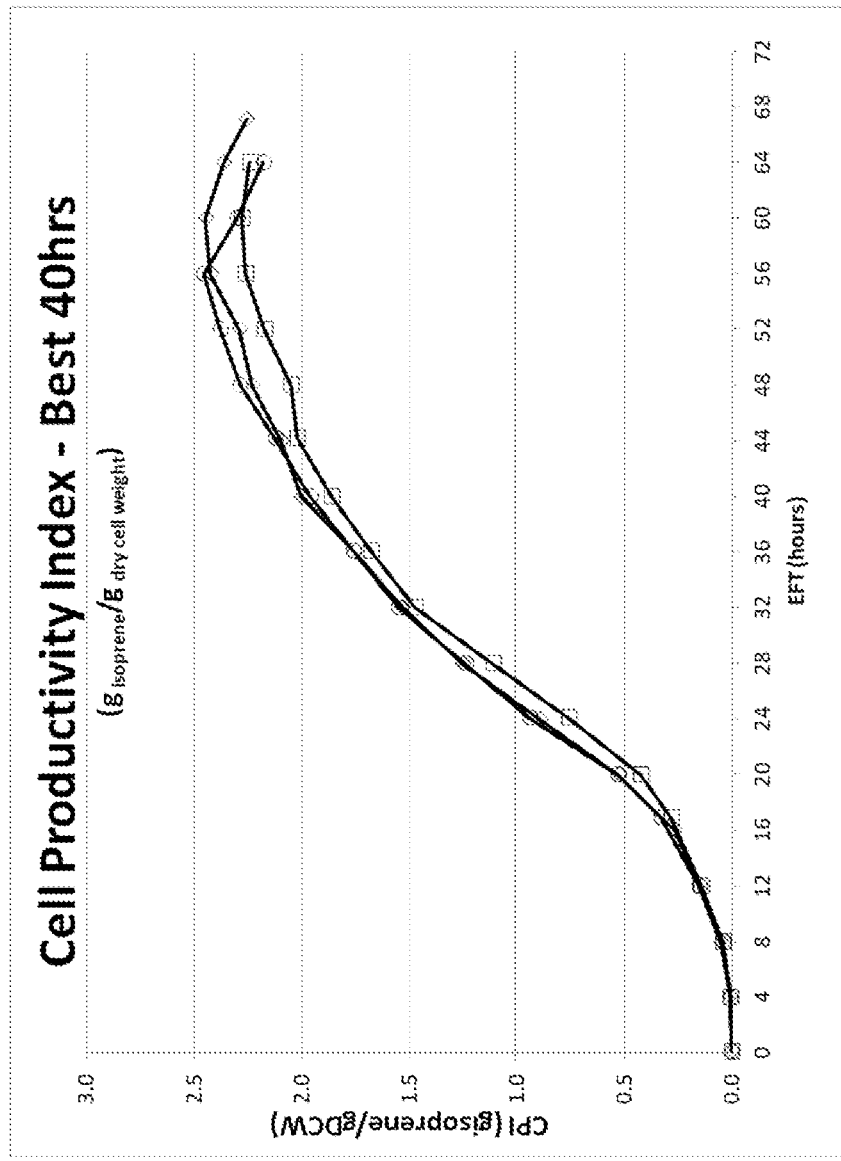

FIG. 22 depicts a graph showing the Cell Productivity Index (CPI) achieved in each 15-L fermentation over time.

Cell Productivity Index (CPI) was calculated using the following formula:

$$\text{CPI} = \text{total grams Isoprene/total grams dry cell weight}$$

The run 20120522: DW719 at 10 slpm inlet is depicted by open circles. The run 20120521: DW719 at 14 slpm inlet is depicted by open squares. The run 20120484: DW719 at 8 slpm inlet is depicted by open diamonds.

Figure 23:
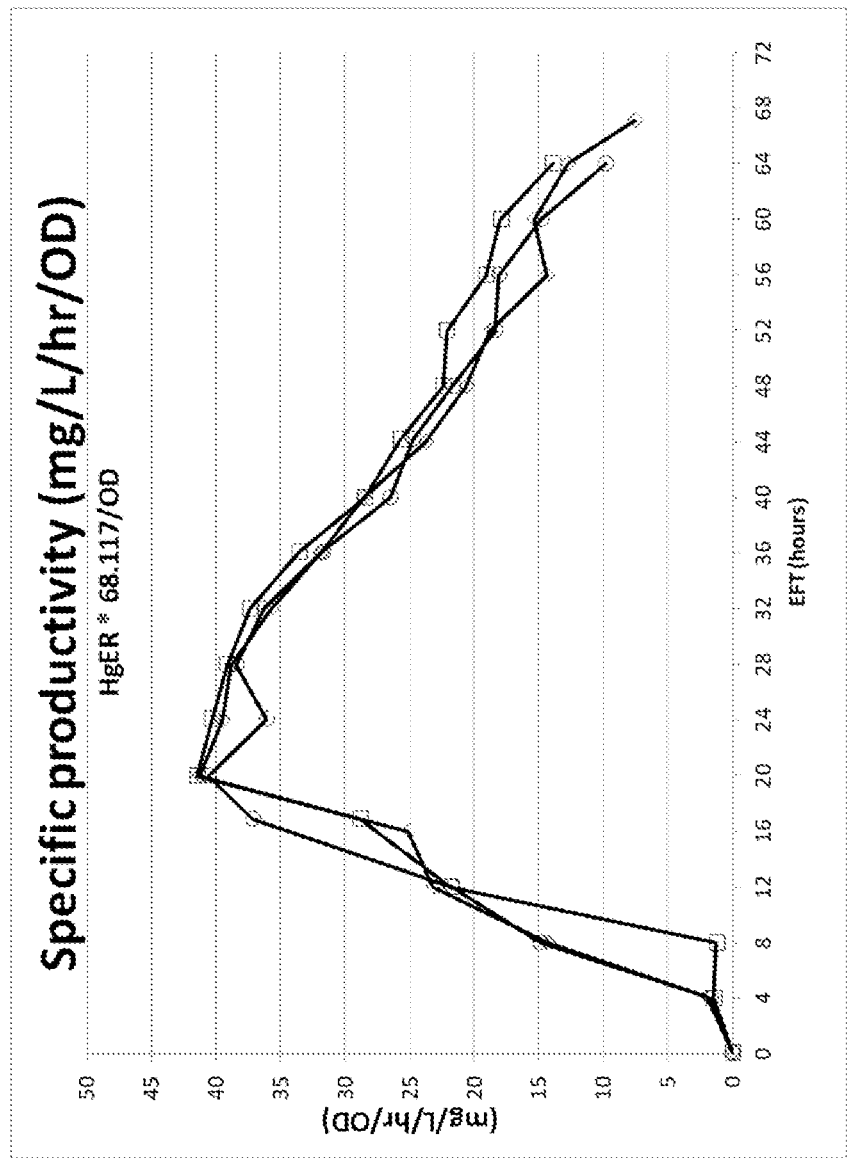

FIG. 23 depicts a graph showing the specific productivity achieved in each 15-L fermentation over time. In run 20120521, a higher specific productivity was observed when the inlet gas flowrate was set to 14 standard liters per minute.

Specific Productivity was calculated using the following formula:

Specific productivity (mg/L/hr/OD)=HgER*68.117 g/mol/OD.

HgER is the Isoprene Evolution Rate in (mmol/L/hr).

OD=optical density=Absorbance at 550 nm*dilution factor in water

In run 20120522: DW719 at 10 slpm inlet is depicted by open circles. In run 20120521: DW719 at 14 slpm inlet is depicted by open squares. In run 20120484: DW719 at 8 slpm inlet is depicted by open diamonds.

DETAILED DESCRIPTION

The invention provided herein discloses, inter alia, methods, compositions and systems for improved production of isoprene using recombinant host cells that have been engineered to produce isoprene under reduced oxygen inlet levels. The invention is based, in part, on the discovery that increased production of isoprene can be achieved when recombinant host cells that have been engineered to produce isoprene (e.g., recombinant cells containing one or more copies of nucleic acid encoding for isoprene synthase) are cultured under reduced oxygen inlet levels, in particular, when these cells are in the production (or fermentation) phase. As is further detailed herein, the recombinant host cells can contain any type of nucleic acid encoding for isoprene synthase (e.g., heterologous or additional copies of endogeneous isoprene synthase). The host cell can also contain additional molecular engineering that can drive additional flux of carbon through metabolic pathways (e.g., MVA pathway and/or DXP pathway) to increase the starting substrate (e.g., DMAPP) for isoprene synthase or to increase the pool of intermediates that can be eventually converted to isoprene. Production of isoprene using recombinant cells (e.g., recombinant cells in production phase) under reduced oxygen inlet levels helps to reduce costs associated with oxygenating fermentation systems, reduces safety hazards (e.g., explosions) and overcomes technical hurdles of increasing the amount of isoprene production while adhering to safety standards (e.g, national standards such as those set forth by National Fire Protection Association 69 or NFPA 69 Standard on Explosion Prevention Systems).

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "*Molecular Cloning: A Laboratory Manual*", third edition (Sambrook et al., 2001); "*Oligonucleotide Synthesis*" (M. J. Gait, ed., 1984); "*Animal Cell Culture: A practical approach*", third edition (J. R. Masters, ed., 2000); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., *Dictionary of Microbiology and Molecular Biology* 3rd revised ed., J. Wiley & Sons (New York, N.Y. 2006), and *March's Advanced Organic Chemistry Reactions, Mechanisms and Structure* 6th ed., John Wiley & Sons (New York, N.Y. 2007), provide one skilled in the art with a general guide to many of the terms used in the present application.

Definitions

The term "isoprene" refers to 2-methyl-1,3-butadiene (CAS #78-79-5). It can be the direct and final volatile C5 hydrocarbon product from the elimination of pyrophosphate from DMAPP. It may not involve the linking or polymerization of IPP molecules to DMAPP molecules. The term "isoprene" is not generally intended to be limited to its method of production unless indicated otherwise herein.

The term "ispA" can refer to any geranyltransferase or farnesyl diphosphate (FPP) synthase enzyme or any member of the prenyl transferase family of enzymes that can catalyze the condensation of isopentenyl diphosphate (IPP) with 3,3-dimethylallyl diphosphate (DMAPP) or geranyl diphosphate (GPP) to yield FPP in any organism. In some embodiments, ispA is encoded by an ispA gene.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

By "heterologous polypeptide" is meant a polypeptide encoded by a nucleic acid sequence derived from a different organism, species, or strain than the host cell. In some embodiments, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

By "heterologous nucleic acid" is meant a nucleic acid sequence derived from a different organism, species or strain than the host cell. In some embodiments, the heterologous nucleic acid is not identical to a wild-type nucleic acid that is found in the same host cell in nature.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

As used herein, the terms "minimal medium" or "minimal media" refer to growth medium containing the minimum nutrients possible for cell growth, generally without the presence of amino acids. Minimal medium typically contains: (1) a carbon source for bacterial growth; (2) various salts, which can vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

As used herein, the term "mass yield" refers to the mass of the product produced by the recombinant (e.g., bacterial) cells divided by the mass of the glucose consumed by the recombinant (e.g., bacterial) cells multiplied by 100.

By "specific productivity," it is meant the mass of the product produced by the bacterial cell divided by the product of the time for production, the cell density, and the volume of the culture.

By "titer," it is meant the mass of the product produced by the recombinant (e.g., bacterial) cells divided by the volume of the culture.

As used herein, the term "cell productivity index (CPI)" refers to the mass of the product produced by the recombinant (e.g., bacterial) cells divided by the mass of the recombinant (e.g., bacterial) cells produced in the culture.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Recombinant Microorganisms Capable of Producing Isoprene

Isoprene (2-methyl-1,3-butadiene) is an important organic compound used in a wide array of applications. For instance, isoprene is employed as an intermediate or a starting material in the synthesis of numerous chemical compositions and polymers, including in the production of synthetic rubber. Isoprene is also an important biological material that is synthesized naturally by many plants and animals. The mevalonate-dependent biosynthetic pathway (MVA pathway) is a key metabolic pathway present in all higher eukaryotes and certain bacteria. In addition to being important for the production of molecules used in processes as diverse as protein prenylation, cell membrane maintenance, protein anchoring, and N-glycosylation, the mevalonate pathway provides a major source of dimethylallyl diphosphate (DMAPP) and isopentenyl diphosphate (IPP), which serve as the basis for the biosynthesis of both isoprenoids and isoprene. DMAPP and IPP provide the initial carbon source input for the biosynthesis of isoprene. The enzyme isoprene synthase uses these molecules to catalyze the production of isoprene.

Various types of microorganism, further detailed herein, can be recombinantly engineered to make isoprene. Recombinant cells that have been engineered to produce isoprene can exhibit two phases in culture: 1) a growth phase wherein the recombinant cells divide in a linear fashion and 2) a production or fermentation phase wherein the cells utilize a carbon source (e.g., glucose) to produce isoprene. As is further detailed herein, various processes and parameters (e.g., reduced oxygen inlet levels) can be used to culture the recombinant microorganism such that it maximizes the production of isoprene.

Isoprene Synthase Nucleic Acids and Polypeptides

In some aspects of the invention, the recombinant cells described in any of the compositions or methods described herein further comprise one or more nucleic acids encoding an isoprene synthase polypeptide or a polypeptide having isoprene synthase activity. In some aspects, the isoprene synthase polypeptide is an endogenous polypeptide. In some aspects, the endogenous nucleic acid encoding an isoprene synthase polypeptide is operably linked to a constitutive promoter. In some aspects, the endogenous nucleic acid encoding an isoprene synthase polypeptide is operably linked to an inducible promoter. In some aspects, the endogenous nucleic acid encoding an isoprene synthase polypeptide is operably linked to a strong promoter. In some aspects, more than one endogenous nucleic acid encoding an isoprene synthase polypeptide is used (e.g, 2, 3, 4, or more copies of an endogenous nucleic acid encoding an isoprene synthase polypeptide). In a particular aspect, the cells are engineered to overexpress the endogenous isoprene synthase pathway polypeptide relative to wild-type cells. In some aspects, the endogenous nucleic acid encoding an isoprene synthase polypeptide is operably linked to a weak promoter. In some aspects, the isoprene synthase polypeptide is a polypeptide from *Pueraria* or *Populus* or a hybrid such as *Populus alba*× *Populus tremula*. In some aspects, the isoprene synthase polypeptide is from *Eucalyptus*.

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter. In some aspects, the isoprene synthase polypeptide is a polypeptide from *Pueraria* or *Populus* or a hybrid such as *Populus alba*×*Populus tremula*. In some aspects, the isoprene synthase polypeptide is from *Eucalyptus*.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase can possess improved activity such as improved enzymatic activity. In some aspects, an isoprene synthase variant has other improved properties, such as improved stability (e.g., thermo-stability), and/or improved solubility.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., *J. Biol. Chem.* 270:13010-13016, 1995. In one exemplary assay, DMAPP (Sigma) can be evaporated to dryness under a stream of nitrogen and rehydrated to a concentration of 100 mM in 100 mM potassium phosphate buffer pH 8.2 and stored at −20° C. To perform the assay, a solution of 5 µL of 1M $MgCl_2$, 1 mM (250 µg/ml) DMAPP, 65 µL of Plant Extract Buffer (PEB) (50 mM Tris-HCl, pH 8.0, 20 mM $MgCl_2$, 5% glycerol, and 2 mM DTT) can be added to 25 µL of cell extract in a 20 ml Headspace vial with a metal screw cap and teflon coated silicon septum (Agilent Technologies) and cultured at 37° C. for 15 minutes with shaking. The reaction can be quenched by adding 200 µL of 250 mM EDTA and quantified by GC/MS.

In some aspects, the heterologous isoprene synthase polypeptide is a plant isoprene synthase polypeptide or a variant thereof. In some aspects, the isoprene synthase polypeptide is an isoprene synthase from *Pueraria* or a variant thereof. In some aspects, the isoprene synthase polypeptide is an isoprene synthase from *Populus* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof. In some aspects, the isoprene synthase polypeptide is a polypeptide from *Pueraria* or *Populus* or a hybrid, *Populus alba*×*Populus tremula*, or a variant thereof. In some aspects, the isoprene synthase polypeptide is from *Eucalyptus*, or a variant thereof. In other aspects, the isoprene synthase is from *Robinia, Salix*, or *Melaleuca*, or variants thereof.

In some aspects, the isoprene synthase polypeptide or nucleic acid is from the family Fabaceae, such as the Faboideae subfamily. In some aspects, the isoprene synthase polypeptide or nucleic acid is a polypeptide or nucleic acid from *Pueraria montana* (kudzu) (Sharkey et al., *Plant Physiology* 137: 700-712, 2005), *Pueraria lobata*, poplar (such as *Populus alba, Populus nigra, Populus trichocarpa*, or *Populus alba*×*tremula* (CAC35696) (Miller et al., *Planta* 213: 483-487, 2001), aspen (such as *Populus tremuloides*) (Silver et al., JBC 270(22): 13010-1316, 1995), English Oak (*Quercus robur*) (Zimmer et al., WO 98/02550), or a variant thereof. In some aspects, the isoprene synthase polypeptide is an isoprene synthase from *Pueraria montana, Pueraria lobata, Populus tremuloides, Populus alba, Populus nigra*, or *Populus trichocarpa* or a variant thereof. In some aspects, the isoprene synthase polypeptide is an isoprene synthase from *Populus alba* or a variant thereof. In some aspects, the isoprene synthase is *Populus balsamifera* (Genbank JN173037), *Populus deltoides* (Genbank JN173039), *Populus fremontii* (Genbank JN173040), *Populus granididenta* (Genbank JN173038), *Salix* (Genbank JN173043), *Robinia pseudoacacia* (Genbank JN173041), *Wisteria* (Genbank JN173042), *Eucalyptus globulus* (Genbank AB266390) or *Melaleuca alterniflora* (Genbank AY279379) or variants thereof. In some aspects, the nucleic acid encoding the isoprene synthase (e.g., isoprene synthase from *Populus alba* or a variant thereof) is codon optimized.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Populus*).

In some aspects, the isoprene synthase polypeptide is a variant. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring isoprene synthase. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the isoprene synthase polypeptide is a variant of naturally occurring isoprene synthase and has improved stability (such as thermo-stability) compared to the naturally occurring isoprene synthase.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild-type or naturally occurring isoprene synthase. The variant can share sequence similarity with a wild-type or naturally occurring isoprene synthase. In some aspects, a variant of a wild-type or naturally occurring isoprene synthase can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring isoprene synthase. In some aspects, a variant of a wild-type or naturally occurring isoprene synthase has any of about 70% to about 99.9%, about 75% to about 99%, about 80% to about 98%, about 85% to about 97%, or about 90% to about 95% amino acid sequence identity as that of the wild-type or naturally occurring isoprene synthase.

In some aspects, the variant comprises a mutation in the wild-type or naturally occurring isoprene synthase. In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, kudzu isoprene synthases, poplar isoprene synthases, English oak isoprene synthases, and willow isoprene synthases. In some aspects, the variant is a variant of isoprene synthase from *Populus alba*. In some aspects, the variant of isoprene synthase from *Populus alba* has at least one amino acid substitution, at least one amino acid insertion, and/or at least one amino acid deletion. In some aspects, the variant is a truncated *Populus alba* isoprene synthase. In some aspects, the nucleic acid encoding variant (e.g., variant of isoprene synthase from *Populus alba*) is codon optimized (for example, codon optimized based on host cells where the heterologous isoprene synthase is expressed).

The isoprene synthase polypeptide provided herein can be any of the isoprene synthases or isoprene synthase variants described in WO 2009/132220, WO 2010/124146, and U.S. Patent Application Publication No.: 2010/0086978, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Suitable isoprene synthases include, but are not limited to, those identified by Genbank Accession Nos. AY341431, AY316691, AY279379, AJ457070, and AY182241. Types of isoprene synthases which can be used in any one of the compositions or methods including methods of making microorganisms encoding isoprene synthase described herein are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/124146, WO2010/078457, WO2010/148256, and Sharkey et al., "*Isoprene Synthase Genes Form A Monophyletic Clade Of Acyclic Terpene Synthases In The Tps-B Terpene Synthase Family*", Evolution (2012) (available on line at DOI: 10.1111/evo.12013), the contents of which are expressly incorporated herein by reference in their entirety with respect to the isoprene synthases and isoprene synthase variants.

MVA Pathway Nucleic Acids and Polypeptides

The complete MVA pathway can be subdivided into two groups: an upper and lower pathway. In the upper portion of the MVA pathway, acetyl Co-A produced during cellular metabolism is converted to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production. In the lower MVA pathway, mevalonate is then converted into mevalonate-5-phosphate via the action of mevalonate kinase which is subsequently transformed into 5-diphosphomevalonate by the enzymatic activity of phosphomevalonate kinase. Finally, IPP is formed from 5-diphosphomevalonate by the activity of the enzyme mevalonate-5-pyrophosphate decarboxylase.

Exemplary MVA pathway polypeptides that can be used include, but are not limited to: 3-hydroxy-3-methylglutaryl-CoA synthase (HMG-CoA synthase) polypeptides (e.g., an enzyme encoded by mvaS), 3-hydroxy-3-methylglutaryl-CoA reductase (HMG-CoA reductase) polypeptides (e.g., enzyme encoded by mvaR or enzyme encoded by mvaE that has been modified to be thiolase-deficient but still retains its reductase activity), mevalonate kinase (MVK) polypeptides, phosphomevalonate kinase (PMK) polypeptides, diphosphomevalonate decarboxylase (MVD) polypeptides, phosphomevalonate decarboxylase (PMDC) polypeptides, isopentenyl phosphate kinase (IPK) polypeptides, IPP isomerase polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein. In addition, variants of MVA pathway polypeptide that confer the result of better isoprene production can also be used as well. In one embodiment, the recombinant cell can be engineered to have an ispA gene with decreased functional activity.

Non-limiting examples of MVA pathway polypeptides which can be used are described in International Patent Application Publication No. WO2009/076676; WO2010/003007 and WO2010/148150.

Acetoacetyl-CoA Synthase Nucleic Acids and Polypeptides

The acetoacetyl-CoA synthase gene (aka nphT7) is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., *PNAS* Vol 107, No. 25, pp. 11265-11270 (2010), the contents of which are expressly incorporated herein for teaching about nphT7. An acetoacetyl-CoA synthase gene from an actinomycete of the genus *Streptomyces* CL190 strain was described in JP Patent Publication (Kokai) No. 2008-61506 A and US2010/0285549. Acetoacetyl-CoA synthase can also be referred to as acetyl CoA:malonyl CoA acyltransferase. A representative acetoacetyl-CoA synthase (or acetyl CoA:malonyl CoA acyltransferase) that can be used is Genbank AB540131.1.

In one embodiment, acetoacetyl-CoA synthase of the present invention synthesizes acetoacetyl-CoA from malonyl-CoA and acetyl-CoA via an irreversible reaction. The use of acetoacetyl-CoA synthase to generate acetyl-CoA provides an additional advantage in that this reaction is irreversible while acetoacetyl-CoA thiolase enzyme's action of synthesizing acetoacetyl-CoA from two acetyl-CoA molecules is reversible. Consequently, the use of acetoacetyl-CoA synthase to synthesize acetoacetyl-CoA from malonyl-CoA and acetyl-CoA can result in significant improvement in productivity for isoprene compared with using thiolase to generate the end same product.

Furthermore, the use of acetoacetyl-CoA synthase to produce isoprene provides another advantage in that acetoacetyl-CoA synthase can convert malonyl CoA to acetyl CoA via decarboxylation of the malonyl CoA. Thus, stores of starting substrate are not limited by the starting amounts of acetyl CoA. The synthesis of acetoacetyl-CoA by acetoacetyl-CoA synthase can still occur when the starting substrate is only malonyl-CoA. In one embodiment, the pool of starting malonyl-CoA is increased by using host strains that have more malonyl-CoA. Such increased pools can be naturally occurring or be engineered by molecular manipulation. See, for example Fowler, et. al, *Applied and Environmental Microbiology*, Vol. 75, No. 18, pp. 5831-5839 (2009).

In any of the aspects or embodiments described herein, an enzyme that has the ability to synthesize acetoacetyl-CoA from malonyl-CoA and acetyl-CoA can be used. Non-limiting examples of such an enzyme are described herein. In certain embodiments described herein, an acetoacetyl-CoA synthase gene derived from an actinomycete of the genus *Streptomyces* having the activity of synthesizing acetoacetyl-CoA from malonyl-CoA and acetyl-CoA can be used.

An example of such an acetoacetyl-CoA synthase gene is the gene encoding a protein having the amino acid sequence of SEQ ID NO: 1. Such a protein having the amino acid sequence of SEQ ID NO: 1 corresponds to an acetoacetyl-CoA synthase having activity of synthesizing acetoacetyl-CoA from malonyl-CoA and acetyl-CoA and having no activity of synthesizing acetoacetyl-CoA from two acetyl-CoA molecules.

In one embodiment, the gene encoding a protein having the amino acid sequence of SEQ ID NO: 1 can be obtained by a nucleic acid amplification method (e.g., PCR) with the use of genomic DNA obtained from an actinomycete of the *Streptomyces* sp. CL190 strain as a template and a pair of primers that can be designed with reference to JP Patent Publication (Kokai) No. 2008-61506A.

As described herein, an acetoacetyl-CoA synthase gene for use in the present invention is not limited to a gene encoding a protein having the amino acid sequence of SEQ ID NO: 1 from an actinomycete of the *Streptomyces* sp. CL190 strain. Any gene encoding a protein having the ability to synthesize acetoacetyl-CoA from malonyl-CoA and acetyl-CoA and which does not synthesize acetoacetyl-CoA from two acetyl-CoA molecules can be used in the presently described methods. In certain embodiments, the acetoacetyl-CoA synthase gene can be a gene encoding a protein having an amino acid sequence with high similarity or substantially identical to the amino acid sequence of SEQ ID NO: 1 and having the function of synthesizing acetoacetyl-CoA from malonyl-CoA and acetyl-CoA. The expression "highly similar" or "substantially identical" refers to, for example, at least about 80% identity, at least about 85%, at least about 90%, at least about 91%, at least about 92%, at least about 93%, at least about 94%, at least about 95%, at least about 96%, at least about 97%, at least about 98%, and at least about 99% identity. As used above, the identity value corresponds to the percentage of identity between amino acid residues in a different amino acid sequence and the amino acid sequence of SEQ ID NO: 1, which is calculated by performing alignment of the amino acid sequence of SEQ ID NO: 1 and the different amino acid sequence with the use of a program for searching for a sequence similarity.

In other embodiments, the acetoacetyl-CoA synthase gene may be a gene encoding a protein having an amino acid sequence derived from the amino acid sequence of SEQ ID NO: 1 by substitution, deletion, addition, or insertion of 1 or more amino acid(s) and having the function of synthesizing acetoacetyl-CoA from malonyl-CoA and acetyl-CoA. Herein, the expression "more amino acids" refers to, for example, 2 to 30 amino acids, preferably 2 to 20 amino acids, more preferably 2 to 10 amino acids, and most preferably 2 to 5 amino acids.

In still other embodiments, the acetoacetyl-CoA synthase gene may consist of a polynucleotide capable of hybridizing to a portion or the entirety of a polynucleotide having a nucleotide sequence complementary to the nucleotide sequence encoding the amino acid sequence of SEQ ID NO: 1 under stringent conditions and capable of encoding a protein having the function of synthesizing acetoacetyl-CoA from malonyl-CoA and acetyl-CoA. Herein, hybridization under stringent conditions corresponds to maintenance of binding under conditions of washing at 60° C. 2×. Hybridization can be carried out by conventionally known methods such as the method described in J. Sambrook et al. Molecular Cloning, A Laboratory Manual, 3rd Ed., Cold Spring Harbor Laboratory (2001).

As described herein, a gene encoding an acetoacetyl-CoA synthase having an amino acid sequence that differs from the amino acid sequence of SEQ ID NO: 1 can be isolated from potentially any organism, for example, an actinomycete that is not obtained from the *Streptomyces* sp. CL190 strain. In addition, acetoacetyl-CoA synthase genes for use herein can be obtained by modifying a polynucleotide encoding the amino acid sequence of SEQ ID NO: 1 by a method known in the art. Mutagenesis of a nucleotide sequence can be carried out by a known method such as the Kunkel method or the gapped duplex method or by a method similar to either thereof. For instance, mutagenesis may be carried out with the use of a mutagenesis kit (e.g., product names; Mutant-K and Mutant-G (TAKARA Bio)) for site-specific mutagenesis, product name; an LA PCR in vitro Mutagenesis series kit (TAKARA Bio), and the like.

The activity of an acetoacetyl-CoA synthase having an amino acid sequence that differs from the amino acid sequence of SEQ ID NO: 1 can be evaluated as described below. Specifically, a gene encoding a protein to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of reaction, the amount of substrate lost and/or the amount of product (acetoacetyl-CoA) produced are determined. Thus, it is possible to evaluate whether or not the protein being tested has the function of synthesizing acetoacetyl-CoA from malonyl-CoA and acetyl-CoA and to evaluate the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and determining the amount of substrate lost and/or the amount of product produced in a similar manner.

Nucleic Acids Encoding Polypeptides of the Upper MVA Pathway

The upper portion of the MVA pathway uses acetyl Co-A produced during cellular metabolism as the initial substrate for conversion to mevalonate via the actions of polypeptides having either: (a) (i) thiolase activity or (ii) acetoacetyl-CoA activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production.

Non-limiting examples of upper MVA pathway polypeptides that can be used include: acetyl-CoA acetyltransferase (AA-CoA thiolase) polypeptides, acetoacetyl-CoA synthase polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides. Upper MVA pathway polypeptides can include polypeptides, fragments of polypeptides, peptides, and fusions polypeptides that have at least one activity of an upper MVA pathway polypeptide. Exemplary upper MVA pathway nucleic acids include nucleic acids that encode a polypeptide, fragment of a polypeptide, peptide, or fusion polypeptide that has at least one activity of an upper MVA pathway polypeptide. Exemplary MVA pathway polypeptides and nucleic acids include naturally-occurring polypeptides and nucleic acids from any of the source organisms described herein. Thus, it is contemplated herein that any gene encoding an upper MVA pathway polypeptide can be used in the present invention. In one embodiment, the recombinant cell can be engineered to have an ispA gene with decreased functional activity.

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In other embodiments, an acetoacetyl-CoA synthase gene is contemplated within the scope of the present invention in combination with one or more other genes encoding: (i) 3-hydroxy-3-methylglutaryl-CoA synthase (HMG-CoA synthase) polypeptides and 3-hydroxy-3-methylglutaryl-CoA reductase (HMG-CoA reductase) polypeptides. Thus, in certain aspects, any of the combinations of genes contemplated can be expressed in recombinant cells in any of the ways described herein. In one embodiment, the recombinant cell can be engineered to have an ispA gene with decreased functional activity.

Additional non-limiting examples of upper MVA pathway polypeptides which can be used herein are described in International Patent Application Publication No. WO2009/076676; WO2010/003007 and WO2010/148150.

Genes Encoding mvaE and mvaS Polypeptides

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention in conjunction with an IspA having decreased functional activity in recombinant cells. In *L. grayi, E. faecium, E. gallinarum, E. casseliflavus*, and *E. faecalis*, the mvaE gene encodes a polypeptide that possesses both thiolase and HMG-CoA reductase activities (Hedl, et al., *J Bacteriol*. 2002 April; 184(8): 2116-2122). The mvaS gene, on the other hand, encodes a polypeptide having an HMG-CoA synthase activity.

Accordingly, recombinant cells (e.g., *E. coli*) can be engineered to express one or more mvaE and mvaS genes from *L. grayi, E. faecium, E. gallinarum, E. casseliflavus* and/or *E. faecalis*, to produce isoprene. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes. In one embodiment, the recombinant cell can be engineered to have an ispA gene with decreased functional activity.

The mvaE gene encodes a polypeptide that possesses both thiolase and HMG-CoA reductase activities. The thiolase activity of the polypeptide encoded by the mvaE gene converts acetyl Co-A to acetoacetyl CoA whereas the HMG-CoA reductase enzymatic activity of the polypeptide converts 3-hydroxy-3-methylglutaryl-CoA to mevalonate. Exemplary mvaE polypeptides and nucleic acids include naturally-occurring polypeptides and nucleic acids from any of the source organisms described herein as well as mutant polypeptides and nucleic acids derived from any of the source organisms described herein that have at least one activity of a mvaE polypeptide.

Mutant mvaE polypeptides include those in which one or more amino acid residues have undergone an amino acid substitution while retaining mvaE polypeptide activity (i.e., the ability to convert acetyl Co-A to acetoacetyl CoA as well as the ability to convert 3-hydroxy-3-methylglutaryl-CoA to mevalonate). The amino acid substitutions can be conservative or non-conservative and such substituted amino acid residues can or cannot be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

Amino acid substitutions in the mvaE polypeptide can be introduced to improve the functionality of the molecule. For example, amino acid substitutions that increase the binding affinity of the mvaE polypeptide for its substrate, or that improve its ability to convert acetyl Co-A to acetoacetyl CoA and/or the ability to convert 3-hydroxy-3-methylglutaryl- CoA to mevalonate can be introduced into the mvaE polypeptide. In some aspects, the mutant mvaE polypeptides contain one or more conservative amino acid substitutions.

In one aspect, mvaE proteins that are not degraded or less prone to degradation can be used for the production of isoprene. Examples of gene products of mvaEs that are not degraded or less prone to degradation which can be used include, but are not limited to, those from the organisms *E. faecium, E. gallinarum, E. casseliflavus, E. faecalis*, and *L. grayi*. One of skill in the art can express mvaE protein in *E. coli* BL21 (DE3) and look for absence of fragments by any standard molecular biology techniques. For example, absence of fragments can be identified on Safestain stained SDS-PAGE gels following His-tag mediated purification or when expressed in mevalonate, isoprene or isoprenoid producing *E. coli* BL21 using the methods of detection described herein.

Standard methods, such as those described in Hedl et al., (*J Bacteriol.* 2002, April; 184(8): 2116-2122) can be used to determine whether a polypeptide has mvaE activity, by measuring acetoacetyl-CoA thiolase as well as HMG-CoA reductase activity. In an exemplary assay, acetoacetyl-CoA thiolase activity is measured by spectrophotometer to monitor the change in absorbance at 302 nm that accompanies the formation or thiolysis of acetoacetyl-CoA. Standard assay conditions for each reaction to determine synthesis of acetoacetyl-CoA, are 1 mM acetyl-CoA, 10 mM $MgCl_2$, 50 mM Tris, pH 10.5 and the reaction is initiated by addition of enzyme. Assays can employ a final volume of 200 µl. For the assay, 1 enzyme unit (eu) represents the synthesis or thiolysis in 1 min of 1 µmol of acetoacetyl-CoA. In another exemplary assay, of HMG-CoA reductase activity can be monitored by spectrophotometer by the appearance or disappearance of NADP(H) at 340 nm. Standard assay conditions for each reaction measured to show reductive deacylation of HMG-CoA to mevalonate are 0.4 mM NADPH, 1.0 mM (R,S)-HMG-CoA, 100 mM KCl, and 100 mM $K_xPO_4$, pH 6.5. Assays employ a final volume of 200 µl. Reactions are initiated by adding the enzyme. For the assay, 1 eu represents the turnover, in 1 min, of 1 µmol of NADP(H). This corresponds to the turnover of 0.5 µmol of HMG-CoA or mevalonate.

Exemplary mvaE nucleic acids include nucleic acids that encode a polypeptide, fragment of a polypeptide, peptide, or fusion polypeptide that has at least one activity of a mvaE polypeptide. Exemplary mvaE polypeptides and nucleic acids include naturally-occurring polypeptides and nucleic acids from any of the source organisms described herein as well as mutant polypeptides and nucleic acids derived from any of the source organisms described herein. Exemplary mvaE nucleic acids include, for example, mvaE nucleic acids isolated from *Listeria grayi*_DSM 20601, *Enterococcus faecium, Enterococcus gallinarum* EG2, *Enterococcus faecalis*, and/or *Enterococcus casseliflavus*. The mvaE nucleic acid encoded by the *Listeria grayi*_DSM 20601 mvaE gene can have a 99%, 98%, 97%, 96%, 95%, 95%, 93%, 92%, 91%, 90%, 89%, 88%, 87%, 86%, or 85% sequence identity to SEQ ID NO: 2. The mvaE nucleic acid encoded by the *Enterococcus faecium* mvaE gene can have a 99%, 98%, 97%, 96%, 95%, 95%, 93%, 92%, 91%, 90%, 89%, 88%, 87%, 86%, or 85% sequence identity to SEQ ID NO: 3. The mvaE nucleic acid encoded by the *Enterococcus gallinarum* EG2 mvaE gene can have a 99%, 98%, 97%, 96%, 95%, 95%, 93%, 92%, 91%, 90%, 89%, 88%, 87%, 86%, or 85% sequence identity to SEQ ID NO:4. The mvaE nucleic acid encoded by the *Enterococcus casseliflavus* mvaE gene can have a 99%, 98%, 97%, 96%, 95%, 95%, 93%, 92%, 91%, 90%, 89%, 88%, 87%, 86%, or 85% sequence identity to SEQ ID NO:5. The mvaE nucleic acid encoded by the *Enterococcus faecalis* mvaE gene can have a 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. *Biotechnology Letters* 26: 1487-1491, 2004).

The mvaE nucleic acid can be expressed in a recombinant cell on a multicopy plasmid. The plasmid can be a high copy plasmid, a low copy plasmid, or a medium copy plasmid. Alternatively, the mvaE nucleic acid can be integrated into the host cell's chromosome. For both heterologous expression of an mvaE nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaE nucleic acid.

The mvaS gene encodes a polypeptide that possesses HMG-CoA synthase activity. This polypeptide can convert acetoacetyl CoA to 3-hydroxy-3-methylglutaryl-CoA (HMG-CoA). Exemplary mvaS polypeptides and nucleic acids include naturally-occurring polypeptides and nucleic acids from any of the source organisms described herein as well as mutant polypeptides and nucleic acids derived from any of the source organisms described herein that have at least one activity of a mvaS polypeptide.

Mutant mvaS polypeptides include those in which one or more amino acid residues have undergone an amino acid substitution while retaining mvaS polypeptide activity (i.e., the ability to convert acetoacetyl CoA to 3-hydroxy-3-methylglutaryl-CoA). Amino acid substitutions in the mvaS polypeptide can be introduced to improve the functionality of the molecule. For example, amino acid substitutions that increase the binding affinity of the mvaS polypeptide for its substrate, or that improve its ability to convert acetoacetyl CoA to 3-hydroxy-3-methylglutaryl-CoA can be introduced into the mvaS polypeptide. In some aspects, the mutant mvaS polypeptides contain one or more conservative amino acid substitutions.

Standard methods, such as those described in Quant et al. (*Biochem J.*, 1989, 262:159-164), can be used to determine whether a polypeptide has mvaS activity, by measuring HMG-CoA synthase activity. In an exemplary assay, HMG-CoA synthase activity can be assayed by spectrophotometrically measuring the disappearance of the enol form of acetoacetyl-CoA by monitoring the change of absorbance at 303 nm. A standard 1 ml assay system containing 50 mm-Tris/HCl, pH 8.0, 10 mM-$MgCl2$ and 0.2 mM-dithiothreitol at 30° C.; 5 mM-acetyl phosphate, 10, M-acetoacetyl-CoA and 5 µl samples of extracts can be added, followed by simultaneous addition of acetyl-CoA (100 µM) and 10 units of PTA. HMG-CoA synthase activity is then measured as the difference in the rate before and after acetyl-CoA addition. The absorption coefficient of acetoacetyl-CoA under the conditions used (pH 8.0, 10 mM—$MgCl_2$), is $12.2 \times 10^3$ $M^{-1}$ $cm^{-1}$. By definition, 1 unit of enzyme activity causes 1 µmol of acetoacetyl-CoA to be transformed per minute.

Exemplary mvaS nucleic acids include nucleic acids that encode a polypeptide, fragment of a polypeptide, peptide, or fusion polypeptide that has at least one activity of a mvaS polypeptide. Exemplary mvaS polypeptides and nucleic acids include naturally-occurring polypeptides and nucleic acids from any of the source organisms described herein as well as mutant polypeptides and nucleic acids derived from any of the source organisms described herein. Exemplary mvaS nucleic acids include, for example, mvaS nucleic acids isolated from *Listeria grayi*_DSM 20601, *Enterococcus faecium, Enterococcus gallinarum* EG2, *Enterococcus faecalis,* and/or *Enterococcus casseliflavus.* The mvaS nucleic acid encoded by the *Listeria grayi*_DSM 20601 mvaS gene can have a 99%, 98%, 97%, 96%, 95%, 95%, 93%, 92%, 91%, 90%, 89%, 88%, 87%, 86%, or 85% sequence identity to SEQ ID NO: 6. The mvaS nucleic acid encoded by the *Enterococcus faecium* mvaS gene can have a 99%, 98%, 97%, 96%, 95%, 95%, 93%, 92%, 91%, 90%, 89%, 88%, 87%, 86%, or 85% sequence identity to SEQ ID NO:7. The mvaS nucleic acid encoded by the *Enterococcus gallinarum* EG2 mvaS gene can have a 99%, 98%, 97%, 96%, 95%, 95%, 93%, 92%, 91%, 90%, 89%, 88%, 87%, 86%, or 85% sequence identity to SEQ ID NO:8. The mvaS nucleic acid encoded by the *Enterococcus casseliflavus* mvaS gene can have a 99%, 98%, 97%, 96%, 95%, 95%, 93%, 92%, 91%, 90%, 89%, 88%, 87%, 86%, or 85% sequence identity to SEQ ID NO:9. The mvaS nucleic acid encoded by the *Enterococcus faecalis* mvaS gene can have a 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. *Biotechnology Letters* 26: 1487-1491, 2004).

The mvaS nucleic acid can be expressed in a recombinant cell on a multicopy plasmid. The plasmid can be a high copy plasmid, a low copy plasmid, or a medium copy plasmid. Alternatively, the mvaS nucleic acid can be integrated into the host cell's chromosome. For both heterologous expression of an mvaS nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaS nucleic acid.

Compositions of recombinant cells as described herein are contemplated within the scope of the invention as well. It is understood that recombinant cells also encompass progeny cells as well.

Nucleic Acids Encoding Polypeptides of the Lower MVA Pathway

In some aspects of the invention, the cells described in any of the compositions or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonate decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, and *Methanococoides burtonii* mevalonate kinase polypeptide. In another aspect, the enzyme that phosphorylates mevalonate to mevalonate 5-phosphate is *M. mazei* mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from *Saccharomyces cerevisiae, Enterococcus faecalis, Methanosarcina mazei,* or *Methanococoides burtonii.*

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus *Methanosarcina* and, more specifically, the lower MVK polypeptide can be from *Methanosarcina mazei*. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variants.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo.

Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from *Saccharomyces cerevisiae, Enterococcus faecalis, Methanosarcina mazei*, or *Methanococoides burtonii*. In some aspects, the MVK polypeptide is selected from the group consisting of *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, and *Methanosarcina mazei* mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

DXP Pathway Nucleic Acids and Polypeptides

In some aspects of the invention, the recombinant cells described in any of the compositions or methods described herein further comprise one or more heterologous nucleic acids encoding a DXS polypeptide or other DXP pathway polypeptides. In some aspects, the cells further comprise a chromosomal copy of an endogenous nucleic acid encoding a DXS polypeptide or other DXP pathway polypeptides. In some aspects, the *E. coli* cells further comprise one or more nucleic acids encoding an IDI polypeptide and a DXS polypeptide or other DXP pathway polypeptides. In some aspects, one nucleic acid encodes the isoprene synthase polypeptide, IDI polypeptide, and DXS polypeptide or other DXP pathway polypeptides. In some aspects, one plasmid encodes the isoprene synthase polypeptide, IDI polypeptide, and DXS polypeptide or other DXP pathway polypeptides. In some aspects, multiple plasmids encode the isoprene synthase polypeptide, IDI polypeptide, and DXS polypeptide or other DXP pathway polypeptides.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No.: WO 2010/148150

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). In one embodiment, the ispH gene can be used to encode for HDR polypeptides. IspH is also known as 1-hydroxy-2-methyl-2-(E)-butenyl 4-diphosphate reductase, 4Fe-4S protein, ECK0030, JW0027, lytB, yaaE, and b0029. Standard methods can be used to determine whether a polypeptide has HDR polypeptides activity by measuring the ability of the polypeptide to convert HMBPP in vitro, in a cell extract, or in vivo.

Source Organisms for MVA Pathway, Isoprene Synthase, IDI, and DXP Pathway Polypeptides Isoprene synthase, IDI, DXP pathway, and/or MVA pathway nucleic acids can be obtained from any organism that naturally contains isoprene synthase, IDI, DXP pathway, and/or MVA pathway nucleic acids. Isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. IDI and DXP pathway nucleic acids can be obtained, e.g., from any organism that contains the IDI and DXP pathway.

The nucleic acid sequence of the isoprene synthase, DXP pathway, IDI, and/or MVA pathway nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., *Methanosarcina mazei*), plants, such as kudzu or poplar (e.g., *Populus alba* or *Populus albaxtremula* CAC35696) or aspen (e.g., *Populus tremuloides*). Exemplary sources for isoprene synthases, IDI, and/or MVA pathway polypeptides which can be used are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/078457, and WO2010/148256.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Corynebacteria*, strains of *Enterobacter*, strains of *Streptococcus*, or strains of Archaea such as *Methanosarcina mazei*.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

In some aspects, the source organism is a gram-positive bacterium. Non-limiting examples include strains of *Streptomyces* (e.g., *S. lividans, S. coelicolor,* or *S. griseus*) and *Bacillus*. In some aspects, the source organism is a gram-negative bacterium, such as *E. coli* or *Pseudomonas* sp. In some aspects, the source organism is *L. acidophilus*.

In some aspects, the source organism is a plant, such as a plant from the family Fabaceae, such as the Faboideae subfamily. In some aspects, the source organism is kudzu, poplar (such as *Populus albaxtremula* CAC35696), aspen (such as *Populus tremuloides*), or *Quercus robur*.

In some aspects, the source organism is an algae, such as a green algae, red algae, glaucophytes, chlorarachniophytes, euglenids, chromista, or dinoflagellates.

In some aspects, the source organism is a cyanobacteria, such as cyanobacteria classified into any of the following groups based on morphology: Chroococcales, Pleurocapsales, Oscillatoriales, Nostocales, or Stigonematales.

Phosphoketolase Nucleic Acids and Polypeptides

In some aspects of the invention, the recombinant cells described in any of the compositions or methods described herein further comprise one or more nucleic acids encoding an phosphoketolase polypeptide or a polypeptide having phosphoketolase activity. In some aspects, the phosphoketolase polypeptide is an endogenous polypeptide. In some aspects, the endogenous nucleic acid encoding a phosphoketolase polypeptide is operably linked to a constitutive promoter. In some aspects, the endogenous nucleic acid encoding a phosphoketolase polypeptide is operably linked to an inducible promoter. In some aspects, the endogenous nucleic acid encoding a phosphoketolase polypeptide is operably linked to a strong promoter. In some aspects, more than one endogenous nucleic acid encoding a phosphoketolase polypeptide is used (e.g, 2, 3, 4, or more copies of an endogenous nucleic acid encoding a phosphoketolase polypeptide). In a particular aspect, the cells are engineered to overexpress the endogenous phosphoketolase polypeptide relative to wild-type cells. In some aspects, the endogenous nucleic acid encoding a phosphoketolase polypeptide is operably linked to a weak promoter.

Phosphoketolase enzymes catalyze the conversion of xylulose 5-phosphate to glyceraldehyde 3-phosphate and acetyl phosphate and/or the conversion of fructose 6-phosphate to erythrose 4-phosphate and acetyl phosphate. In certain embodiments, the phosphoketolase enzyme is capable of catalyzing the conversion of xylulose 5-phosphate to glyceraldehyde 3-phosphate and acetyl phosphate. In other embodiments, the phosphoketolase enzyme is capable of catalyzing the conversion of fructose 6-phosphate to erythrose 4-phosphate and acetyl phosphate. Thus, without being bound by theory, the expression of phosphoketolase as set forth herein can result in an increase in the amount of acetyl phosphate produced from a carbohydrate source. This acetyl phosphate can be converted into acetyl-CoA which can then be utilized by the enzymatic activities of the MVA pathway to produces mevalonate, isoprenoid precursor molecules, isoprene and/or isoprenoids. Thus the amount of these compounds produced from a carbohydrate substrate may be increased. Alternatively, production of Acetyl-P and AcCoA can be increased without the increase being reflected in higher intracellular concentration. In certain embodiments, intracellular acetyl-P or acetyl-CoA concentrations will remain unchanged or even decrease, even though the phosphoketolase reaction is taking place.

Exemplary phosphoketolase nucleic acids include nucleic acids that encode a polypeptide, fragment of a polypeptide, peptide, or fusion polypeptide that has at least one activity of a phosphoketolase polypeptide. Exemplary phosphoketolase polypeptides and nucleic acids include naturally-occurring polypeptides and nucleic acids from any of the source organisms described herein as well as mutant polypeptides and nucleic acids derived from any of the source organisms described herein.

Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., J. Bact. 183: 2929-2936, 2001). Any polypeptide identified as having phosphoketolase peptide activity as described herein is suitable for use in the present invention.

In other aspects, exemplary phosphoketolase nucleic acids include, for example, a phosphoketolase isolated from *Lactobacillus reuteri, Bifidobacterium longum, Ferrimonas balearica, Pedobactor saltans, Streptomyces griseus*, and/or *Nocardiopsis dassonvillei*. Additional examples of phosphoketolase enzymes which can be used herein are described in U.S. Pat. No. 7,785,858 and WO 2011159853A1, both of which are incorporated by reference herein.

Pathways Involving the Entner-Doudoroff Pathway

The Entner-Doudoroff (ED) pathway is an alternative to the Emden-Meyerhoff-Parnass (EMP-glycolysis) pathway. Some organisms, like *E. coli*, harbor both the ED and EMP pathways, while others have only one or the other. *Bacillus subtilis* has only the EMP pathway, while *Zymomonas mobilis* has only the ED pathway (Peekhaus and Conway. 1998. J. Bact. 180:3495-3502; Stulke and Hillen. 2000. Annu. Rev. Microbiol. 54, 849-880; Dawes et al. 1966. Biochem. J. 98:795-803).

Phosphogluconate dehydratase (edd) removes one molecule of $H_2O$ from 6-phospho-D-gluconate to form 2-dehydro-3-deoxy-D-gluconate 6-phosphate, while 2-keto-3-deoxygluconate 6-phosphate aldolase (eda) catalyzes an aldol cleavage (Egan et al. 1992. J. Bact. 174:4638-4646). The two genes are in an operon.

Metabolites that can be directed into the phosphoketolase pathway can also be diverted into the ED pathway. To avoid metabolite loss to the ED-pathway, phosphogluconate dehydratase gene (e.g., the endogenous phosphogluconate dehydratase gene) and/or an 2-keto-3-deoxygluconate 6-phosphate aldolase gene (e.g., the endogenous 2-keto-3-deoxygluconate 6-phosphate aldolase gene) activity is attenuated. One way of achieving attenuation is by deleting phosphogluconate dehydratase (edd) and/or 2-keto-3-deoxygluconate 6-phosphate aldolase (eda). This can be accomplished by replacing one or both genes with a chloramphenicol or kanamycin cassette followed by looping out of the cassette. Without these enzymatic activities, more carbon can flux through the phosphoketolase enzyme, thus increasing the yield of mevalonate, isoprene or isoprenoids.

The activity of phosphogluconate dehydratase (edd) and/or 2-keto-3-deoxygluconate 6-phosphate aldolase (eda) can also be decreased by other molecular manipulations of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphogluconate dehydratase gene and/or the endogenous 2-keto-3-deoxygluconate 6-phosphate aldolase gene results in more carbon flux into the mevalonate dependent biosynthetic pathway in comparison to cells that do not have attenuated endogenous phosphogluconate dehydratase gene and/or endogenous acetate kinase2-keto-3-deoxygluconate 6-phosphate aldolase gene expression.

Pathways Involving the Oxidative Branch of the Pentose Phosphate Pathway

*E. coli* uses the pentose phosphate pathway to break down hexoses and pentoses and to provide cells with intermediates for various anabolic pathways. It is also a major producer of NADPH. The pentose phosphate pathway is composed from an oxidative branch (with enzymes like glucose 6-phosphate 1-dehydrogenase (zwf), 6-phosphogluconolactonase (pgl) or 6-phosphogluconate dehydrogenase (gnd)) and a non-oxidative branch (with enzymes such as transketolase (tktA), transaldolase (talA or talB), ribulose-5-phosphate-epimerase and (or) ribose-5-phosphate epimerase) (Sprenger. 1995. Arch. Microbiol. 164:324-330).

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase) expression can be modulated (e.g., increase enzyme activity) to allow more carbon to flux towards fructose 6-phosphate and xylulose 5-phosphate, thereby increasing the eventual production of mevalonate, isoprene and isoprenoids. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic constitutively high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into the mevalonate dependent biosynthetic pathway in comparison to cells that do not have increased expression of transketolase, transaldolase, ribulose-5-phosphate-epimerase and (or) ribose-5-phosphate epimerase.

Pathways Involving Phosphofructokinase

Phosphofructokinase is a crucial enzyme of glycolysis which catalyzes the phosphorylation of fructose 6-phosphate. *E. coli* has two isozymes encoded by pfkA and pfkB. Most of the phosphofructokinase activity in the cell is due to pfkA (Kotlarz et al. 1975 Biochim. Biophys. Acta 381:257-268).

In order to direct carbon towards the phosphoketolase enzyme, phosphofructokinase expression can be modulated (e.g., decrease enzyme activity) to allow more carbon to flux towards fructose 6-phosphate and xylulose 5-phosphate, thereby increasing the eventual production of mevalonate, isoprene and isoprenoids. Decrease of phosphofructokinase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of phosphofructokinase is modulated by decreasing the activity of an endogenous phosphofructokinase. This can be accomplished by replacing the endogenous phosphofructokinase gene promoter with a synthetic constitutively low expressing promoter. The gene encoding phosphofructokinase can also be deleted. The decrease of the activity of phosphofructokinase can result in more carbon flux into the mevalonate dependent biosynthetic pathway in comparison to cells that do not have decreased expression of phosphofructokinase.

Additional Host Cell Mutations

The invention also contemplates additional host cell mutations that increase carbon flux through the MVA pathway. By increasing the carbon flow, more isoprene can be produced. The recombinant cells comprising acetoacetyl-CoA synthase as described herein can also be engineered for increased carbon flux towards mevalonate production wherein the activity of one or more enzymes from the group consisting of: (a) citrate synthase, (b) phosphotransacetylase; (c) acetate kinase; (d) lactate dehydrogenase; (e) NADP-dependent malic enzyme, and; (f) pyruvate dehydrogenase is modulated.

Citrate Synthase Pathway

Citrate synthase catalyzes the condensation of oxaloacetate and acetyl-CoA to form citrate, a metabolite of the Tricarboxylic acid (TCA) cycle (Ner, S. et al. 1983. Biochemistry 22: 5243-5249; Bhayana, V. and Duckworth, H. 1984. Biochemistry 23: 2900-2905) (FIG. 5). In *E. coli*, this enzyme, encoded by gltA, behaves like a trimer of dimeric subunits. The hexameric form allows the enzyme to be allosterically regulated by NADH. This enzyme has been widely studied (Wiegand, G., and Remington, S. 1986. Annual Rev. Biophysics Biophys. Chem. 15: 97-117; Duckworth et al. 1987. Biochem Soc Symp. 54:83-92; Stockell, D. et al. 2003. J. Biol. Chem. 278: 35435-43; Maurus, R. et al. 2003. Biochemistry. 42:5555-5565). To avoid allosteric inhibition by NADH, replacement by or supplementation with the *Bacillus subtilis* NADH-insensitive citrate synthase has been considered (Underwood et al. 2002. Appl. Environ. Microbiol. 68:1071-1081; Sanchez et al. 2005. Met. Eng. 7:229-239).

The reaction catalyzed by citrate synthase is directly competing with the thiolase catalyzing the first step of the mevalonate pathway, as they both have acetyl-CoA as a substrate (Hedl et al. 2002. J. Bact. 184:2116-2121). Therefore, one of skill in the art can modulate citrate synthase expression (e.g., decrease enzyme activity) to allow more carbon to flux into the mevalonate pathway, thereby increasing the eventual production of mevalonate and isoprene. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis*. The activity of citrate synthase can also be modulated (e.g., decreased) by replacing the endogenous citrate synthase gene promoter with a synthetic constitutively low expressing promoter. The decrease of the activity of citrate synthase can result in more carbon flux into the mevalonate dependent biosynthetic pathway in comparison to microorganisms that do not have decreased expression of citrate synthase.

Pathways Involving Phosphotransacetylase and/or Acetate Kinase

Phosphotransacetylase (pta) (Shimizu et al. 1969. Biochim. Biophys. Acta 191: 550-558) catalyzes the reversible conversion between acetyl-CoA and acetylphosphate (acetyl-P), while acetate kinase (ackA) (Kakuda, H. et al. 1994. J. Biochem. 11:916-922) uses acetyl-P to form acetate. These genes can be transcribed as an operon in *E. coli*. Together, they catalyze the dissimilation of acetate, with the release of ATP. Thus, one of skill in the art can increase the amount of available acetyl Co-A by attenuating the activity of phosphotransacetylase gene (e.g., the endogenous phosphotransacetylase gene) and/or an acetate kinase gene (e.g., the endogenous acetate kinase gene). One way of achieving attenuation is by deleting phosphotransacetylase (pta) and/or acetate kinase (ackA). This can be accomplished by replacing one or both genes with a chloramphenicol cassette followed by looping out of the cassette. Acetate is produced by *E. coli* for a variety of reasons (Wolfe, A. 2005. Microb. Mol. Biol. Rev. 69:12-50). Without being bound by theory, since ackA-pta use acetyl-CoA, deleting those genes might allow carbon not to be diverted into acetate and to increase the yield of mevalonate and/or isoprene.

In some aspects, the recombinant microorganism produces decreased amounts of acetate in comparison to microorganisms that do not have attenuated endogenous phosphotransacetylase gene and/or endogenous acetate kinase gene expression. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of phosphotransacetylase (pta) and/or acetate kinase (ackA) can also be decreased by other molecular manipulation of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression. Pathways involving lactate dehydrogenase In *E. coli*, D-Lactate is produced from pyruvate through the enzyme lactate dehydrogenase (ldhA—FIG. 5) (Bunch, P. et al. 1997. Microbiol. 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevolnate production (and isopren production, if desired), one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant microorganism produces decreased amounts of lactate in comparison to microorganisms that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to microorganisms that do not have attenuated endogenous lactate dehydrogenase gene expression.

Pathways Involving Malic Enzyme

Malic enzyme (in *E. coli* sfcA and maeB) is an anaplerotic enzyme that catalyzes the conversion of malate into pyruvate (using NAD+ or NADP+) by the equation below:

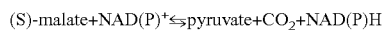

(S)-malate+NAD(P)$^+$⇌pyruvate+CO$_2$+NAD(P)H

Thus, the two substrates of this enzyme are (S)-malate and NAD(P)$^+$, whereas its 3 products are pyruvate, CO$_2$, and NADPH.

Expression of the NADP-dependent malic enzyme (maeB—FIG. 5) (Iwikura, M. et al. 1979. J. Biochem. 85: 1355-1365) can help increase mevalonate and/or isoprene yield by 1) bringing carbon from the TCA cycle back to pyruvate, direct precursor of acetyl-CoA, itself direct precursor of the mevalonate pathway and 2) producing extra NADPH which could be used in the HMG-CoA reductase reaction (Oh, M K et al. (2002) *J. Biol. Chem.* 277: 13175-13183; Bologna, F. et al. (2007) J. Bact. 189:5937-5946).

As such, more starting substrate (pyruvate or acetyl-CoA) for the downstream production of mevalonate and/or isoprene can be achieved by modulating, such as increasing, the activity and/or expression of malic enzyme. The NADP-dependent malic enzyme gene can be an endogenous gene. One non-limiting way to accomplish this is by replacing the endogenous NADP-dependent malic enzyme gene promoter with a synthetic constitutively expressing promoter. Another non-limiting way to increase enzyme activity is by using one or more heterologous nucleic acids encoding an NADP-dependent malic enzyme polypeptide. One of skill in the art can monitor the expression of maeB RNA during fermentation or culturing using readily available molecular biology techniques.

Accordingly, in some embodiments, the recombinant microorganism produces increased amounts of pyruvate in comparison to microorganisms that do not have increased expression of an NADP-dependent malic enzyme gene. In some aspects, increasing the activity of an NADP-dependent malic enzyme gene results in more carbon flux into the mevalonate dependent biosynthetic pathway in comparison to microorganisms that do not have increased NADP-dependent malic enzyme gene expression.

Increase in the amount of pyruvate produced can be measured by routine assays known to one of skill in the art. The amount of pyruvate increase can be at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of malic enzyme can also be increased by other molecular manipulations of the enzyme. The increase of enzyme activity can be any amount of increase of specific activity or total activity as compared to when no manipulation has been effectuated. In some instances, the increase of enzyme activity is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6 (aattcatataaaaaacatacagataaccatctgcgg tgataaat-tatctctggcggtgttgacataaataccactggcggtgatactgagcacatca gcaggacgcactgaccaccatgaaggtg-lambda promoter, GenBank NC_001416 (SEQ ID NO:10)), in front of the operon or using one or more synthetic constitutively expressing promoters.

Accordingly, in one aspect, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of these genes can be manipulated for increasing activity of pyruvate dehydrogenase. In another aspect, the activity of the pyruvate dehydrogenase complex can be modulated by attenuating the activity of an endogenous pyruvate dehydrogenase complex repressor gene, further detailed below. The activity of an endogenous pyruvate dehydrogenase complex repressor can be attenuated by deletion of the endogenous pyruvate dehydrogenase complex repressor gene.

In some cases, one or more genes of the pyruvate dehydrogenase complex are endogenous genes. Another way to increase the activity of the pyruvate dehydrogenase complex is by introducing into the microorganism one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant microorganism can produce increased amounts of acetyl Co-A in comparison to microorganisms wherein the activity of pyruvate dehydrogenase is not modulated. Modulating the activity of pyruvate dehydrogenase can result in more carbon flux into the mevalonate dependent biosynthetic pathway in comparison to microorganisms that do not have modulated pyruvate dehydrogenase expression.

Combinations of Mutations

It is understood that for any of the enzymes and/or enzyme pathways described herein, molecular manipulations that modulate any combination (two, three, four, five or six) of the enzymes and/or enzyme pathways described herein is expressly contemplated. For ease of the recitation of the combinations, citrate synthase (gltA) is designated as A, phosphotransacetylase (ptaB) is designated as B, acetate kinase (ackA) is designated as C, lactate dehydrogenase (ldhA) is designated as D, malic enzyme (sfcA or maeB) is designated as E, and pyruvate decarboxylase (aceE, aceF, and/or lpdA) is designated as F. As discussed above, aceE, aceF, and/or lpdA enzymes of the pyruvate decarboxylase complex can be used singly, or two of three enzymes, or three of three enzymes for increasing pyruvate decarboxylase activity.

Accordingly, for combinations of any two of the enzymes A-F, non-limiting combinations that can be used are: AB, AC, AD, AE, AF, BC, BD, BE, BF, CD, CE, CF, DE, DF and EF. For combinations of any three of the enzymes A-F, non-limiting combinations that can be used are: ABC, ABD, ABE, ABF, BCD, BCE, BCF, CDE, CDF, DEF, ACD, ACE, ACF, ADE, ADF, AEF, BDE, BDF, BEF, and CEF. For combinations of any four of the enzymes A-F, non-limiting combinations that can be used are: ABCD, ABCE, ABCF, ABDE, ABDF, ABEF, BCDE, BCDF, CDEF, ACDE, ACDF, ACEF, BCEF, BDEF, and ADEF. For combinations of any five of the enzymes A-F, non-limiting combinations that can be used are: ABCDE, ABCDF, ABDEF, BCDEF, ACDEF, and ABCEF. In another aspect, all six enzyme combinations are used: ABCDEF.

Accordingly, the recombinant microorganism as described herein can achieve increased mevalonate production that is increased compared to microorganisms that are not grown under conditions of tri-carboxylic acid (TCA) cycle activity, wherein metabolic carbon flux in the recombinant microorganism is directed towards mevalonate production by modulating the activity of one or more enzymes from the group consisting of (a) citrate synthase, (b) phosphotransacetylase and/or acetate kinase, (c) lactate dehydrogenase, (d) malic enzyme, and (e) pyruvate decarboxylase complex.

Other Regulators and Factors for Increased Isoprene Production

Other molecular manipulations can be used to increase the flow of carbon towards isoprene production. One method is to reduce, decrease or eliminate the effects of negative regulators for pathways that feed into the mevalonate pathway. For example, in some cases, the genes aceEF-lpdA are in an operon, with a fourth gene upstream pdhR. pdhR is a negative regulator of the transcription of its operon. In the absence of pyruvate, it binds its target promoter and represses transcription. It also regulates ndh and cyoABCD in the same way (Ogasawara, H. et al. 2007. J. Bact. 189:5534-5541). In one aspect, deletion of pdhR regulator can improve the supply of pyruvate, and hence the production mevalonate and/or isoprene.

In other aspects, the introduction of 6-phosphogluconolactonase (PGL) into microorganisms (such as various *E. coli* strains) which lack PGL can be used to improve production of mevalonate and/or isoprene. PGL may be introduced using chromosomal integration or extrachromosomal vehicles, such as plasmids. In other aspects, PGL may be deleted from the genome of microorganisms (such as various *E. coli* strains) which express an endogenous PGL to improve production of mevalonate and/or isoprene. In some aspects, deletion of PGL results in any of about 10%, 20%, 30%, 40%, 50%, 60%, 70%, 80%, 90%, or 100%, inclusive, including any values in between these percentages, higher percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher instantaneous percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher cell productivity index for isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher volumetric productivity of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher peak specific productivity of isoprene in comparison to microorganisms that express PGL. In some aspects the deletion of PGL results in peak specific productivity being maintained for a longer period of time in comparison to microorganisms that express PGL.

Recombinant Cells with IspA Manipulations

Isoprene can also be made using recombinant cells that have been engineered to downregulate the expression or functional activity of the ispA gene during precise time periods during fermentation. The aspect is based on the observation that decreased expression of the ispA gene of recombinant cells during fermentation results in higher levels of isoprene production in comparison to cells that do not possess decreased ispA gene functional activity. Without being bound to theory, it is believed that decreasing ispA gene expression and/or functional activity improves isoprene yields by decreasing the production and accumulation of higher molecular weight isoprenoid molecules thereby resulting in higher carbon availability for isoprene synthesis as well as improved cell viability. However, because the ispA gene produces an enzyme that is essential for the robust growth of bacteria and other microorganisms, total elimination of this gene, such as through a gene knock out, is not a practical option for improving isoprene yields as it has been reported to result in either impaired growth (Fukisaki et al., 2005, *J. Biochem.*, 137(3):395-400) or in the death (worldwide web-.genome.wisc.edu/resources/essential.htm; Baba et al., 2006, *Mol. Syst. Biol.*, 2006.0008) of the cells. Accordingly, in one aspect, one of skill in the art can utilize specific and temporally-precise decreased expression and/or functional activity of the ispA gene during isoprene production (e.g. subsequent to the linear growth phase of fermentation) to achieve higher isoprene yield, titer, cell productivity, volumetric productivity, specific productivity, and cell viability by the recombinant cells.

Thus, in some embodiments, the recombinant cells comprise an ispA having decreased functional activity. In one aspect, the functional activity of ispA is decreased only during the fermentation (or production) phase of cell culture. In another aspect, the functional activity of ispA is not decreased during the linear growth phase during cell culture. In some aspects, the functional activity of ispA is decreased in both the growth and fermentation phases of cell culture. In yet another aspect, the functional activity of ispA is decreased in both the growth and fermentation phases of cell culture, but the decrease is larger in the fermentation phase. Any method can be used to decrease the functional activity of ispA, such as, but not limited to, deleting the ispA gene, decreasing ispA gene expression, or decreasing the activity or availability of the polypeptide encoded by the ispA gene. In other aspects, the recombinant cells of the present invention comprise an ispA having decreased functional activity and one or more of a group of genes involved in isoprene biosynthesis that enables the synthesis of isoprene in the host microorganism. In another aspect, the recombinant host cells of the present invention comprise a recombinant ispA gene that has been codon optimized for expression in host cells. In some aspects, the codon optimized ispA gene is integrated into the host cell genome. In other aspects, the codon optimized ispA gene is expressed on a piece of extrachromosomal DNA (such as a plasmid). In another aspect, the codon optimized ispA gene is integrated into the host cell genome at the yhfS locus and the endogenous ispA gene is deleted.

In some aspects, the recombinant host cells of the present invention comprise a recombinant ispA gene that encodes a FPP synthase with an increased Km value (for example, an avian FPP synthase) for DMAPP in comparison to the Km value for DMAPP exhibited by the endogenously encoded FPP synthase. Such high Km FPP synthases have been described, for example, in Fernandez et al., *Biochemistry*, 2000, 39(50):15316-21. In other aspects, the recombinant host cells of the present invention can comprise a thermophilic FPP synthase (such as the FPP synthase described in Koyama et al., *J. Biochem.*, 113:355-363), a psychrophilic FPP synthase (such as the FPP synthase described in Nichols et al., 2004, *J. Bact.*, 186:8508-8515, the contents of which is incorporated by reference herein in its entirety), or an FPP synthase from a marine prokaryote (such as the FPP synthase described in Ranzer et al., 2009, *Mar. Biotechnol*, 11:62-73). In some aspects, the endogenous host cell ispA gene in any of the recombinant cells described herein is replaced by any of the alternative genes encoding an FPP synthase described herein.

In some aspects, the recombinant host cells of the present invention comprise an ispA gene under the control of a weak promoter (i.e., a promoter driving the expression of an ispA gene, wherein the amount of expression is less than what is observed by the endogenous or wild type ispA promoter). In some aspects, the promoter controlling the expression of the ispA gene expresses the ispA gene at a higher level during the linear growth phase during cell culture in comparison to the expression of the ispA gene during the fermentation phase.

Decreased Functional Activity of ispA

In some aspects, the recombinant cells described herein comprise an ispA having decreased functional activity.

"Decreased functional activity" in this context refers to the ability of an ispA polypeptide (for example, a polypeptide encoded by an ispA gene) to convert IPP and DMAPP to GPP and/or FPP (i.e., the molecules necessary for subsequent production of isoprenoids). In some aspects, any of the recombinant cells disclosed herein can comprise an ispA gene wherein functional activity of ispA is decreased such that the cells produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in cells that do not comprise an ispA having decreased functional activity. In another aspect, recombinant cells that have been engineered to produce isoprene comprising one or more heterologous nucleic acids encoding one or members of the MVA pathway and an ispA having decreased functional activity produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in recombinant cells that comprise one or more heterologous nucleic acids encoding one or more members of the MVA pathway but that do not comprise an ispA having decreased functional activity. In other aspects, any of the recombinant cells disclosed herein can comprise ispA wherein functional activity of ispA is decreased such that the cells produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of isoprenoids in comparison to the concentration of these molecules in cells that do not comprise ispA having decreased functional activity. In other aspects, any of the recombinant cells disclosed herein can comprise ispA wherein functional activity of the ispA gene is decreased such that the cells exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that do not comprise ispA having decreased functional activity. In another aspect, recombinant cells that have been engineered to produce isoprene comprising one or more heterologous nucleic acids encoding one or members of the MVA pathway and an ispA having decreased functional activity can exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that comprise one or more heterologous nucleic acids encoding one or more members of the MVA pathway but that do not comprise an ispA having decreased functional activity. As used herein, "improved viability" means there are less dead, dying, or otherwise morphologically abnormal cells produced during the course of fermentation. Morphological abnormalities can include, but are not limited to, elongated cells and/or cellular debris from dead or dying cells. In some embodiments, "improved viability" can mean that a greater number of cells are determined to be alive through a cell biological, molecular biological, or biochemical technique that is known in the art (such as, but not limited to, Fluorescent Activated Cell Sorting (FACS) or DiBAC4(3) staining). In some aspects, ispA functional activity is decreased during the peak isoprene production phase of fermentation. In other aspects, ispA functional activity is not decreased during the linear growth phase of fermentation.

Methods to measure decreased functional activity of ispA are many and well known in the art. For example, standard methods can be used to determine the production of metabolites (for example, FPP and GPP) in cells, such as by the chemical extraction of metabolites from whole cells followed by identification via mass spectrometry. Similarly, standard methods can be used to assay viability of cells with decreased ispA functional activity such as morphological analysis by microscopy or by assessing membrane potential. Cells with intact membrane potential are assumed to be alive and metabolically active, while cells with no membrane potential were assumed to be dead and metabolically inactive.

Decreased Expression of the ispA Gene

In some aspects, the functional activity of the ispA gene is decreased by decreasing the expression of the ispA gene. This can include deleting the ispA gene itself, either in whole or in part, or by decreasing its expression through any number of methods as described herein. Temporally-regulated decreased expression via auto-regulatory promoters In some aspects, ispA gene expression is decreased by placing the ispA gene under the control of an auto-regulatory promoter. In certain embodiments, promoters which are repressed only during late stage fermentation of recombinant cells that have been engineered to produce increased levels of isoprene can be used to decrease the functional activity of the ispA gene. Without being bound to theory, it is hypothesized that such promoters are repressed during periods of increased accumulation of isoprenoid compounds as fermentation progresses. Therefore, placing the ispA gene under the control of these promoters can be used to temporally control the expression of ispA, such that ispA repression occurs at time periods which correspond to increased flux through the isoprenoid pathway. However, at time periods where the isoprenoid pathway flux is low, such as during the linear growth phase of fermentation, then the promoter will remain induced and thereby permit expression of the ispA gene. This signature activity profile constitutes an auto-regulatory ispA expression control system.

Accordingly, in some aspects, any of the recombinant cells described herein can comprise an ispA gene having decreased functional activity, wherein the functional activity of the ispA gene is decreased by placing the ispA gene under the control of an auto-regulatory promoter. In some aspects, the auto-regulatory promoter is selected from the group consisting of: efeO, kpsC, kpsD, kpsD, kpsE, kpsF, kpsS, kpsU, nmpC, sodA, ybl129, ybl130, ybl131, yddV, and ydiU. In one aspect, the ispA gene is placed under control of the yddV promoter. In other aspects, the endogenous ispA gene can be deleted from the genome of the recombinant cell (for example, a recombinant E. coli cell) and a new ispA gene can be substituted into the genome at a different locus. In one aspect, a heterologous ispA gene is inserted into the genome of the recombinant cell (for example, a recombinant E. coli cell) at the yhfS locus. The heterologous ispA gene can be identical to the deleted endogenous ispA gene or be an ispA gene from another source. In other aspects, the heterologous ispA gene under control of an auto-regulatory promoter is expressed extrachromosomally. In another aspect, the recombinant host cells of the present invention comprise a recombinant ispA gene that has been codon optimized for expression in host cells. In some aspects, the codon optimized ispA gene is integrated into the host cell genome. In another aspect, the codon optimized ispA gene is under the control of an auto-regulatory promoter selected from the group consisting of: efeO, kpsC, kpsD, kpsD, kpsE, kpsF, kpsS, kpsU, nmpC, sodA, ybl129, ybl130, ybl131, yddV, and ydiU. In some aspects, the codon optimized ispA gene is under the control of the yddV promoter. In yet another aspect, any of the auto-regulatory promoters described herein can drive the expression of an ispA gene selected from the group consisting of: a codon-optimized ispA, an ispA allele (for example, an avian ispA allele) encoding an enzyme comprising a Km that is higher in comparison to ispA-encoded enzymes from microorganisms, and an endogenous ispA allele.

In some aspects, recombinant cells (such as any of the recombinant cells disclosed herein) expressing an ispA gene under the control of an auto-regulatory promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in cells that do not comprise an ispA gene under the control of an auto-regulatory promoter. In another aspect, recombinant cells that have been engineered to produce isoprene comprising one or more heterologous nucleic acids encoding one or members of the MVA pathway and an ispA gene under the control of an auto-regulatory promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in recombinant cells that comprise one or more heterologous nucleic acids encoding one or more members of the MVA pathway but that do not comprise an ispA gene under the control of an auto-regulatory promoter. In some aspects, recombinant cells (such as any of the recombinant cells disclosed herein) expressing an ispA gene under the control of an auto-regulatory promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of isoprenoids in comparison to the concentration of these molecules in cells that do not comprise an ispA gene under the control of an auto-regulatory promoter. In other aspects, recombinant cells (such as any of the recombinant cells disclosed herein) expressing an ispA gene under the control of an auto-regulatory promoter exhibit any of 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that do not comprise an ispA gene under the control of an auto-regulatory promoter. In another aspect, recombinant cells that have been engineered to produce isoprene comprising one or more heterologous nucleic acids encoding one or members of the MVA pathway and an ispA gene under the control of an auto-regulatory promoter can exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that comprise one or more heterologous nucleic acids encoding one or more members of the MVA pathway but that do not comprise an ispA gene under the control of an auto-regulatory promoter.

Temporally-Regulated Decreased Expression Via the Heterologous Repressor Protein HrcA An alternate method to control expression of ispA utilizes the transcriptional repressor protein HrcA of *Caulobacter crescentus* (Roberts et al., *Journal of Bacteriology*, 1996, 178:7, 1829-41; Susin et al., *Journal of Bacteriology*, 2004, 186:20, 6759-67). The gene encoding HrcA is not naturally found in *E. coli* and there is no known information suggesting that the CIRCE element, which is recognized by HrcA, is involved in governing *E. coli* gene expression. Therefore, incorporating the CIRCE element within the regulatory sequence governing ispA expression within an *E. coli* isoprene producing system would permit HrcA-mediated repression of ispA. In addition, the heterologous hrcA gene can be introduced into an *E. coli* isoprene-producing host where its expression can be governed by at least one of a number of tightly regulated means Therefore, in some aspects, any of the recombinant cells described herein can comprise an ispA gene having decreased functional activity, wherein the functional activity of the ispA gene is decreased by an HrcA transcriptional repressor protein encoded by an hrcA gene and wherein a CIRCE element is engineered into a regulatory sequence governing ispA expression. In some aspects, hrcA expression is controlled by a linear growth phase regulated promoter identified within the transcriptional profile of cells across a large scale isoprene-generating fermentation. In some aspects, the linear growth phase regulated promoter is selected from the group consisting of otsA, amiB, and deoC.

In other aspects, hrcA expression may be controlled by a positive regulatory-loop that is itself turned on during the desired slow growth phase of fermentation via an inducing signal, such as acute nutrient limitation or altered temperature. In this aspect, a transactivator peptide, such as transactivator T, is functionally linked to a particular signal-sensing promoter. Introduction of the inducing signal will induce activity of the signal-sensing promoter, which, in turn, upregulates the expression of transactivator T. By linking further copies of transactivator T genes to transactivator T-dependent promoters a positive feedback loop is initiated and sustained once the inducing signal is removed. In other aspects, the hrcA gene is linked to at least one transactivator T-dependent promoter resulting in HrcA being continually expressed during periods subsequent to activation of the positive regulatory loop. In certain aspects, the transactivator T gene driven by transactivator T dependent promoter is located on the same operon as the hrcA gene. In other aspects, the transactivator T gene driven by transactivator T dependent promoters is located in an independent locus not containing the hrcA gene.

In some aspects, recombinant cells (such as any of the recombinant cells disclosed herein) expressing an ispA gene under the control of an HrcA repressor protein produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in cells that do not comprise an ispA gene under the control of an HrcA repressor protein. In another aspect, recombinant cells that have been engineered to produce isoprene comprising one or more heterologous nucleic acids encoding one or members of the MVA pathway and an ispA gene under the control of an HrcA repressor protein produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in recombinant cells that comprise one or more heterologous nucleic acids encoding one or more members of the MVA pathway but that do not comprise an ispA gene under the control of an HrcA repressor protein. In some aspects, recombinant cells (such as any of the recombinant cells disclosed herein) expressing an ispA gene under the control of an HrcA repressor protein produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of isoprenoids in comparison to the concentration of these molecules in cells that do not comprise an ispA gene under the control of an HrcA repressor protein. In other aspects, recombinant cells (such as any of the recombinant cells disclosed herein) expressing an ispA gene under the control of an HrcA repressor protein exhibit any of 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that do not comprise an ispA gene under the control of an HrcA repressor protein. In another aspect, recombinant cells that have been engineered to produce isoprene comprising one or more heterologous nucleic acids encoding one or members of the MVA pathway and an ispA gene under the control of an HrcA repressor protein can exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that comprise one or more heterologous nucleic acids encoding one or more members of the MVA pathway but that do not comprise an ispA gene under the control of an HrcA repressor protein.

Temporally-Regulated Decreased Expression Via Xylose-Regulated Expression of ispA Regulated gene expression mediated by carbon source availability is another scalable alternative to controlling ispA gene expression within a production host (for example, an *E. coli* production host). Such a method offers the ability to provide relatively normal and/or sufficient levels of ispA gene expression required for healthy robust fast growing cells, allowing quick biomass placement. In addition, such a method offers the ability to restrict expression of ispA during glucose-supported isoprene production when FPP synthase activity is believed to be detrimental to cell viability, resulting in reduced yield of isoprene produced from glucose.

Consequently, in some aspects, any of the recombinant cells described herein can comprise an ispA gene having decreased functional activity, wherein the functional activity of the ispA gene is decreased by placing the ispA gene under direct control of a xylose-regulated promoter. In some aspects, ispA expression in recombinant cell (such as a recombinant *E. coli* cell) is placed under the direct control of an endogenous xylA or xylF promoters or under control of any promoter that is positively influence by D-xylose and negatively influenced by glucose within the recombinant cell. This is accomplished by deleting the endogenous ispA gene and substituting a heterologous ispA under the control of either the xylA or xylF D-xylose-responsive promoters. The divergent xylA-xylF promoters of *E. coli* and their positive regulation via D-xylose and the transcriptional activator XylR as well as their negative regulation by glucose and catabolite repression have been described (S. Song and C. Park *J. Bacteriol.* 1997, 179(22):7025-7032). In some aspects, ispA gene expression is governed positively by the availability of xylose in the absence of glucose and negatively by the presence of glucose. In some aspects, the xylose-inducible ispA locus is present within the chromosome of the recombinant cell (such as a recombinant *E. coli* cell), but, alternatively, may also be encoded on an extrachromosomal nucleotide sequence such as a plasmid. Construction of the xylose-inducible ispA construct and its introduction into the isoprene producing *E. coli* host can be performed using standard molecular and microbiology techniques (J. Sambrook, E. F. Fritsch, and T. Maniatis Cold Spring Harbor Laboratory Press, NY. 1989).

In some aspects, recombinant cells (such as any of the recombinant cells disclosed herein) expressing an ispA gene under the control of an xylose-inducible promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in cells that do not comprise an ispA gene under the control of an xylose-inducible promoter. In another aspect, recombinant cells that have been engineered to produce isoprene comprising one or more heterologous nucleic acids encoding one or members of the MVA pathway and an ispA gene under the control of an xylose-inducible promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in recombinant cells that comprise one or more heterologous nucleic acids encoding one or more members of the MVA pathway but that do not comprise an ispA gene under the control of an xylose-inducible promoter. In some aspects, recombinant cells (such as any of the recombinant cells disclosed herein) expressing an ispA gene under the control of an xylose-inducible promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of isoprenoids in comparison to the concentration of these molecules in cells that do not comprise an ispA gene under the control of an xylose-inducible promoter. In other aspects, recombinant cells (such as any of the recombinant cells disclosed herein) expressing an ispA gene under the control of an xylose-inducible promoter exhibit any of 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that do not comprise an ispA gene under the control of an xylose-inducible promoter. In another aspect, recombinant cells that have been engineered to produce isoprene comprising one or more heterologous nucleic acids encoding one or members of the MVA pathway and an ispA gene under the control of an xylose-inducible promoter can exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that comprise one or more heterologous nucleic acids encoding one or more members of the MVA pathway but that do not comprise an ispA gene under the control of an xylose-inducible promoter.

Decreased FPP Synthase Activity

In some aspects, the functional activity of the ispA gene is decreased by decreasing the activity of the IspA protein, FPP synthase. This can include inhibiting the translation of the IspA mRNA or by degrading FPP synthase itself through any number of methods as described herein.

Translational Fusion of the IspA Protein with a Proteolytic Tag

In some aspects of any of the recombinant cells described herein, FPP synthase is targeted for proteolytic degradation by engineering a DNA sequence into the ispA gene which encodes an 11 amino acid protein tag (Andersen et al., *Appl Environ Microbiol.*, 1998, 64(6), 2240-46). The proteolytic tmRNA tag then targets FPP synthase for degradation in host cells. In some aspects, the proteolytic tag is fused to the C-terminus of the FPP synthase protein. In other aspects, the proteolytic tag is fused to the N-terminus of the FPP synthase protein.

In some aspects, recombinant cells (such as any of the recombinant cells disclosed herein) expressing an FPP synthase protein fused to a proteolytic tag produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in cells that do not comprise an FPP synthase protein fused to a proteolytic tag. In another aspect, recombinant cells (such as any of the recombinant cells disclosed herein) expressing an FPP synthase protein fused to a proteolytic tag that have been engineered to produce isoprene comprising one or more heterologous nucleic acids encoding one or members of the MVA pathway produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in recombinant cells that comprise one or more heterologous nucleic acids encoding one or more members of the MVA pathway but do not comprise an FPP synthase protein fused to a proteolytic tag. In some aspects, recombinant cells (such as any of the recombinant cells disclosed herein) expressing an FPP synthase protein fused to a proteolytic tag produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of isoprenoids in comparison to the concentration of these molecules in cells that do not comprise an FPP synthase protein fused to a proteolytic tag. In other aspects, recombinant cells (such as any of the recombinant cells disclosed herein) expressing an FPP synthase protein fused to a proteolytic tag exhibit any of 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that do not comprise an IspA protein fused to a proteolytic tag. In another aspect, recombinant cells (such as any of the recombinant cells disclosed herein) expressing an FPP synthase protein fused to a proteolytic tag comprising one or more heterologous nucleic acids encoding one or members of the MVA pathway and an ispA gene can exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that comprise one or more heterologous nucleic acids encoding one or more members of the MVA pathway but that do not comprise an FPP synthase protein fused to a proteolytic tag.

Decreased IspA Protein Expression Via the Use of Antisense mRNA and Ribosomal Binding Mutations In some aspects, antisense mRNA directed towards ispA mRNA is used to prevent the translation of ispA mRNA into IspA protein and result in decreased IspA protein activity. Antisense is well known in the art and has been used in *E. coli*, among other organisms, to reduce the production of molecules such as acetate (Kim J. and Cha H. J., *Biotech Bioeng.*, 2003, 83:841-853) or to engineer a catalase knockout phenotype (Chan E. et al., *J. Exp. Microbiol Immunol.*, 2010, 14:127-134). Design of antisense constructs targeted to the ispA gene of *E. coli* can be prepared using methods described by Shao Y. et al., *Nucleic Acids Res.*, 2006, 34:5660-5669. The antisense RNA molecules can be stabilized using paired termini (Nakashima N. et al., *Nucleic Acids Res.*, 2006, 34: e138). In some aspects, the antisense oligonucleotide is about 150 bp long. Decreased translation of ispA mRNA due to antisense mRNA treatment can be measured by any means known in the art including, but not limited to, enzyme activity assays, Western Blot, Northern Blot, or RT-PCR.

In other aspects, IspA protein activity is decreased through the introduction of one or more mutations into one or more ribosomal binding sites located in the ispA mRNA molecule. Introduction of ribosomal-binding mutations interferes or abolishes the translation of the IspA mRNA leading to decreased IspA protein activity. Decreased translation of ispA mRNA due to the introduction of one or more mutations into one or more ribosomal binding sites located in the ispA mRNA molecule can be measured by any means known in the art including, but not limited to, enzyme activity assays or Western Blot.

Exemplary Host Cells

One of skill in the art will recognize that expression vectors are designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Any microorganism or progeny thereof can be used to express any of the genes (heterologous or endogenous) described herein. Bacteria cells, including gram positive or gram negative bacteria can be used to express any of the genes described herein. In particular, the genes described herein can be expressed in any one of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *Corynebacteria* sp., *P. alcaligenes*, and *L. acidophilus* cells.

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce isoprene can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce isoprene. Facultative anaerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, *Biotechnology Advances*, (1989), 7(2):127-154). In some aspects, the filamentous fungal cell can be any of *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A. sojae, A. japonicus, A. nidulans*, or *A. awamori, Fusarium* sp., such as *F. roseum, F. graminum F. cerealis, F. oxysporuim*, or *F. venenatum, Neurospora* sp., such as *N. crassa, Hypocrea* sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T. reesei, T. viride, F. oxysporum*, or *F. solani*. In certain embodiments, plasmids or plasmid components for use herein include those described in U.S. patent pub. No. US 2011/0045563.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., *Yeast*, (1992), 8(6):423-488). In certain embodiments, plasmids or plasmid components for use herein include those described in U.S. Pat. No. 7,659,097 and U.S. patent pub. No. US 2011/0045563.

The host cell can additionally be a species of algae, such as a green algae, red algae, glaucophytes, chlorarachniophytes, euglenids, chromista, or dinoflagellates. (See, e.g., Saunders & Warmbrodt, *"Gene Expression in Algae and Fungi, Including Yeast,"* (1993), National Agricultural Library, Beltsville, Md.). In certain embodiments, plasmids or plasmid components for use herein include those described in U.S. Patent Pub. No. US 2011/0045563. In some aspects, the host cell is a cyanobacterium, such as cyanobacterium classified into any of the following groups based on morphology: Chlorococcales, Pleurocapsales, Oscillatoriales, Nostocales, or Stigonematales (See, e.g., Lindberg et al., *Metab. Eng.*, (2010) 12(1):70-79). In certain embodiments, plasmids or plasmid components for use herein include those described in U.S. patent pub. No. US 2010/0297749; US 2009/0282545 and Intl. Pat. Appl. No. WO 2011/034863.

*E. coli* cells can be used as a host cell in the compositions and methods described herein. In one aspect, the host cell is a recombinant cell of an *Escherichia coli* (*E. coli*) strain, or progeny thereof, capable of producing mevalonate that expresses one or more heterologous nucleic acids described herein. In other aspects, the *E. coli* cells are in culture.

Vectors

Suitable vectors can be used for any of the compositions and methods described herein. For example, suitable vectors can be used to optimize the expression of one or more copies of a gene encoding a HMG-CoA reductase, an isoprene synthase, and/or one or more non-thiolase MVA pathway polypeptides. In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some aspects, one or more copies of HMG-CoA reductase, an isoprene synthase, and/or one or more non-thiolase MVA pathway polypeptides nucleic acid(s) integrate into the genome of host cells without a selective marker. Any one of the vectors characterized or used in the Examples of the present disclosure can be used.

Transformation Methods

Nucleic acids encoding acetoacetyl-CoA synthase, an enzyme that produces acetoacetyl-CoA synthase from malonyl-CoA and acetyl-CoA, non-thiolase MVA pathway polypeptides, DXP pathway polypeptides, isoprene synthase polypeptides, IDI, and any other enzyme needed to produce isoprene can be introduced into host cells (e.g., a plant cell, a fungal cell, a yeast cell, or a bacterial cell) by any technique known to one of the skill in the art.

Standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion can be used. General transformation techniques are known in the art (See, e.g., *Current Protocols in Molecular Biology* (F. M. Ausubel et al. (eds.) Chapter 9, 1987; Sambrook et al., *Molecular Cloning: A Laboratory Manual*, 3r$^d$ ed., Cold Spring Harbor, 2001; and Campbell et al., *Curr. Genet.* 16:53-56, 1989). The introduced nucleic acids can be integrated into chromosomal DNA or maintained as extrachromosomal replicating sequences. Transformants can be selected by any method known in the art. Suitable methods for selecting transformants are described in International Publication No. WO 2009/076676, U.S. patent application Ser. No. 12/335,071 (US Publ. No. 2009/0203102), WO 2010/003007, U.S. Patent Appl. Publ. No. 2010/0048964, WO 2009/132220, and U.S. Patent Appl. Publ. No. 2010/0003716.

In one embodiment, a bacterium such as *Escherichia coli* is used as a host. In this embodiment, an expression vector can be selected and/or engineered to be able to autonomously replicate in such bacterium. Promoters, a ribosome binding sequence, transcription termination sequence(s) can also be included in the expression vector, in addition to the genes listed herein. Optionally, an expression vector may contain a gene that controls promoter activity.

Any promoter may be used as long as it can be expressed in a host such as *Escherichia coli*. Examples of such promoter that can be used include a trp promoter, an lac promoter, a PL promoter, a PR promoter, and the like from *Escherichia coli*, and a T7 promoter from a phage. Further, an artificially designed or modified promoter such as a tac promoter may be used.

A method for introduction of an expression vector is not particularly limited as long as DNA is introduced into a bacterium thereby. Examples thereof include a method using calcium ions (Cohen, S, N., et al.: *Proc. Natl. Acad. Sci., USA*, 69:2110-2114 (1972) and an electroporation method.

When a yeast is used as a host, *Saccharomyces cerevisiae, Schizosaccharomyces pombe, Pichia pastoris*, or the like can be used. In this case, a promoter is not particularly limited as long as it can be expressed in yeast. Examples thereof include a gall promoter, a gal10 promoter, a heat-shock protein promoter, an MF.alpha.1 promoter, a PHO5 promoter, a PGK promoter, a GAP promoter, an ADH promoter, and an AOX1 promoter.

A method for introducing a recombinant vector into yeast is not particularly limited as long as DNA is introduced into yeast thereby. Examples thereof include the electroporation method (Becker, D. M., et al. *Methods. Enzymol.*, 194: 182-187 (1990)), the spheroplast method (Hinnen, A. et al.: *Proc. Natl. Acad. Sci., USA*, 75: 1929-1933 (1978)), and the lithium acetate method (Itoh, H.: *J. Bacteriol.*, 153: 163-168 (1983)).

Exemplary Cell Culture Media

As used herein, the terms "minimal medium" or "minimal media" refer to growth medium containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for bacterial growth; (2) various salts, which can vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 ml sterile M9 salts (64 g $Na_2HPO_4$-$7H_2O$, 15 g $KH_2PO_4$, 2.5 g NaCl, and 5.0 g $NH_4Cl$ per liter); (2) 2 ml of 1 M $MgSO_4$ (sterile); (3) 20 ml of 20% (w/v) glucose (or other carbon source); and (4) 100 µl of 1 M $CaCl_2$ (sterile). Each liter of TM3 minimal medium contains (1) 13.6 g $K_2HPO_4$; (2) 13.6 g $KH_2PO_4$; (3) 2 g $MgSO_4.7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 ml of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4*H_2O$; (3) 10 g NaCl; (4) 1 g $FeSO_4*7H_2O$; (4) 1 g $CoCl_2*6H_2O$; (5) 1 g $ZnSO_4*7H_2O$; (6) 100 mg $CuSO_4*5H_2O$; (7) 100 mg $H_3BO_3$; and (8) 100 mg $NaMoO_4*2H_2O$; pH is adjusted to ~3.0.

An additional exemplary minimal media includes (1) potassium phosphate $K_2HPO_4$, (2) Magnesium Sulfate $MgSO_4*7H_2O$, (3) citric acid monohydrate $C_6H_8O_7*H_2O$, (4) ferric ammonium citrate $NH_4FeC_6H_5O_7$, (5) yeast extract (from biospringer), (6) 1000× Modified Trace Metal Solution, (7) sulfuric acid 50% w/v, (8) foamblast 882 (Emerald Performance Materials), and (9) Macro Salts Solution 3.36 ml All of the components are added together and dissolved in deionized $H_2O$ and then heat sterilized. Following cooling to room temperature, the pH is adjusted to 7.0 with ammonium hydroxide (28%) and q.s. to volume. Vitamin Solution and spectinomycin are added after sterilization and pH adjustment.

Any carbon source can be used to cultivate the host cells. The term "carbon source" refers to one or more carbon-containing compounds capable of being metabolized by a host cell or organism. For example, the cell medium used to cultivate the host cells can include any carbon source suitable for maintaining the viability or growing the host cells. In some aspects, the carbon source is a carbohydrate (such as monosaccharide, disaccharide, oligosaccharide, or polysaccharides), or invert sugar (e.g., enzymatically treated sucrose syrup). In one aspect, the host cells are initially cultured in a medium (such as a TM3 medium) containing D-xylose as a carbon source during the linear growth phase of fermentation. In another aspect, the carbon source is changed from D-xylose to glucose once the host cells reach the isoprene-production phase of fermentation.

In some aspects, the carbon source includes yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the carbon source includes both yeast extract (or one or more components thereof) and another carbon source, such as glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose).

Exemplary Cell Culture Conditions

Materials and methods suitable for the maintenance and growth of the recombinant cells of the invention are described infra, e.g., in the Examples section. Other materials and methods suitable for the maintenance and growth of bacterial cultures are well known in the art. Exemplary techniques can be found in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716, *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass. In some aspects, the cells are cultured in a culture medium under conditions permitting the expression of one or more isoprene synthase, one or more DXP pathway polypeptides, one or more MVA pathway polypeptides, IDI, or PGL polypeptides encoded by a nucleic acid inserted into the host cells.

Standard cell culture conditions can be used to culture the cells (see, for example, WO 2004/033646 and references cited therein). In some aspects, cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, the pH ranges for fermentation are between about pH 5.0 to about pH 9.0 (such as about pH 6.0 to about pH 8.0 or about 6.5 to about 7.0). Cells can be grown under aerobic conditions based on the requirements of the host cells. In addition, more specific cell culture conditions can be used to culture the cells. For example, in some embodiments, the bacterial cells (such as *E. coli* cells) express one or more heterologous nucleic acids described herein under the control of a strong promoter in a low to medium copy plasmid and are cultured at 34° C.

Standard culture conditions and modes of fermentation, such as batch, fed-batch, or continuous fermentation that can be used are described in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716. Batch and Fed-Batch fermentations are common and well known in the art and examples can be found in Brock, Biotechnology: *A Textbook of Industrial Microbiology*, Second Edition (1989) Sinauer Associates, Inc.

In some aspects, the cells are cultured under limited glucose conditions. By "limited glucose conditions" is meant that the amount of glucose that is added is less than or about 105% (such as about 100%, 90%, 80%, 70%, 60%, 50%, 40%, 30%, 20%, or 10%) of the amount of glucose that is consumed by the cells. In particular aspects, the amount of glucose that is added to the culture medium is approximately the same as the amount of glucose that is consumed by the cells during a specific period of time. In some aspects, the rate of cell growth is controlled by limiting the amount of added glucose such that the cells grow at the rate that can be supported by the amount of glucose in the cell medium. In some aspects, glucose does not accumulate during the time the cells are cultured. In various aspects, the cells are cultured under limited glucose conditions for greater than or about 1, 2, 3, 5, 10, 15, 20, 25, 30, 35, 40, 50, 60, or 70 hours. In various aspects, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions can allow more favorable regulation of the cells.

In some aspects, the recombinant (e.g., bacterial) cells are grown in batch culture. The cells can also be grown in fed-batch culture or in continuous culture. Additionally, the cells can be cultured in minimal medium, including, but not limited to, any of the minimal media described above. The minimal medium can be further supplemented with 1.0% (w/v) glucose, or any other six carbon sugar, or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract.

Methods of Using the Recombinant Cells to Produce Isoprene

The invention contemplates methods of producing isoprene by culturing any of the recombinant cells described herein under reduced oxygen inlet levels and/or the other culturing conditions as those disclosed herein.

Reduced Oxygen Inlet Levels

Isoprene can be produced by culturing the recombinant cells described herein under reduced oxygen inlet levels. Measurement of oxygen inlet in the fermentator is known to one of skill in the art. For example, oxygen sensors can be placed near or at the inlet where one or more types of gases are introduced into the fermentor. The different oxygen levels can be monitored and different types of calculation (e.g., averaging) can be done to determine oxygen levels. Adjustments can be made so that the desired oxygen levels are reached and/or maintained during fermentation. One consideration for production of isoprene is the flammability and explosive capability during production and/or recovery. Ambient air contains about 21% oxygen, however, this level of oxygen in the off-gas can be hazardous due to safety concerns for explosions, fires and other flammability considerations. Accordingly, for any of the aspect herein, care should be taken to keep the levels of oxygen in the off-gas within safe operating ranges, such those promulgated by NFPA 69 and/or as taught in WO 2010/003007, the contents of which are specifically incorporated for teaching for safe operating ranges and flammability levels.

Increased performance of the recombinant cells to produce isoprene can be achieved when the fermentation run is conducted at reduced oxygen inlet levels. In one aspect, the reduced oxygen inlet level can be between about 5% to about 15% oxygen. In another aspect, the reduced oxygen inlet level can be between about 5% to about 11% oxygen. In another aspect, the reduced oxygen inlet level can be between about 7% to about 10% oxygen. In another aspect, the reduced oxygen inlet level can be between about 7% to about 10% oxygen. In another aspect, the reduced oxygen inlet level can be between about 7% to about 9% oxygen. In other aspects, the reduced oxygen inlet level can be about 5%, 5.1%, 5.2%, 5.3%, 5.4%, 5.5%, 5.6%, 5.7%, 5.8%, 5.9%, 6%, 6.1%, 6.2%, 6.3%, 6.4%, 6.5%, 6.6%, 6.7%, 6.8%, 6.9%, 7%, 7.1%, 7.2% 7.3%, 7.4%, 7.5%, 7.6%, 7.7%, 7.8%, 7.9%, 8%, 8.1%, 8.2%, 8.3%, 8.4%, 8.5%, 8.6%, 8.7%, 8.8%, 8.9%, 9%, 9.1%, 9.2%, 9.3%, 9.4%, 9.5%, 9.6%, 9.7%, 9.8%, 9.9% or 10% oxygen. In one embodiment, the reduced oxygen inlet level is about 7.7% oxygen. In one embodiment, the reduced oxygen inlet level is about 9.3% oxygen.

As described herein, the recombinant cells are grown under reduced oxygen inlet levels. In other aspects, the cells are grown under atmospheric conditions comprising any of about 4%, 5%, 6%, 7%, 8%, 9%, 10%, 11%, 12%, 13%, 14%, or 15%, inclusive, including any values in between these percentages, oxygen. In other aspects, the cells are grown under atmospheric conditions comprising any of about 3-8%, 3.5-8.5%, 4-9%, 4.5-9.5%, 5-10%, 5.5-10.5%, 6-11%, or 6.5-11.5% oxygen. In any of these aspects or embodiments, regardless of the starting amount of the oxygen inlet, the oxygen level in the off-gas is kept at a level that is below the buffer zone set forth by national standards, such as NFPA 69. In other embodiments, the oxygen level in the off-gas is kept at a level that is below the flammability zone as by national standards, such as NFPA 69 and/or as taught in WO 2010/003007.

Other sources of fermentor inlet vapor can also be used. For example, one of skill in the art can mix controlled ratios (wt:wt or v:v) of compressed air that may contain super-ambient, ambient or sub-ambient levels of oxygen with compressed nitrogen that may have various levels of impurities including ($O_2$, $CO_2$, Argon and/or other inerts and/or hydrocarbons such as isoprene) to create a vapor mixture that meets the desired inlet [$O_2$] vapor composition.

These compressed vapors can be produced from air directly or by using membranes, cryo-separation or electrolysis techniques to create one or both of the compressed vapors. The individual vapors can be created and used immediately or one or both streams can be prepared in advance and stored separately in cylinders, trailers and/or cryogenic storage tanks or pre-mixed and stored separately in cylinders, trailers and/or cryogenic storage tanks. The vapor(s) may be dried to remove moisture and/or filtered to remove solids and/or biological contaminants prior to introducing the vapor into the fermentor.

As noted above, the cells grow in two general phases: (1) growth phase (such as linear growth phase) where the recombinant cells propagate and expand in number and (2) fermentation or production phase, where recombinant the cells are producing isoprene in commercially relevant amounts (see, e.g., WO 2010/003007, which is incorporated herein for teachings on commercially relevant amounts of isoprene). In one aspect, isoprene can be made by culturing recombinant cells that are in the production phase under reduced oxygen inlet levels as described herein. In another aspect, isoprene can be made by culturing recombinant cells that are in the growth phase under reduced oxygen inlet level as described herein. In another aspect, isoprene can be made by culturing recombinant cells that have a mix of cells in both the growth and the production phase under reduced oxygen inlet level as described herein. In one embodiment, the cell culture is at least about 99% in production phase. In other embodiments, the cell culture is at least about 98%, 97%, 96%, 95%, 94%, 93%, 92%, 91%, 90%, 85%, 80%, 75%, 70%, 65%, 60%, 55%, and 50% in production phase. As previously described above, the recombinant cells that are being cultured under reduced oxygen inlet levels can have nucleic acids encoding for isoprene synthase, one or more of the DXP pathway polypeptides, one or more of the MVA pathway polypeptides. The cells can further contain nucleic acids encoding for IDI and other engineering steps (e.g., reducing IspA activity) to make the recombinant cells produce isoprene at an increased amount as compared with to the same cell without the engineering.

In some aspects, the improved method for producing isoprene using reduced oxygen inlet levels is capable improving production of isoprene by at least about 5% as compared to using ambient air or oxygen levels in ambient air (e.g., about 21% oxygen). In other aspects, the improved production of isoprene is at least about 6%, 7%, 8%, 9%, 10%, 11%, 12%, 13%, 14%, 15%, 16%, 17% 18%, 19%, or 20% as compared to using ambient air or oxygen levels in ambient air. In other aspects, the improved production of isoprene is at least about 25%, 30%, 35%, 40%, 45%, 50%, 55%, 60%, 65%, 70%, 75%, 80%, 85%, 90%, 95%, or 100% as compared to using ambient air or oxygen levels in ambient air. In other aspects, the improved production of isoprene is at least about 120%, 150%, 175%, 200%, 250% or 300% as compared to using ambient air or oxygen levels in ambient air.

In other aspects, isoprene productivity can be affected by varying the inlet airflow rates. In some aspects, the inlet airflow rate is between about 8 SLPM and 14 SLPM. In another aspect, the inlet airflow rate is between about 6 SLPM and 14 SLPM. In another aspect, the inlet airflow rate is between about 8 SLPM and 12 SLPM. In another aspect, the inlet airflow rate is about 10 SLPM. In other aspects, the inlet airflow rate is about 6 SLPM, 7 SLPM, 8 SLPM, 9 SLPM, 10 SLPM, 11 SLPM, 12 SLPM, 13 SLPM, or 14 SLPM.

As shown in Example 1, the peak instantaneous yield of isoprene was increased by about 11.6% when 5% oxygen inlet levels was used as compared to when ambient oxygen levels (~21%) was used. When 7.7% oxygen inlet level was used, peak instantaneous yield was increased by about 35.8% as compared to when ambient oxygen level was used. When 9.3% oxygen inlet levels was used, peak instantaneous yield was increased by about 37.6% as compared to when ambient oxygen levels was used.

The peak cumulative mass yield of isoprene was increased by about 8% when 5% oxygen inlet levels was used as compared to when ambient oxygen levels (~21%) was used. When 7.7% oxygen inlet level was used, peak cumulative mass yield was increased by about 32.3% as compared to when ambient oxygen level was used. When 9.3% oxygen inlet levels was used, peak cumulative mass yield was increased by about 41.7% as compared to when ambient oxygen levels was used.

The CPI was increased by about 16.8% when 5% oxygen inlet levels was used as compared to when ambient oxygen levels (~21%) was used. When 7.7% oxygen inlet level was used, CPI was increased by about 61% as compared to when ambient oxygen level was used. When 9.3% oxygen inlet levels was used, CPI was increased by about 72.6% as compared to when ambient oxygen levels was used.

The peak specific productivity was increased by about 39.7% when 7.7% oxygen inlet levels was used as compared to when ambient oxygen levels (~21%) was used. When 9.3% oxygen inlet levels was used, peak cumulative mass yield was increased by about 26% as compared to when ambient oxygen levels was used.

In another aspect, isoprene can be produced by culturing recombinant cells comprising an ispA gene having decreased functional activity and one or more nucleic acids encoding: (a) an isoprene synthase polypeptide, wherein the isoprene synthase polypeptide is encoded by a heterologous nucleic acid; and (b) one or more mevalonate (MVA) pathway polypeptides. In one aspect, one or more heterologous nucleic acids encoding a HMG-CoA reductase, a lower MVA pathway polypeptide, and an isoprene synthase polypeptide can be used. In another aspect, isoprene can be produced by culturing recombinant cells comprising one or more heterologous nucleic acids encoding a HMG-CoA reductase and HMG-CoA synthase, a lower MVA pathway polypeptide, and an isoprene synthase polypeptide. In some aspects, the recombinant cells described herein exhibit any of about 10%, 15%, 20%, 25%, 30%, 35%, 40%, 45%, 50%, 55%, 60%, 65%, 70%, 75%, 80%, 95%, or 100%, inclusive, including any value in between these percentages, increased isoprene production in comparison to cells which do not comprise an IspA having decreased functional activity. The isoprene can be produced from any of the cells described herein and according to any of the methods described herein. Any of the cells can be used for the purpose of producing isoprene from carbohydrates, including six carbon sugars such as glucose.

The cells can further comprise one or more nucleic acid molecules encoding the lower MVA pathway polypeptide(s) described above (e.g., MVK, PMK, MVD, and/or IDI) and any of the isoprene synthase polypeptide(s) described above (e.g. *P. alba* isoprene synthase). In some aspects, the recombinant (e.g., bacterial) cells can be any of the cells described herein. Any of the isoprene synthases or variants thereof described herein, any of the bacterial strains described herein, any of the promoters described herein, and/or any of the vectors described herein can also be used to produce isoprene using any of the energy sources (e.g. glucose or any other six carbon sugar) described herein. In some aspects, the method of producing isoprene further comprises a step of recovering the isoprene.

In some aspects, the amount of isoprene produced is measured at a productivity time point. In some aspects, the productivity for the cells is about any of the amounts of isoprene disclosed herein. In some aspects, the cumulative, total amount of isoprene produced is measured. In some aspects, the cumulative total productivity for the cells is about any of the amounts of isoprene disclosed herein.

In some aspects, any of the cells described herein (for examples the cells in culture) produce isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some aspects, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some aspects, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some aspects, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some aspects, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some aspects, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h.

In some aspects, the cells in culture produce a cumulative titer (total amount) of isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some aspects, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some aspects, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some aspects, the isoprene produced by the cells in culture (such as any of the recombinant cells described herein) comprises at least about 1, 2, 5, 10, 15, 20, or 25% by volume of the fermentation offgas. In some aspects, the isoprene comprises between about 1 to about 25% by volume of the offgas, such as between about 5 to about 15%, about 15 to about 25%, about 10 to about 20%, or about 1 to about 10%.

In some aspects, the cells in culture (such as any of the recombinant cells described herein) produce any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, higher cumulative isoprene yield on glucose in comparison to cells that do not comprise decreased IspA functional activity. In another aspect, the cells in culture (such as any of the recombinant cells described herein) produce any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, greater isoprene productivity in comparison to cells that do not comprise decreased IspA functional activity. In other aspects, the cells in culture (such as any of the recombinant cells described herein) produce any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, greater isoprene peak specific productivity in comparison to cells that do not comprise decreased IspA functional activity. In some aspects, the cells in culture (such as any of the recombinant cells described herein) produce any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, greater cell isoprene productivity index in comparison to cells that do not comprise decreased IspA functional activity.

Exemplary Purification Methods

In some aspects, any of the methods described herein further include a step of recovering isoprene produced by any of the recombinant cells disclosed herein. In some aspects, the isoprene is recovered by absorption stripping (See, e.g., U.S. Patent Application Publication No. 2011/0178261 A1). In some aspects, any of the methods described herein further include a step of recovering the heterologous polypeptide.

Suitable purification methods are described in more detail in U.S. Patent Application Publication No. US2010/0196977 A1.

Throughout this specification, various patents, patent applications and other types of publications (e.g., journal articles) are referenced. The disclosure of all patents, patent applications, and publications cited herein are hereby incorporated by reference in their entirety for all purposes.

The invention can be further understood by reference to the following examples, which are provided by way of illustration and are not meant to be limiting.

EXAMPLES

General Information

Strains Used

| Strain name | Genotype | Parent | Plasmids |
|---|---|---|---|
| CMP451 | BL21 pgl PL.2mKKDyI GI 1.2 gltA | | None |
| CMP457 | BL21 pgl+ PL.2 mKKDyI GI1.2 gltA, pTrc(MEA)alba_mMVK, pCLPtrcUpper_Efaecalis | CMP451 | pDW34, MCM82 |
| CMP561 | HMB GI1.2gltA, pCLPtrcUpper, pTrc(MEA G491S)alba mMVK | | pDW72, pMCM82 |
| CMP596 | BL21 pgl PL.2mKKDyI GI 1.2 gltA ldhA::Kan | CMP451 | None |
| CMP722 | BL21 pgl PL.2mKKDyI GI 1.2 gltA ldhA | CMP596 | None |
| CMP876 | BL21 pgl PL.2mK*KDyI GI 1.2 gltA ldhA | CMP451 | None |
| CMP882 | BL21 pgl PL.2mKKDyI GI 1.2 gltA, pTrcHis2B, pCL1920 | CMP451 | pTrcHis2B, pCL1920 |
| CMP884 | BL21 pgl PL.2mK*KDyI GI 1.2 gltA, pTrcHis2B, pCL1920 | CMP451 | pTrcHis2B, pCL1920 |
| CMP981 | BL21 pgl PL.2mKKDyI GI1.2gltA yhfSpKD3IspAyhfS | CMP451 | None |
| CMP992 | BL21 pgl PL.2mKKDyI GI1.2gltA yhfSFRTIspAyhfS | CMP981 | None |
| CMP1018 | BL21 pgl PL.2mKKDyI GI1.2gltA yhfSFRTIspAyhfS thipKD3truncIspA | CMP992 | None |
| CMP1024 | BL21 pgl PL.2mKKDyI GI 1.2 gltA ldhA Cm::ispA-proteolytic tag | CMP722 | None |
| CMP1030 | BL21 pgl PL.2mKKDyI GI1.2gltA yhfSFRTIspAyhfS thiFRTtruncIspA | CMP1018 | None |
| CMP1034 | BL21 pgl PL.2mKKDyI GI 1.2 gltA ldhA ispA-proteolytic tag | CMP1024 | None |
| CMP1043 | HMB GI1.2gltA, pCLPtrcUpper, pTrc(MEA G491S)alba mMVK | CMP561 | pDW72, pMCM82 |
| CMP1059 | BL21 pgl PL.2mKKDyI GI 1.2 gltA ldhA ispA-proteolytic tag, pCLPtrcUpper, pTrc(MEA variant)alba mMVK | CMP1034 | MCM82, pCHL243 |
| CMP1061 | BL21 pgl PL.2mKKDyI GI1.2gltA yhfSFRTIspAyhfS thiFRT3truncIspA, pCLPtrcUpper, pTrc(MEA variant)alba mMVK | CMP1030 | MCM82, pCHL243 |
| CMP1067 | BL21 pgl PL.2mKKDyI GI1.2gltA yhfSpKD4PyddVIspAyhfS thipKD3truncIspA | CMP1018 | None |
| CMP1075 | BL21 pgl PL.2mKKDyI GI1.2gltA yhfSFRTPyddVIspAyhfS thiFRTtruncIspA | CMP1067 | None |
| CMP1082 | BL21 pgl PL.2mKKDyI GI1.2gltA yhfSFRTPyddVIspAyhfS thiFRTtruncIspA, pCLPtrcUpper_Efaecalis, pTrc(MEA variant)alba mMVK | CMP1075 | MCM82, pCHL243 |
| CMP1101 | BL21 pgl PL.2mKKDyI GI1.2gltA yhfSFRTIspAyhfS thipKD3truncIspA yhfS-pKD4-PispA_avianA166W | CMP1018 | None |
| CMP1102 | BL21 pgl PL.2mKKDyI GI1.2gltA yhfSFRTIspAyhfS thipKD3truncIspA yhfS-pKD4-PispA_avianN144'W | CMP1018 | None |
| CMP1107 | BL21 pgl PL.2mKKDyI GI1.2gltA yhfSFRTIspAyhfS thipKD3truncIspA yhfS-FRT-PispA_avianA166W | CMP1101 | None |
| CMP1108 | BL21 pgl PL.2mKKDyI GI1.2gltA yhfSFRTIspAyhfS thipKD3truncIspA yhfS-FRT-PispA_avianN144'W | CMP1102 | None |
| CMP1112 | BL21 pgl PL.2mKKDyI GI1.2gltA yhfSFRTIspAyhfS thipKD3truncIspA yhfS-FRT-PispA_avianA166W, pCLPtrcUpper_Efaecalis, pTrc(MEA variant)alba mMVK | CMP1107 | MCM82, pCHL243 |
| CMP1113 | BL21 pgl PL.2mKKDyI GI1.2gltA yhfSFRTIspAyhfS thipKD3truncIspA yhfS-FRT-PispA_avianN144'W, pCLPtrcUpper_Efaecalis, pTrc(MEA variant)alba mMVK | CMP1108 | MCM82, pCHL243 |
| CMP1125 | BL21 pgl::Kan PL.2mKKDyI GI1.2gltA yhfSFRTPyddVIspAyhfS thiFRTtruncIspA | CMP1075 | None |
| CMP1133 | BL21 Δpgl PL.2mKKDyI GI1.2gltA | CMP1125 | None |

-continued

| Strain name | Genotype | Parent | Plasmids |
|---|---|---|---|
| CMP1136 | yhfSFRTPyddVIspAyhfS thiFRTtruncIspA BL21 Δpgl PL.2mKKDyI GI1.2gltA yhfSFRTPyddVIspAyhfS thiFRTtruncIspA, pCLPtrcUpper_Efaecalis, pTrc(MEA variant)alba mMVK | CMP1133 | MCM82, pCHL243 |
| MCM1020 | BL21 t pgl, pTrcHis2B, pCL1920 | CMP258 | pTrcHis2B, pCL1920 |

Example 1

This purpose of this experiment was to evaluate isoprene production from *E. coli*(BL21) expressing introduced genes from the mevalonate pathway and grown in fed-batch culture at the 15-L scale. An isoprene producing strain CMP1043 (HMB GI1.2gltA pMCM82, pDW72) was run in a fed-batch fermentation process which varied the oxygen concentration of the inlet gas (5.0, 7.7 and 9.3 vol %, in respective runs), while maintaining the volumetric gas flow rate at 8.0 standard liters per minute. CMP1043 strain expresses wild type ispA. MCM82 is pCL PtrcUpperPathway encoding *E. faecalis* mvaE and mvaS. pDW72 encodes for *P. alba* truncated isoprene synthase MEA G491S variant, also described in WO 2009/132220, the contents of which are specifically incorporated for its disclosure. The balance gas in the three preceding cases was nitrogen. The performance metrics (cumulative isoprene yield on glucose, instantaneous isoprene yield on glucose, specific productivity and cell productivity index) are compared to an isogenic strain CMP561 (HMB GI1.2gltA pMCM82, pDW72) that was run in the same conditions except the inlet gas was air (20.95 vol %).

Phenotype is full (upper/lower) MVA pathway with archeal MVK and MEA G491S isoprene synthase.

Results

Figure 1:
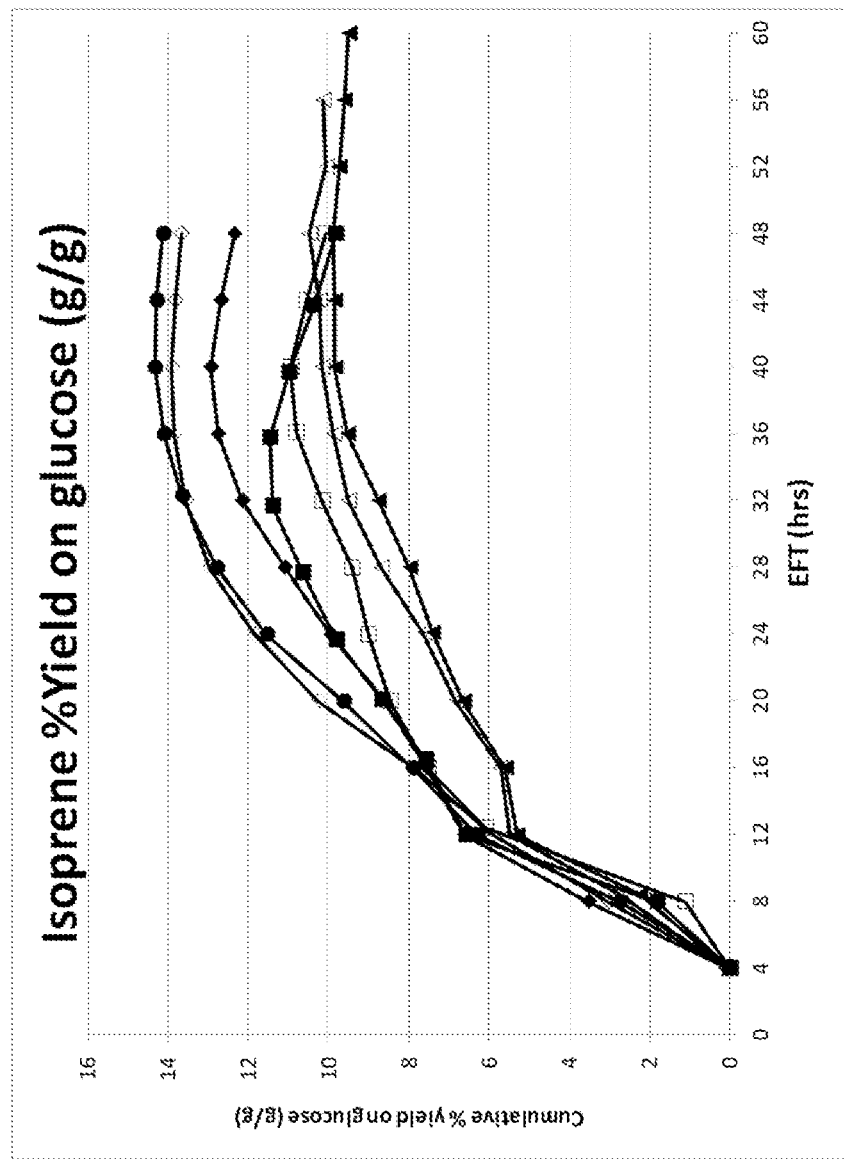
FIG. 1 depicts a graph showing yield of isoprene on glucose achieved in each 15-L fermentation over time. All runs used a production host of the same genotype. The oxygen inlet % is listed below for each experiment. All runs using the lower oxygen inlet gas (circles, squares, and diamonds in the figure below) achieved a higher % yield of isoprene on glucose than the two runs using standard house air (open and closed triangles in the figure).

While runs using the 5.0% oxygen inlet gas (20110909, 20110940) achieved a modestly higher mass yield of isoprene on glucose than the two runs using standard house air (20100522, 20100523), the three runs using 7.7%, 7.7% and 9.3% (20111019, 20111020, 20111109, respectively) achieved a significantly higher mass yield of isoprene on glucose. See, e.g., Table 1, FIG. 1 and FIG. 5. FIG. 1 depicts a graph showing yield of isoprene on glucose achieved in each 15-L fermentation over time is shown in chart 1. All runs used a production host of the same genotype. The oxygen inlet % is listed below for each experiment. All runs using the lower oxygen inlet gas (circles, squares, and diamonds in the figure below) achieved a higher % yield of isoprene on glucose than the two runs using standard house air (open and closed triangles in the figure).

Overall yield was calculated using the following formula:

% wt Yield on glucose=Isoprene total $(t)$/[(Feed Wt(0)−Feed Wt$(t)$+83.5)*0.59)], where 0.59 is the wt % of glucose in the glucose feed solution and 83.5 is the grams of this feed batched into the fermentor at t=0. Each feed had its weight % measured independently.

The run 20100522: CMP561 at 20.9% O2 inlet is depicted by closed black triangles. The run 20100523: CMP561 at 20.9% O2 inlet is depicted by open black triangles. The run 20110940: CMP1043 at 5.0% O2 inlet is depicted by closed black squares. The run 20110909: CMP1043 at 5.0% O2 inlet is depicted by open black squares. The run 20111019: CMP1043 at 7.7% O2 inlet is depicted by closed black diamonds. The run 20111020: CMP1043 at 7.7% O2 inlet is depicted by open black diamonds. The run 20111109: CMP1043 at 9.3% O2 inlet is depicted by closed black circles.

All runs using the lower oxygen inlet gas (20110909, 20110940, 20111019, 20111020, 20111109) achieved a higher peak instantaneous % yield of isoprene on glucose than the two runs using standard house air (20100522, 20100523). See Table 1, FIG. 2 and FIG. 6. FIG. 2 depicts a graph showing instantaneous yield of isoprene on glucose achieved in each 15-L fermentation over time. All runs used a production host of the same genotype. The oxygen inlet % is listed below for each experiment. All runs using the lower oxygen inlet gas (circles, squares, and diamonds) achieved a higher peak instantaneous % yield of isoprene on glucose than the two runs using standard house air (open and closed triangles). FIG. 6 is a graph where the peak instantaneous yield data in table 1 is plotted as a bar graph. All runs using the lower oxygen inlet gas (20110909, 20110940, 20111019, 20111020, 20111109) achieved a higher instantaneous % yield of isoprene on glucose than the two runs using standard house air (20100522, 20100523).

Isoprene Instantaneous yield was calculated using the following formula:

Isoprene Inst. yield (g/g %)=Isoprene produced $(t_1 - t_0)$/consumed glucose $(t_1 - t_0)$*100.

The run 20100522: CMP561 at 20.9% O2 inlet is depicted by closed black triangles. The run 20100523: CMP561 at 20.9% O2 inlet is depicted by open black triangles. The run 20110940: CMP1043 at 5.0% O2 inlet is depicted by closed black squares. The run 20110909: CMP1043 at 5.0% O2 inlet is depicted by open black squares. The run 20111019: CMP1043 at 7.7% O2 inlet is depicted by closed black diamonds. The run 20111020: CMP1043 at 7.7% O2 inlet is depicted by open black diamonds. The run 20111109: CMP1043 at 9.3% O2 inlet is depicted by closed black circles.

All runs using the lower oxygen inlet gas (20110909, 20110940, 20111019, 20111020, 20111109) achieved a higher overall cell productivity index than the two runs using standard house air (20100522, 20100523). See Table 1, FIG. 3 and FIG. 7. FIG. 3 depicts a graph showing cell productivity index (CPI) achieved in each 15-L fermentation over time. All runs used a production host of the same genotype. The oxygen inlet % is listed for each experiment. All runs using the lower concentration oxygen inlet gas (circles, squares and diamonds) achieved a higher cell productivity index compared to the two runs using standard house air (open and closed triangles). FIG. 7 is a graph where the cell productivity index data in table 1 is plotted as bar graph. All runs using the lower oxygen inlet gas (20110909, 20110940, 20111019, 20111020, 20111109) achieved a higher cell productivity index than the two runs using standard house air (20100522, 20100523).

Cell Productivity Index (CPI) was calculated using the following formula:

CPI=total grams Isoprene/total grams dry cell weight

The run 20100522: CMP561 at 20.9% O2 inlet is depicted by closed black triangles. The run 20100523: CMP561 at 20.9% O2 inlet is depicted by open black triangles. The run 20110940: CMP1043 at 5.0% O2 inlet is depicted by closed black squares. The run 20110909: CMP1043 at 5.0% O2 inlet is depicted by open black squares. The run 20111019:

CMP1043 at 7.7% O2 inlet is depicted by closed black diamonds. The run 20111020: CMP1043 at 7.7% O2 inlet is depicted by open black diamonds. The run 20111109: CMP1043 at 9.3% O2 inlet is depicted by closed black circles.

While runs using the 5.0% oxygen inlet gas (20110909, 20110940) achieved about the same peak specific productivity as the two runs using standard house air (20100522, 20100523), the three runs using 7.7%, 7.7% and 9.3% (20111019, 20111020, 20111109, respectively) achieved a significantly higher peak specific productivity of isoprene. See Table 1, FIG. 4 and FIG. 8. FIG. 4 depicts a graph showing specific productivity achieved in each 15-L fermentation over time. All runs used a production host of the same genotype. The oxygen inlet % is listed for each experiment. While runs using the 5.0% oxygen inlet gas (20110909, 20110940) achieved about the same specific productivity as the two runs using standard house air (20100522, 20100523), the three runs using 7.7%, 7.7% and 9.3% (20111019, 20111020, 20111109, respectively) achieved a significantly higher specific productivity of isoprene. FIG. 8 is a graph where the peak specific productivity data in table 1 is plotted as bar graph. While runs using the 5.0% oxygen inlet gas (20110909, 20110940) achieved about the same specific productivity as the two runs using standard house air (20100522, 20100523), the three runs using 7.7%, 7.7% and 9.3% (20111019, 20111020, 20111109, respectively) achieved a significantly higher peak specific productivity of isoprene.

Specific Productivity was calculated using the following formula:

Specific productivity (mg/L/hr/OD)=HgER*68.117 g/mol/OD.

HgER is the Isoprene Evolution Rate in (mmol/L/hr).

OD=optical density=Absorbance at 550 nm*dilution factor in water

The run 20100522: CMP561 at 20.9% O2 inlet is depicted by closed black triangles. The run 20100523: CMP561 at 20.9% O2 inlet is depicted by open black triangles. The run 20110940: CMP1043 at 5.0% O2 inlet is depicted by closed black squares. The run 20110909: CMP1043 at 5.0% O2 inlet is depicted by open black squares. The run 20111019: CMP1043 at 7.7% O2 inlet is depicted by closed black diamonds. The run 20111020: CMP1043 at 7.7% O2 inlet is depicted by open black diamonds. The run 20111109: CMP1043 at 9.3% O2 inlet is depicted by closed black circles.

Method:
Medium Recipe (Per Liter Fermentation Medium):
K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):
Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):
Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):
MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):
Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

This experiment was carried out to monitor isoprene formation from glucose at the desired fermentation pH (7.0) and temperature (34° C.). A frozen vial of the *E. coli* strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L.

The inlet gas using to maintain bioreactor backpressure at 0.7 bar gauge and to provide the oxygen to the production organisms was supplied by Matheson Tri-Gas, Inc in compressed gas cylinders.

Various concentrations of oxygen were used, and can be summarized as follows.

| Run Number | Inlet gas Rate (standard liters per minute) | Inlet gas composition | Strain used |
|---|---|---|---|
| 20100522 20100523 | 8 SLPM | 20.95% Oxygen, 78% Nitrogen, 0.9% Argon, 0.036% Carbon Dioxide (Air from house compressors) | CMP561 |
| 20110871 20110909 | 8 SLPM | 5% oxygen 95% nitrogen | CMP1043 |
| 20111019 20111020 | 8 SLPM | 7.7% oxygen 92.3% nitrogen | CMP1043 |
| 20111109 | 8 SLPM | 9.3% oxygen 90.7 nitrogen | CMP1043 |

The batched media had glucose batched in at 9.7 g/L. Induction was achieved by adding isopropyl-beta-D-1-thiogalactopyranoside (IPTG). IPTG was added to the tank to bring the concentration to 200 uM when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum isoprene mass yield on glucose, a total of 48 to 56 hrs elapsed fermentation time.

Results

Isoprene is volatile and can be efficiently swept from the tank by the inlet gas. The isoprene level in the bioreactor off-gas was determined using two mass spectrometers, an iSCAN (Hamilton Sundstrand), and a Hiden HPR20 (Hiden Analytical) mass spectrometer. Oxygen, Nitrogen, and CO2 levels in the offgas were determined by the same mass spec units.

Dissolved Oxygen in the fermentation broth is measured by sanitary, sterilizable probe with an optical sensor provided Hamilton Company. The citrate, glucose, acetate, and mevalonate concentrations in the fermentor broth was determined in broth samples taken at 4 hour intervals by an HPLC analysis. Concentration in broth samples was determined by comparison of the refractive index response versus a previously generated calibration curve using standard of a known concentration.

HPLC Information
System: Waters Alliance 2695
Column: BioRad—Aminex HPX-87H Ion Exclusion Column 300 mm×7.8 mm Catalog #125-0140
Column Temperature: 50 C
Guard column: BioRad—Microguard Cation H refill 30 mm×4.6 mm Catalog #125-0129
Running buffer: $0.01 NH_2SO_4$
Running buffer flow rate: 0.6 ml/min
Approximate running pressure: ~1100-1200 psi
Injection volume: 20 microliters
Detector: Refractive Index (Knauer K-2301)
Runtime: 26 minutes

TABLE 1

| Strain description | Oxygen inlet Conc. (vol %) | Run Number | Peak instantaneous yield of isoprene on glucose (g/g %) | Peak cumulative mass yield of Isoprene on glucose (g/g) | CPI at max overall isoprene yield (g Isoprene/gDCW) | Peak Specific Productivity (mg isoprene/L/hr/OD) |
|---|---|---|---|---|---|---|
| CMP1043 | 5.0% | 20110909 | 13.81 | 10.6 | 1.07 | 19.49 |
|  |  | 20110940 | 14.5 | 11.12 | 1.15 | 21.07 |
|  |  | Average | 14.2 | 10.86 | 1.11 | 20.28 |
|  | 7.7% | 20111019 | 16.22 | 12.76 | 1.34 | 27.82 |
|  |  | 20111020 | 17.03 | 13.86 | 1.71 | 31.78 |
|  |  | Average | 16.63 | 13.31 | 1.53 | 29.8 |
|  | 9.3% | 20111109 | 16.85 | 14.26 | 1.64 | 26.87 |
|  |  | Average | 16.85 | 14.26 | 1.64 | 26.87 |
| CMP561 | 20.95% | 20100522 | 12.26 | 9.85 | 0.92 | 21.89 |
|  |  | 20100523 | 12.22 | 10.26 | 0.98 | 20.75 |
|  |  | Average | 12.24 | 10.06 | 0.95 | 21.32 |

The peak instantaneous yield of isoprene was increased by about 11.6% when 5% oxygen inlet levels was used as compared to when ambient oxygen levels (~21%) was used. When 7.7% oxygen inlet level was used, peak instantaneous yield was increased by about 35.8% as compared to when ambient oxygen level was used. When 9.3% oxygen inlet levels was used, peak instantaneous yield was increased by about 37.6% as compared to when ambient oxygen levels was used.

The peak cumulative mass yield of isoprene was increased by about 8% when 5% oxygen inlet levels was used as compared to when ambient oxygen levels (~21%) was used. When 7.7% oxygen inlet level was used, peak cumulative mass yield was increased by about 32.3% as compared to when ambient oxygen level was used. When 9.3% oxygen inlet levels was used, peak cumulative mass yield was increased by about 41.7% as compared to when ambient oxygen levels was used.

The CPI was increased by about 16.8% when 5% oxygen inlet levels was used as compared to when ambient oxygen levels (~21%) was used. When 7.7% oxygen inlet level was used, CPI was increased by about 61% as compared to when ambient oxygen level was used. When 9.3% oxygen inlet levels was used, CPI was increased by about 72.6% as compared to when ambient oxygen levels was used.

The peak specific productivity was increased by about 39.7% when 7.7% oxygen inlet levels was used as compared to when ambient oxygen levels (~21%) was used. When 9.3% oxygen inlet levels was used, peak cumulative mass yield was increased by about 26% as compared to when ambient oxygen levels was used.

Thus, this example demonstrates that reduced oxygen inlet levels helps to increase production of isoprene, as shown by measuring various production parameters.

Example 2

Large Scale Fermentation of CMP1082

Fermentation runs were performed to test certain performance metrics (cumulative isoprene yield on glucose, isoprene productivity, peak specific productivity and cell productivity index) of strain CMP1082 (HMB GI1.2gltA, PyddVIspA_GO, truncIspA, MCM82, pCHL243) to that of a control strain CMP1043 (HMB GI1.2gltA, −MCM82, pCHL243) according to the following protocol.

Medium Recipe (per liter fermentation medium): K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di $H_2O$. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (per liter): Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (per liter): Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (per liter): MgSO4*7H2O 296 g, citric acid monohydrate 296 g, ferric ammonium citrate 49.6 g. All components were dissolved in water, q.s. to volume and filter sterilized with 0.22 micron filter.

Feed solution (per kilogram): Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

Metabolite Analysis:

Metabolite extraction from *E. coli.* was achieved by withdrawing approximately 3 mL of culture into a tube filled with 9 mL of dry ice-cold methanol. The resulting samples were weighed to calculate the amount of sampled broth and then stored at −80° C. until further analysis. For metabolite extraction and concentration, 0.5 mL aliquots of cell suspension (1 mL aliquot was used if cell density of the culture measured as $OD_{600}$ was below 50) were diluted with 2.5 mL of methanol/ammonium acetate buffer (5 mM, pH=8.0) mixture (6:1, v/v) and cell debris was pelleted by a 5 minute centrifugation. The supernatant was collected and loaded onto Strata-X-AW columns from Phenomenex (33 μm 30 mg/3 mL Polymeric Weak Anion Exchange). The cell pellet was extracted two more times, first with 3 mL of the methanol/ammonium acetate buffer (5 mM, pH=8.0) mixture (6:1 v/v), and then with 3 mL of methanol/ammonium acetate buffer (5 mM, pH=8.0) mixture (1:1 v/v). Both times the cells were pelleted by centrifugation, and the resulting supernatants were consecutively loaded onto the same Strata-X-AW columns. During the extraction-centrifugation, samples with cells were kept below 4° C. After washing the columns with 1 mL of water and 1 mL of methanol, metabolites of interest were eluted from the columns first with 0.3 mL of concentrated $NH_4OH$/methanol (1:14, v/v) mixture and then with 0.3 mL of concentrated $NH_4OH$/methanol/water (1:12:2, v/v/v) mixture. The resulting eluant was neutralized by adding 20 μL of glacial acetic acid, and then cleared by centrifugation.

Analysis of metabolites was carried out by mass spectrometry using a TSQ Quantum Access TSQ system (Thermo Scientific). All system control, data acquisition, and mass spectral data evaluation were performed using XCalibur and LCQuan software (Thermo Scientific). For the LC-ESI-MS/MS method, a chiral Nucleodex β-OH 5 μM HPLC column (100×2 mm, Macherey-Nagel, Germany) was used with a CC 8/4 Nucleodex beta-OH guard cartridge. A mobile phase gradient was applied in which mobile phase A was 100 mM ammonium acetate (SigmaUltra grade, Sigma) buffer (pH=8) in MilliQ-grade water, mobile phase B was MilliQ-grade water, and mobile phase C was LC-MS grade acetonitrile (Chromasolv, Riedel-de Haën). The column and sample tray temperatures were reduced to 5° C. and 4° C., respectively. The injection volume was 10 μL.

Mass detection was carried out using electrospray ionization in the negative mode (ESI spray voltage of 3.0 kV and ion transfer tube temperature of 390° C.). The following m/z values for precursor ions were selected to detect the metabolites of interest in SRM mode: 245.0 for IPP and DMAPP, 313.1 for GPP, 381.1 for FPP, 227.0 for MVP, and 307.1 for MVPP. Concentrations of metabolites were determined based on the integrated intensities of peaks generated by PO3— product ion (m/z=79.0). Calibration curves obtained by injection of standards were used to calculate concentrations of metabolites in cell extracts. IPP, DMAPP, GPP, and FPP standards were purchased from Echelon Biosciences Inc. and MVP and MVPP (R-forms) were purchased from Sigma-Aldrich. Intracellular concentrations of metabolites were determined based on the assumption that in 1 mL of the culture at $OD_{600}$=200 the integrated volume of all cells is 50 μL.

This experiment was carried at pH 7.0 and temperature 34° C. A frozen vial of the *E. coli* strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L. The batched media had glucose batched in at 9.7 g/L. Induction was achieved by adding isopropyl-beta-D-1-thiogalactopyranoside (IPTG) at a final concentration of 200 uM when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum isoprene mass yield on glucose, a total of 48 to 72 hrs elapsed fermentation time.

Isoprene is volatile and can be efficiently swept from the tank by the inlet gas. The isoprene level in the bioreactor off-gas was determined using an iSCAN (Hamilton Sundstrand) mass spectrometer. The inlet gas was a custom blend of oxygen and nitrogen (~9.3 vol % and 90.7 vol % respectively). The citrate, glucose, acetate, and mevalonate concentrations in the fermentor broth were determined in broth samples taken at 4 hour intervals by an HPLC analysis. Concentration in broth samples were determined by comparison of the refractive index response versus a previously generated calibration curve using standard of a known concentration.

Results

TABLE 2

Isoprene Productivity Metrics

| Strain description/ Run Number | EFT (hrs) | Isoprene Titer (g/L) | Isoprene Volumetric Productivity (g/L/hr) | Peak cumulative mass yield of Isoprene on glucose (g/g) | CPI (g Isoprene/ gDCW) | Peak Specific Productivity (mg isoprene/ L/hr/OD) |
|---|---|---|---|---|---|---|
| CMP1043 Control strain | 44 | 74.41 | 1.69 | 14.26 | 1.64 | 26.87 (at 16 hrs EFT) |
| CMP1082 PyddV-ispA strain | 44 | 83.95 | 1.91 | 16.03 | 1.79 | 30.31 (at 12 hrs EFT) |

% wt Yield on glucose = Isoprene total (t)/[(Feed Wt(0) − Feed Wt(t) + 83.5) * 0.59)], where 0.59 is the wt % of glucose in the glucose feed solution and 83.5 is the grams of this feed batched into the fermentor at t = 0. Each feed had its weight % measured independently.
Isoprene Titer (g/L) = Integrated isoprene evolution rate (mol/L) * molecular weight of isoprene (g/mol)
CPI = total grams Isoprene/total grams dry cell weight
Specific productivity (mg/L/hr/OD) = HgER * 68.117 g/mol/OD.
HgER is the Isoprene Evolution Rate in (mmol/L/hr).
OD = optical density = Absorbance at 550 nm * dilution factor in water Conclusions The fermentation with the modified ispA promoter strain (CMP1082) had a higher isoprene yield on glucose than the control strain (CMP1043) which uses a wild type ispA promoter, see FIG. 9 and Table 2. The fermentation with the modified ispA promoter strain (CMP1082) had a higher isoprene titer (see FIG. 10 and Table 2), a higher cell productivity index (see FIG. 11 and Table 2), a higher isoprene volumetric productivity (see FIG. 12 and Table 2), and a higher peak isoprene specific productivity (in the 12 hr range; see FIG. 13 and Table 2) than the control strain (CMP1043) which uses a wild type ispA promoter.

Example 3

Large Scale Fermentation of CMP1059

A P1 lysate was made from strain MD08-97 and used to transduce CMP722. A colony was selected on LB+chloramphenicol 5 mg/L and named CMP1024. CMP1024 was checked by PCR and sequenced to demonstrate presence of the proteolytic tag. The chloramphenicol marker was looped out using pCP20 (Datsenko and Wanner, supra) and a chloramphenicol sensitive colony was selected and named CMP1034. Plasmids MCM82 and pCHL243 were electroporated concomitantly into CMP1034. A colony growing on LB+carbenicillin 50 mg/L and spectinomycin 50 mg/L was selected and named CMP105.

Fermentation runs were performed to test certain performance metrics (cumulative isoprene yield on glucose, isoprene productivity, peak specific productivity and cell productivity index) of strain CMP1059 (HMB GI1.2gltA, ispA_prot_tag, MCM82, pCHL243) to that of a control strain CMP1043 according to the following protocol:

Medium Recipe (per liter fermentation medium): K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (per liter): Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H$_3$BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (per liter): Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (per liter): MgSO4*7H2O 296 g, citric acid monohydrate 296 g, ferric ammonium citrate 49.6 g. All components were dissolved in water, q.s. to volume and filter sterilized with 0.22 micron filter.

Feed solution (per kilogram): Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

This experiment was carried at pH 7.0 and temperature 34° C. A frozen vial of the *E. coli* strain was thawed and inoculated into a flask with tryptone-yeast extract medium and the appropriate antibiotics. After the inoculum grew to optical density 1.0, measured at 550 nm (OD550), 500 mL was used to inoculate a 15-L bioreactor and bring the initial tank volume to 5 L. The batched media had glucose batched in at 9.7 g/L. Induction was achieved by adding isopropyl-beta-D-1-thiogalactopyranoside (IPTG) at a final concentration of 200 µM when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum isoprene mass yield on glucose, a total of 48 to 72 hrs elapsed fermentation time.

The isoprene level in the bioreactor off-gas was determined using an iSCAN (Hamilton Sundstrand) mass spectrometer. The inlet gas was a custom blend of oxygen and nitrogen (~9.3 vol % and 90.7 vol % respectively). The citrate, glucose, acetate, and mevalonate concentrations in the fermentor broth were determined in broth samples taken at 4 hour intervals by an HPLC analysis. Concentration in broth samples were determined by comparison of the refractive index response versus a previously generated calibration curve using standard of a known concentration Results The fermentation with the proteolytic tag on ispA strain (CMP1059) had an 11% higher cell productivity index over the control strain (CMP1043) which uses the wild type ispA protein. Additionally, the fermentation with the proteolytic tag on ispA strain (CMP1059) had a 14% higher peak isoprene specific productivity (at 16 hrs EFT) versus the control strain (at 16 hrs EFT, CMP1043) which uses the wild type ispA protein.

Example 4

Construction of Strain CMP1136 (−PGL)

A PCR product containing a Kanamycin cassette flanked by FRT sites and regions homologous to upstream and downstream of pgl (ybhE) was obtained, using the PCR method described in example 4, Keio strain JW0750 (Baba et al. 2006. Mol. Syst. Biol. 2:1-11) which contains a kanamycin cassette in the pgl locus, and primers pglAmpF (5'-cagcaaatagcaggtgtatccagc-3' (SEQ ID NO:11)) and pglAmpR (5'-GCA ACC GAC TGT TGA TAG AAC AAC-3' (SEQ ID NO:12)). This PCR product was used in a recombineering reaction (see protocol described above) with *E. coli* CMP1075 (supra). A colony was selected on LB+kanamycin 10 mg/L and named CMP1125. The kanamycin marker was removed using the protocol recommended by the manufacturer (Gene Bridges, Heidelberg, Germany) to form strain CMP1133.

CMP1133 was checked by PCR with primers pglAmpF (supra) and pglRecCheck (5'-GGT TAC AAA ATG ATT GGC GTA CGC-3' (SEQ ID NO:13)) to demonstrate deletion of the pgl gene. Plasmids MCM82 and pCHL243 were electroporated concomitantly into CMP1133. A colony growing on LB+carbenicilin 50 mg/L and spectinomycin 50 mg/L was selected and named CMP1136.

Example 5

Large Scale Fermentation of CMP1136

This experiment was performed to evaluate isoprene production from *E. coli*(BL21) expressing introduced genes from the mevalonate pathway and grown in fed-batch culture at the 15-L scale. An isoprene producing strain CMP1082 (HMB GI1.2gltA, PyddVIspA_GO, truncIspA, pMCM82, pDW72) was run in a standard isoprene production process, described below. The performance metrics (cumulative isoprene yield on glucose, instantaneous isoprene yield on glucose, volumetric productivity of isoprene, specific productivity and cell productivity index) are compared to an experimental strain CMP1136 (HMB GI1.2gltA, PyddVIspA_GO, truncIspA, pgl–, pMCM82, pDW72) that was run in the same conditions to see if any yield improvement can be attributed to the deletion of the pgl gene in CMP1136.

Medium Recipe (per liter fermentation medium): K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (per liter): Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (per liter): Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (per liter): MgOS4*7H2O 296 g, citric acid monohydrate 296 g, ferric ammonium citrate 49.6 g. All components were dissolved in water, q.s. to volume and filter sterilized with 0.22 micron filter.

Feed solution (per kilogram): Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

This experiment was carried out to monitor isoprene formation from glucose at the desired fermentation pH (7.0) and temperature (34° C.). A frozen vial of the *E. coli* strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L.

The batched media had glucose batched in at 9.7 g/L. Induction was achieved by adding isopropyl-beta-D-1-thiogalactopyranoside (IPTG). IPTG was added to the tank to bring the concentration to 200 uM when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum isoprene mass yield on glucose, a total of 68 to 72 hrs elapsed fermentation time.

Results

The pgl– strain (CMP1136) achieved a higher % yield of isoprene on glucose than the pgl+ strain (CMP1082). See Table 3 and FIG. 14. The pgl– strain (CMP1136) achieved a higher instantaneous % yield of isoprene on glucose than the pgl+ strain (CMP1082) and was able to maintain this high productivity for a longer period of time (~24 hrs at max for pgl– versus ~12 hrs at max for pgl+). See Table 3 and FIG. 15. The pgl– strain (CMP1136) achieved a higher cell productivity index than the pgl+ strain (CMP1082). At the end of fermentation 68 to 72 hrs, the pgl– strain had a much higher CPI. Also, at the time of maximum cumulative yield of isoprene on glucose (44 hrs for the pgl+ strain and 56 hrs for the pgl– strain) the CPI is higher in the pgl– strain. See Table 3 and FIG. 16. The pgl– strain (CMP1136) achieved about the same overall volumetric productivity as the pgl+ strain (CMP1082). See Table 3 and FIG. 17. The pgl– strain (CMP1136) achieved about the same peak specific productivity as the pgl+ strain (CMP1082). However, the pgl– strain (CMP1136) was able to maintain this high productivity for a longer period of time than the pgl+ strain (CMP1082) and was notably better late in the fermentation. See Table 3 and FIG. 18.

TABLE 3

| | | | Isoprene productivity metrics | | | |
|---|---|---|---|---|---|---|
| Strain description/ Run Number | Oxygen inlet Conc. (vol %) | Peak instantaneous % yield of isoprene on glucose (g/g %) | Overall Isoprene Volumetric Productivity (g/L/hr) at time of max overall isoprene yield | Max Overall % Yield of Isoprene on glucose (g/g) | CPI (g Isoprene/ gDCW) at time of max overall isoprene yield | Peak Specific Productivity (mg isoprene/ L/hr/OD) |
| CMP1082/ 20111110 | 9.3% | 20.1 | 1.91 | 16.3 | 1.81 | 30.31 |
| CMP1136/ 20111225 | 9.3% | 22.3 | 1.82 | 17.2 | 2.73 | 28.61 |

Example 6

Large Scale Fermentation of DW719

This experiment was to evaluate isoprene production from E. coli (BL21) expressing introduced genes from the mevalonate pathway and grown in fed-batch culture at the 15-L scale. Previously, isoprene producing strain CMP1043 (HMB GI1.2gltA pMCM82, pDW72) was observed to achieve different peak cumulative yields of isoprene depending on the concentration of oxygen in the inlet gas (5.0, 7.7, 9.3 and 20.9 vol %, in respective runs), with 5.0, 7.7 and 9.3 vol % oxygen achieving higher isoprene yields. In this example, the oxygen concentration was kept fixed (8.7 vol % oxygen), but the rate of inlet gas delivery to the tank was modified. Process conditions are summarized in the methods section below. The performance metrics (cumulative isoprene yield on glucose, instantaneous isoprene yield on glucose, volumetric isoprene productivity, specific productivity and cell productivity index) are compared to highlight any differences. The tested strain is described in Table 4.

TABLE 4

List of strains.

| Strain Name | Host/yddV promoter modification | upper plasmid | lower plasmid | | Run numbers |
|---|---|---|---|---|---|
| DW719 (Control) | BL21 t pgl, GI1.2gltA pgl-, yhfSFRTPy ddVIspAyhf S thiFRTtruncI spA | Ptrc-P. alba IspS (MEA variant)-mMVK, Carb50 ppm (pDW240) | E. gallinarum upper, Spec50 ppm (pMCM1225) | | 20120484 20120521 20120522 |

Methods

Medium Recipe (per liter fermentation medium): K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (per liter): Citric Acids*H2O 40 g, MnSO4*H2O 30 g, NaCl 10 g, FeSO4*7H2O 1 g, CoCl2*6H2O 1 g, ZnSO4*7H2O 1 g, CuOS4*5H2O 100 mg, $H_3BO_3$ 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (per liter): Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (per liter): MgOS4*7H2O 296 g, citric acid monohydrate 296 g, ferric ammonium citrate 49.6 g. All components were dissolved in water, q.s. to volume and filter sterilized with 0.22 micron filter.

Feed solution (per kilogram): Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution): Macro Salt Solution 5.54 mL, Vitamin Solution 6.55 mL, 1000× Modified Trace Metal Solution 0.82 mL, 10 mg/mL IPTG solution (1.86 mL).

This example was carried out to monitor isoprene production from glucose at the desired fermentation pH (7.0) and temperature (34° C.). To start, the appropriate frozen vial of the E. coli (BL21) strain was thawed and inoculated into a flask with tryptone-yeast extract (LB) medium and the appropriate antibiotics. After the inoculum grew to an optical density of approximately 1.0, measured at 550 nm ($OD_{550}$), 500 mL was used to inoculate a 15-L bioreactor and bring the initial tank volume to 5 L.

The inlet gas using to maintain bioreactor backpressure at 0.7 bar gauge and to provide the oxygen to the production organisms was supplied by in-house facilities that dilute the inlet gas to a known concentration (~9 vol % oxygen). The inlet rate varied by fermenter as follows:

Experiment number 20120484: inlet rate of 8.0 standard liter per minute;

Experiment number 20120522: inlet rate of 10.0 standard liter per minute;

Experiment number 20120521: inlet rate of 14.0 standard liter per minute.

The batched media had glucose batched in at 9.7 g/L. Induction was achieved by adding IPTG. A shot of IPTG was added to the tank to bring the concentration to a specified level when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum cumulative isoprene mass yield on glucose, a total of 56 to 64 hrs of elapsed fermentation time.

Oxygen, nitrogen, and carbon dioxide levels in the offgas were determined independently using the mass spectrometers iSCAN (Hamilton Sundstrand) and a Hiden HPR20 (Hiden Analytical) mass spectrometer.

Dissolved oxygen in the fermentation broth is measured by a sanitary, sterilizable probe with an optical sensor provided by Hamilton Company.

The citrate, glucose, acetate, and mevalonate concentrations in the fermentor broth were determined in broth samples taken at 4 hour intervals by HPLC analysis. Concentrations in broth samples were determined by comparison of the refractive index response versus a previously generated calibration curve using a standard of a known concentration.

HPLC Information

System: Waters Alliance 2695
Column: BioRad—Aminex HPX-87H Ion Exclusion Column, 300 mm×7.8 mm, Catalog #125-0140
Column Temperature: 50° C.
Guard column: BioRad—Microguard Cation H refill, 30 mm×4.6 mm, Catalog #125-0129
Running buffer: 0.01N $H_2SO_4$
Running buffer flow rate: 0.6 mL/min
Approximate running pressure: 1100-1200 psi
Injection volume: 20 μL
Detector: Refractive Index (Knauer K-2301)
Runtime: 26 minutes Results The isoprene productivity metrics are presented in Table 5 and FIGS. 19-23. This example provides that even with a fixed oxygen concentration in the gas inlet, an increased rate may be achieved by increasing the total flow of gas into the tank. Without being bound to any particular theory, it is believed that the increase in total flow of gas to the tank effectively increases the number of moles of oxygen delivered to the tank per unit time.

TABLE 5

Isoprene productivity metrics.

| Strain Name/ Run Number/ Inlet flow rate | Inlet Oxygen Conc. (vol %) | Max Overall % Yield of Isoprene on glucose (g/g %) | Peak instantaneous % yield of isoprene on glucose (g/g %) | Overall Isoprene Volumetric Productivity (g/L/hr) at time of max overall isoprene yield | Peak Oxygen Uptake Rate (mmol/L/hr) | CPI (g Isoprene/ gDCW) at time of max overall isoprene yield | Peak Specific Productivity (mg isoprene/ L/hr/OD) |
|---|---|---|---|---|---|---|---|
| DW719/ 20120521/ 14 slpm | 8.69 | 17.23 | 19.13 (+/−1.29) | 2.83 | 292 | 2.26 | 41.5 |
| DW719/ 20120522/ 10 slpm | 8.69 | 17.87 | 19.79 (+/−0.68) | 2.59 | 252 | 2.45 | 40.6 |
| DW719/ 20120484/ 8 slpm | 8.70 | 17.18 | 19.02 (+/−0.63) | 2.20 | 213 | 2.44 | 41.3 |

What is claimed is:

1. A method for producing isoprene comprising (a) culturing a microbial recombinant host cell comprising a heterologous nucleic acid encoding isoprene synthase under reduced oxygen inlet levels wherein the cell is in fermentation or production phase, wherein the reduced oxygen inlet levels comprise between about 4% to about 15% oxygen and wherein the host cell is a bacterial cell; and (b) producing isoprene.

2. The method of claim 1 further comprising recovering the isoprene.

3. The method of claim 1 wherein the reduced oxygen inlet level is between about 5% to about 15% oxygen.

4. The method of claim 3 wherein the reduced oxygen inlet level is between about 7% to about 10% oxygen.

5. The method of claim 4 wherein the reduced oxygen inlet level is about 7.7% oxygen.

6. The method of claim 4 wherein the reduced oxygen inlet level is about 9.3% oxygen.

7. The method of claim 1 wherein the isoprene synthase is a plant isoprene synthase.

8. The method of claim 7, wherein the plant isoprene synthase is a poplar isoprene synthase, a kudzu isoprene synthase, a willow isoprene synthase, or a eucalyptus isoprene synthase.

9. The method of claim 7 wherein the plant isoprene synthase is an isoprene synthase from *Pueraria* or *Populus* or a hybrid, *Populus alba×Populus tremula*.

10. The method of claim 7 wherein the plant isoprene synthase polypeptide is selected from the group consisting of *Pueraria montana* or *Pueraria lobata, Populus tremuloides, Populus alba, Populus nigra*, and *Populus trichocarpa*.

11. The method of claim 1 wherein the isoprene synthase is an isoprene synthase variant.

12. The method of claim 1 wherein the cell further comprises a heterologous nucleic acid encoding for one or more mevalonate (MVA) pathway polypeptide and/or one or more 1-deoxy-d-xylulose 5-phosphate (DXP) pathway polypeptide.

13. The method of claim 12, wherein the cell further comprises a heterologous nucleic acid encoding for one or more isopentenyl diphosphate isomerase (IDI) polypeptide.

14. The method of claim 12, wherein any one or more copies of a heterologous nucleic acid is overexpressed.

15. The method of claim 12, wherein the heterologous nucleic acid is cloned into a multicopy plasmid.

16. The method of claim 12, wherein the heterologous nucleic acid is placed under an inducible promoter or a constitutive promoter.

17. The method of claim 12, wherein any one or more of the heterologous nucleic acids is integrated into the chromosome of the recombinant host cell.

18. The method of claim 1, wherein the bacterial cells are gram-positive bacterial cells or gram-negative bacterial cells.

19. The method of claim 1, wherein the bacterial cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Corynebacterium* sp., *Pseudomonas* sp., and *P. alcaligenes* cells.

20. The method of claim 19, wherein the bacterial cells are *E. coli*.

21. A method for producing isoprene comprising (a) culturing a recombinant bacterial host cell comprising a heterologous nucleic acid encoding isoprene synthase under reduced oxygen inlet levels having an inlet airflow rate of between about 8.0 standard liter per minute (SLPM) and about 14 SLPM; and (b) producing isoprene.

22. The method of claim 21, further comprising recovering the isoprene.

23. The method of claim 21, wherein the inlet airflow rate is about 10.0 SLPM.

* * * * *

SEQUENCE LISTING

```
<160> NUMBER OF SEQ ID NOS: 13

<210> SEQ ID NO 1
<211> LENGTH: 329
<212> TYPE: PRT
<213> ORGANISM: Artificial Sequence
<220> FEATURE:
<223> OTHER INFORMATION: Synthetic Construct

<400> SEQUENCE: 1

Met Thr Asp Val Arg Phe Arg Ile Ile Gly Thr Gly Ala Tyr Val Pro
1               5                   10                  15

Glu Arg Ile Val Ser Asn Asp Glu Val Gly Ala Pro Ala Gly Val Asp
                20                  25                  30

Asp Asp Trp Ile Thr Arg Lys Thr Gly Ile Arg Gln Arg Arg Trp Ala
            35                  40                  45

Ala Asp Asp Gln Ala Thr Ser Asp Leu Ala Thr Ala Ala Gly Arg Ala
        50                  55                  60

Ala Leu Lys Ala Ala Gly Ile Thr Pro Glu Gln Leu Thr Val Ile Ala
65                  70                  75                  80

Val Ala Thr Ser Thr Pro Asp Arg Pro Gln Pro Pro Thr Ala Ala Tyr
                85                  90                  95

Val Gln His His Leu Gly Ala Thr Gly Thr Ala Ala Phe Asp Val Asn
                100                 105                 110

Ala Val Cys Ser Gly Thr Val Phe Ala Leu Ser Ser Val Ala Gly Thr
            115                 120                 125

Leu Val Tyr Arg Gly Gly Tyr Ala Leu Val Ile Gly Ala Asp Leu Tyr
        130                 135                 140

Ser Arg Ile Leu Asn Pro Ala Asp Arg Lys Thr Val Val Leu Phe Gly
145                 150                 155                 160

Asp Gly Ala Gly Ala Met Val Leu Gly Pro Thr Ser Thr Gly Thr Gly
                165                 170                 175

Pro Ile Val Arg Arg Val Ala Leu His Thr Phe Gly Gly Leu Thr Asp
```

```
                      180                 185                 190
Leu Ile Arg Val Pro Ala Gly Gly Ser Arg Gln Pro Leu Asp Thr Asp
                195                 200                 205

Gly Leu Asp Ala Gly Leu Gln Tyr Phe Ala Met Asp Gly Arg Glu Val
            210                 215                 220

Arg Arg Phe Val Thr Glu His Leu Pro Gln Leu Ile Lys Gly Phe Leu
225                 230                 235                 240

His Glu Ala Gly Val Asp Ala Asp Ile Ser His Phe Val Pro His
                245                 250                 255

Gln Ala Asn Gly Val Met Leu Asp Glu Val Phe Gly Glu Leu His Leu
            260                 265                 270

Pro Arg Ala Thr Met His Arg Thr Val Glu Thr Tyr Gly Asn Thr Gly
            275                 280                 285

Ala Ala Ser Ile Pro Ile Thr Met Asp Ala Ala Val Arg Ala Gly Ser
        290                 295                 300

Phe Arg Pro Gly Glu Leu Val Leu Leu Ala Gly Phe Gly Gly Met
305                 310                 315                 320

Ala Ala Ser Phe Ala Leu Ile Glu Trp
                325

<210> SEQ ID NO 2
<211> LENGTH: 2439
<212> TYPE: DNA
<213> ORGANISM: Listeria grayi DMS 20601

<400> SEQUENCE: 2
atggttaaag acattgtaat aattgatgcc ctccgtactc ccatcggtaa gtaccgcggt      60
cagctctcaa agatgacggc ggtggaattg ggaaccgcag ttacaaaggc tctgttcgag     120
aagaacgacc aggtcaaaga ccatgtagaa caagtcattt ttggcaacgt tttacaggca     180
gggaacggcc agaatcccgc ccgtcagatc gcccttaatt ctggcctgtc cgcagagata     240
ccggcttcga ctattaacca ggtgtgtggt tctggcctga agcaataag catggcgcgc      300 caacagatcc tactcggaga agcggaagta atagtagcag gaggtatcga atccatgacg     360
aatgcgccga gtattacata ttataataaa gaagaagaca ccctctcaaa gcctgttcct     420
acgatgacct tcgatggtct gaccgacgcg tttagcggaa agattatggg tttaacagcc     480
gaaaatgttg ccgaacagta cggcgtatca cgtgaggccc aggacgcctt tgcgtatgga     540
tcgcagatga agcagcaaa ggcccaagaa cagggcattt cgcagctga atactgcct        600 cttgaaatag gggacgaagt tattactcag gacgaggggg ttcgtcaaga gaccaccctc     660 gaaaattaa gtctgcttcg gaccatttt aaagaagatg gtactgttac agcgggcaac       720
gcctcaacga tcaatgatgg cgcctcagcc gtgatcattg catcaaagga gtttgctgag     780
acaaaccaga ttccctacct tgcgatcgta catgatatta cagagatagg cattgatcca     840
tcaataatgg gcattgctcc cgtgagtgcg atcaataaac tgatcgatcg taaccaaatt     900
agcatggaag aaatcgatct cttttgaaatt aatgaggcat ttgcagcatc ctcggtggta   960
gttcaaaaag agttaagcat tcccgatgaa aagatcaata ttggcggttc cggtattgca    1020
ctaggccatc tcttggcgc acaggagcg cgcattgtaa ccaccctagc gcaccagttg       1080
aaacgtacac acggacgcta tggtattgcc tccctgtgca ttggcggtgg ccttggccta    1140
gcaatattaa tagaagtgcc tcaggaagat cagccggtta aaaaatttta tcaattggcc    1200
cgtgaggacc gtctggctag acttcaggag caagccgtga tcagcccagc tacaaaacat    1260
```

```
gtactggcag aaatgacact tcctgaagat attgccgaca atctgatcga aaatcaaata   1320
tctgaaatgg aaatccctct tggtgtggct ttgaatctga gggtcaatga taagagttat   1380
accatcccac tagcaactga ggaaccgagt gtaatcgctg cctgtaataa tggtgcaaaa   1440
atggcaaacc acctgggcgg ttttcagtca gaattaaaag atggtttcct gcgtgggcaa   1500
attgtactta tgaacgtcaa agaacccgca actatcgagc atacgatcac ggcagagaaa   1560
gcggcaattt ttcgtgccgc agcgcagtca catccatcga ttgtgaaacg aggtgggggt   1620
ctaaaagaga tagtagtgcg tacgttcgat gatgatccga cgttcctgtc tattgatctg   1680
atagttgata ctaaagacgc aatgggcgct aacatcatta acaccattct cgagggtgta   1740
gccggctttc tgagggaaat ccttaccgaa gaaattctgt tctctatttt atctaattac   1800
gcaaccgaat caattgtgac cgccagctgt cgcataccttt acgaagcact gagtaaaaaa   1860
ggtgatggta acgaatcgc tgaaaaagtg gctgctgcat ctaaatttgc ccagttagat   1920
ccttatcgag ctgcaaccca caacaaaggt attatgaatg gtattgaggc cgtcgttttg   1980
gcctcaggaa atgacacacg ggcggtcgcg gcagccgcac atgcgtatgc ttcacgcgat   2040
cagcactatc ggggcttaag ccagtggcag gttgcagaag gcgcgttaca cggggagatc   2100
agtctaccac ttgcactcgg cagcgttggc ggtgcaattg aggtcttgcc taaagcgaag   2160
gcggcattcg aaatcatggg gatcacagag gcgaaggagc tggcagaagt cacagctgcg   2220
gtagggctgg cgcaaaacct ggcggcgtta agagcgcttg ttagtgaagg aatacagcaa   2280
ggtcacatgt cgctccaggc tcgctctctt gcattatcgg taggtgctac aggcaaggaa   2340
gttgaaatcc tggccgaaaa attacagggc tctcgtatga atcaggcgaa cgctcagacc   2400
atactcgcag agatcagatc gcaaaaagtt gaattgtga                          2439

<210> SEQ ID NO 3
<211> LENGTH: 1158
<212> TYPE: DNA
<213> ORGANISM: Enterococcus faecium mvaE

<400> SEQUENCE: 3
atgaccatga acgttggaat cgataaaatg tcattctttg ttccacctta ctttgtggac     60
atgactgatc tggcagtagc acgggatgtc gatcccaata agtttctgat tggtattggc    120
caggaccaga tggcagttaa tccgaaaacg caggatattg tgacatttgc cacaaatgct    180
gccaaaaaca tactgtcagc tgaggacctt gataaaattg atatggtcat agtcggcacc    240
gagagtggaa tcgatgaatc caaagcgagt gccgtagtgc ttcacaggtt gctcggtatc    300
cagaagtttg ctcgctcctt tgaaatcaaa gaagcctgtt atgggggtac cgcggcttta    360
cagttcgctg taaaccacat taggaatcat cctgaatcaa aggttcttgt agttgcatca    420
gatatcgcga atacggcct ggcttctgga ggtgaaccaa cgcaaggtgc aggcgctgtg    480
gctatgctcg tctcaactga ccctaagatc attgctttca cgacgatag cctcgcgctt    540 acacaagata tctatgactt ctggcgacca gttggacatg actatcctat ggtcgacggg    600
cctcttagta cagagaccta catccagtca tttcagaccg tatggcagga atacacaaaa    660
cggtcgcagc atgcactggc agactttgct gcccttagct ttcatatccc gtatactaaa    720
atgggcaaaa aggcgctgct tgcaatcctt gaaggcgaat cagaggaggc tcagaaccgt    780
atactagcaa aatatgaaaa gagtatagcc tactccagaa aggcgggtaa cctgtatacc    840
ggtagcctgt atctaggact tatttcactt ctggaaaatg cagaagacct taaagctggt    900
gatttaatag gcctcttttc ttacggttcc ggtgctgttg cggagttttt ctcaggaagg    960
```

```
ctggttgagg actatcagga acagctactt aaaacaaaac atgccgaaca gctggcccat    1020
agaaagcaac tgacaatcga ggagtacgaa acgatgttct ccgatcgctt ggacgtggac    1080
aaagacgccg aatacgaaga cacattagct tatagcattt cgtcagtccg aaacaccgta    1140
cgtgagtaca ggagttga                                                  1158

<210> SEQ ID NO 4
<211> LENGTH: 2442
<212> TYPE: DNA
<213> ORGANISM: Enterococcus gallinarum EG2 mvaE

<400> SEQUENCE: 4
atgaaagaag tggttatgat tgatgcggct cgcacaccca ttgggaaata cagaggtagt      60
cttagtcctt ttacagcggt ggagctgggg acactggtca cgaaagggct gctggataaa     120
acaaagctta agaaagacaa gatagaccaa gtgatattcg gcaatgtgct tcaggcagga     180
aacggacaaa acgttgcaag acaaatagcc ctgaacagtg gcttaccagt tgacgtgccg     240
gcgatgacta ttaacgaagt ttgcgggtcc ggaatgaaag cggtgatttt agcccgccag     300
ttaatacagt taggggaggc agagttggtc attgcagggg gtacggagtc aatgtcacaa     360
gcacccatgc tgaaacctta ccagtcagag accaacgaat acggagagcc gatatcatca     420
atggttaatg acgggctgac ggatgcgttt tccaatgctc acatgggtct tactgccgaa     480
aaggtggcga cccagttttc agtgtcgcgc gaggaacaag accggtacgc attgtccagc     540
caattgaaag cagcgcacgc ggttgaagcc ggggtgttct cagaagagat tattccggtt     600
aagattagcg acgaggatgt cttgagtgaa acgaggcag taagaggcaa cagcactttg     660
gaaaaactgg gcaccttgcg gacggtgttt tctgaagagg gcacggttac cgctggcaat     720
gcttccaccg tgaatgacgg cgctagtgtc gtgattcttg catcaaaaga atacgcggaa     780
aacaataatc tgccttacct ggcgacgata aaggaggttg cggaagttgg tatcgatcct     840
tctatcatgg gtattgcccc aataaaggcc attcaaaagt aacagatcg gtcgggcatg     900 aacctgtcca cgattgatct gttcgaaatt aatgaagcat cgcggcatc tagcattgtt     960 gtttctcaag agctgcaatt ggacgaagaa aaagtgaata tctatggcgg ggcgatagct    1020
ttaggccatc caatcggcgc aagcggagcc cggatactga caaccttagc atacggcctc    1080
ctgcgtgagc aaaagcgtta tggtattgcg tcattatgta tcggcggtgg tcttggtctg    1140
gccgtgctgt agaagctaa tatggagcag acccacaaag acgttcagaa gaaaaagttt    1200
taccagctta ccccctccga gcggagatcg cagcttatcg agaagaacgt tctgactcaa    1260
gaaacggcac ttattttcca ggagcagacg ttgtccgaag aactgtccga tcacatgatt    1320
gagaatcagg tctccgaagt ggaaattcca atgggaattg cacaaaattt tcagattaat    1380
ggcaagaaaa aatggattcc tatggcgact gaagaacctt cagtaatagc ggcagcatcg    1440
aacgcgccca aatctgcgg gaacatttgc gcggaaacgc ctcagcggct tatgcgcggg    1500
cagattgtcc tgtctggcaa atcagaatat caagccgtga taaatgccgt gaatcatcgc    1560
aaagaagaac tgattctttg cgcaaacgag tcgtacccga gtattgttaa acgcgggga    1620 ggtgttcagg atatttctac gcgggagttt atgggttctt ttcacgcgta tttatcaatc    1680
gactttctgg tggacgtcaa ggacgcaatg ggggcaaaca tgatcaactc tattctcgaa    1740
agcgttgcaa ataaactgcg tgaatggttc ccggaagagg aaatactgtt ctccatcctg    1800
tcaaacttcg ctacggagtc cctggcatct gcatgttgcg agattccttt tgaaagactt    1860
```

| | |
|---|---|
| ggtcgtaaca aagaaattgg tgaacagatc gccaagaaaa ttcaacaggc agggaatat | 1920 |
| gctaagcttg acccttaccg cgcggcaacc cataacaagg ggattatgaa cggtatcgaa | 1980 |
| gccgtcgttg ccgcaacggg aaacgacaca cgggctgttt ccgcttctat tcacgcatac | 2040 |
| gccgcccgta atggcttgta ccaaggttta acggattggc agatcaaggg cgataaactg | 2100 |
| gttggtaaat taacagtccc actggctgtg gcgactgtcg gtggcgcgtc gaacatatta | 2160 |
| ccaaaagcca aagcttccct cgccatgctg gatattgatt ccgcaaaaga actggcccaa | 2220 |
| gtgatcgccg cggtaggttt agcacagaat ctggcggcgt acgtgcatt agtgacagaa | 2280 |
| ggcattcaga aggacacat gggcttgcaa gcacgttctt tagcgatttc gataggtgcc | 2340 |
| atcggtgagg agatagagca agtcgcgaaa aaactgcgtg aagctgaaaa aatgaatcag | 2400 |
| caaacggcaa tacagatttt agaaaaaatt cgcgagaaat ga | 2442 |

<210> SEQ ID NO 5
<211> LENGTH: 1155
<212> TYPE: DNA
<213> ORGANISM: Enterococcus casseliflavus mvaE

<400> SEQUENCE: 5

| | |
|---|---|
| atgaaaatcg gtattgaccg tctgtccttc ttcatcccga atttgtattt ggacatgact | 60 |
| gagctggcag aatcacgcgg ggatgatcca gctaaatatc atattggaat cggacaagat | 120 |
| cagatggcag tgaatcgcgc aaacgaggac atcataacac tgggtgcaaa cgctgcgagt | 180 |
| aagatcgtga cagagaaaga ccgcgagttg attgatatgg taatcgttgg cacggaatca | 240 |
| ggaattgacc actccaaagc aagcgccgtg attattcacc atctccttaa aattcagtcg | 300 |
| ttcgcccgtt ctttcgaggt aaaagaagct tgctatggcg aactgctgc cctgcacatg | 360 |
| gcgaaggagt atgtcaaaaa tcatccggag cgtaaggtct tggtaattgc gtcagacatc | 420 |
| gcgcgttatg gtttggccag cggaggagaa gttactcaag gcgtgggggc cgtagccatg | 480 |
| atgattacac aaaaccccg gattctttcg attgaagacg atagtgtttt tctcacagag | 540 |
| gatatctatg atttctggcg gcctgattac tccgagttcc ctgtagtgga cgggccctt | 600 |
| tcaaactcaa cgtatataga gagttttcag aaagtttgga accggcacaa ggaattgtcc | 660 |
| ggaagagggc tggaagatta tcaagctatt gcttttcaca taccctatac gaagatgggt | 720 |
| aagaaagcgc tccagagtgt tttagaccaa accgatgaag ataaccagga gcgcttaatg | 780 |
| gctagatatg aggagtctat cgctatagc cggagaattg gtaacctgta cacaggcagc | 840 |
| ttgtaccttg tcttacaag cttgttggaa aactctaaaa gtttacaacc gggagatcgg | 900 |
| atcggcctct tttcctatgg cagtggtgcg gtgtccagt tctttaccgg gtatttagaa | 960 |
| gaaaattacc aagagtacct gttcgctcaa agccatcaag aaatgctgga tagccggact | 1020 |
| cggattacgg tcgatgaata cgagaccatc ttttcagaga ctctgccaga acatggtgaa | 1080 |
| tgcgccgaat atacgagcga cgtccccttt tctataacca agattgagaa cgacattcgt | 1140 |
| tattataaaa tctga | 1155 |

<210> SEQ ID NO 6
<211> LENGTH: 2448
<212> TYPE: DNA
<213> ORGANISM: Listeria grayi DSM 20601

<400> SEQUENCE: 6

| | |
|---|---|
| atggaagaag tggtaattat agatgcacgt cggactccga ttggtaaata tcacgggtcg | 60 |
| ttgaagaagt tttcagcggt ggcgctgggg acggccgtgg ctaaagacat gttcgaacgc | 120 |

```
aaccagaaaa tcaaagagga gatcgcgcag gtcataattg gtaatgtctt gcaggcagga      180
aatggccaga accccgcgcg gcaagttgct cttcaatcag ggttgtccgt tgacattccc      240
gcttctacaa ttaacgaggt ttgtgggtct ggtttgaaag ctatcttgat gggcatggaa      300
caaatccaac tcggcaaagc gcaagtagtg ctggcaggcg gcattgaatc aatgacaaat      360
gcgccaagcc tgtcccacta taacaaggcg gaggatacgt atagtgtccc agtgtcgagc      420
atgacactgg atggtctgac agacgcattt tctagtaaac ctatgggatt aacagcggaa      480
aacgtcgcac agcgctacgg tatctcccgt gaggcgcaag atcaattcgc atatcaatct      540
cagatgaaag cagcaaaagc gcaggcagaa aacaaattcg ctaaggaaat tgtgccactg      600
gcgggtgaaa ctaaaaccat cacagctgac gaagggatca gatcccaaac aacgatggag      660
aaactggcaa gtctcaaacc tgtttttaaa accgatggca ctgtaaccgc agggaatgct      720
agcaccatta atgacggggc cgcccttgtg ctgcttgcta gcaaaactta ctgcgaaact      780
aatgacatac cgtaccttgc gacaatcaaa gaaattgttg aagttggaat cgatccggag      840
attatgggca tctctccgat aaaagcgata caaacattgt acaaaatca aaaagttagc       900 ctcgaagata ttggagtttt tgaaataaat gaagcctttg ccgcaagtag catagtggtt      960
gaatctgagt tgggattaga tccggctaaa gttaaccgtt atgggggtgg tatatcctta     1020
ggtcatgcaa ttggggcaac cggcgctcgc ctggccactt cactggtgta tcaaatgcag     1080
gagatacaag cacgttatgg tattgcgagc ctgtgcgttg gtggtggact tggactggca     1140
atgcttttag aacgtccaac tattgagaag gctaaaccga cagacaaaaa gttctatgaa     1200
ttgtcaccag ctgaacggtt gcaagagctg gaaaatcaac agaaaatcag ttctgaaact     1260
aaacagcagt tatctcagat gatgcttgcc gaggacactg caaaccattt gatagaaaat     1320
caaatatcag agattgaact cccaatgggc gtcgggatga acctgaaggt tgatgggaaa     1380
gcctatgttg tgccaatggc gacggaagag ccgtccgtca tcgcggccat gtctaatggt     1440
gccaaaatgg ccggcgaaat tcacactcag tcgaaagaac ggctgctcag aggtcagatt     1500
gttttcagcg cgaagaatcc gaatgaaatc gaacagagaa tagctgagaa ccaagctttg     1560
attttcgaac gtgccgaaca gtcctatcct tccattgtga aaagagaggg aggtctccgc     1620
cgcattgcac ttcgtcattt tcctgccgat tctcagcagg agtctgcgga ccagtccaca     1680
tttttatcag tggaccttt tgtagatgtg aaagacgcga tggggcaaa tatcataaat       1740 gcaatacttg agggcgtcgc agccctgttt cgcgaatggt tccccaatga ggaaattctt     1800 tttttctattc tctcgaactt ggctacggag agcttagtca cggctgtttg tgaagtccca    1860
tttagtgcac ttagcaagag aggtggtgca acggtggccc agaaaattgt gcaggcgtcg     1920
ctcttcgcaa agacagaccc ataccgcgca gtgacccaca acaaagggat tatgaacggt     1980
gtagaggctg ttatgcttgc cacaggcaac gacacgcgcg cagtctcagc cgcttgtcat     2040
ggatacgcag cgcgcaccgg tagctatcag ggtctgacta actggacgat tgagtcggat     2100
cgcctggtag gcgagataac actgccgctg ccatcgcta cagttggagg cgctaccaaa      2160
gtgttgccca agctcaagc ggcactggag attagtgatg ttcactcttc tcaagagctt      2220
gcagccttag cggcgtcagt aggtttagta caaaatctcg cggccctgcg cgcactggtt     2280
tccgaaggta tacaaaaagg gcacatgtcc atgcaagccc ggtctctcgc aatcgcggtc     2340
ggtgctgaaa aagccgagat cgagcaggtc gccgaaaagt tgcggcagaa cccgccaatg     2400
aatcagcagc aggcgctccg ttttcttggc gagatccgcg aacaatga                  2448
```

<210> SEQ ID NO 7
<211> LENGTH: 1155
<212> TYPE: DNA
<213> ORGANISM: Enterococcus faecium mvaS

<400> SEQUENCE: 7

```
atgaacgtcg gcattgacaa aattaatttt tcgttccac cgtattatct ggatatggtc      60
gacctggccc acgcacgcga agtggacccg aacaaattta caattggaat tggacaggat     120
cagatggctg tgagcaaaaa gacgcacgat atcgtaacat tcgcggctag tgccgcgaag    180
gaaattttag aacctgagga cttgcaagct atagacatgg ttatagttgg taccgaatcg    240
ggcattgacg agagcaaagc atccgcggtc gttttacatc gtttgttggg cgtacaacct    300
ttcgctcgca gttttgaaat taaagaagcc tgttacgggg caaccgcagg cattcagttt     360
gccaagactc atatacaagc gaacccggag agcaaggtcc tggtaattgc aagcgatata    420
gctcggtatg tcttcggtc aggtggagag cccacacaag gcgcagggc agttgctatg      480 cttctcacgg caaatcccag aatcctgacc ttcgaaaacg acaatctgat gttaacgcag    540
gatatttatg acttctggag accacttggt cacgcttacc ctatggtaga tggccaccct    600
tccaatcaag tctatattga cagttttaag aaggtctggc aagcacattg cgaacgcaat    660
caagcttcta tatccgacta tgccgcgatt agttttcata ttccgtatac aaaaatgggt    720
aagaaagccc tgctcgctgt ttttgcagat gaagtggaaa ctgaacagga acgcgttatg    780
gcacggtatg aagagtctat cgtatattca cgccggatcg gcaacttgta tacgggatca    840
ttgtacctgg gctgatatc cttattggaa aacagttctc acctgtcggc gggcgaccgg    900
ataggattgt ttagttatgg gagtggcgct gtcagcgaat tttttctccgg tcgtttagtg    960 gcaggctatg aaaatcaatt gaacaaagag gcgcataccc agctcctgga tcagcgtcag    1020 aagcttttcca tcgaagagta tgaggcgatt tttacagatt ccttagaaat tgatcaggat    1080
gcagcgttct cggatgacct gccatattcc atccgcgaga taaaaacac gattcggtac     1140 tataaggaga gctga                                                     1155
```

<210> SEQ ID NO 8
<211> LENGTH: 2475
<212> TYPE: DNA
<213> ORGANISM: Enterococcus gallinarum EG2 mvaS

<400> SEQUENCE: 8

```
atggaagaag ttgtcatcat tgacgcactg cgtactccaa taggaaagta ccacggttcg      60
ctgaaagatt acacagctgt tgaactgggg acagtagcag caaggcgtt gctggcacga     120 aatcagcaag caaagaaaca catagcgcaa gttattattg caacgtcct gcaagccgga    180 agtgggcaga atccaggccg acaagtcagt ttacagtcag gattgtcttc tgatatccc     240 gctagcacga tcaatgaagt gtgtggctcg gtatgaaag cgattctgat gggtatggag    300
caaattcagc tgaacaaagc ctctgtggtc ttaacaggcg aattgaaag catgaccaac    360 gcgccgctgt ttagttatta caacaaggct gaggatcaat attcggcgcc ggttagcaca    420
atgatgcacg atggtctaac agatgctttc agttccaaac caatgggctt aaccgcagag    480
accgtcgctg agagatatgg aattacgcgt aaggaacaag atgaatttgc ttatcactct    540
caaatgaagg cggccaaagc ccaggcggcg aaaagtttg atcaggaaat tgtaccctg     600 acggaaaat ccggaacggt tctccaggac gaaggcatca gagccgcgac aacagtcgag    660
aagctagctg agcttaaaac ggtgttcaaa aaagacggaa cagttacagc gggtaacgcc    720
```

-continued

```
tctacgataa atgatggcgc tgctatggta ttaatagcat caaaatctta ttgcgaagaa        780
caccagattc cttatctggc cgttataaag gagatcgttg aggtgggttt tgcccccgaa        840
ataatgggta tttcccccat taaggctata gacaccctgc tgaaaaatca agcactgacc        900
atagaggata taggaatatt tgagattaat gaagcctttg ctgcgagttc gattgtggta        960
gaacgcgagt tgggcctgga ccccaaaaaa gttaatcgct atggcggtgg tatatcactc       1020
ggccacgcaa ttggggcgac gggagctcgc attgcgacga ccgttgctta tcagctgaaa       1080
gatacccagg agcgctacgg tatagcttcc ttatgcgttg gtggggtct tggattggcg        1140
atgcttctgg aaaacccatc ggccactgcc tcacaaacta attttgatga ggaatctgct       1200
tccgaaaaaa ctgagaagaa gaagttttat gcgctagctc ctaacgaacg cttagcgttt       1260
ttggaagccc aaggcgctat taccgctgct gaaaccctgg tcttccagga gatgacctta       1320
aacaaagaga cagccaatca cttaatcgaa aaccaaatca gcgaagttga aattccttta       1380
ggcgtgggcc tgaacttaca ggtgaatggg aaagcgtata atgttcctct ggccacggag       1440
gaaccgtccg ttatcgctgc gatgtcgaat ggcgccaaaa tggctggtcc tattacaaca       1500
acaagtcagg agaggctgtt acggggtcag attgtcttca tggacgtaca ggacccagaa       1560
gcaatattag cgaaagttga atccgagcaa gctaccattt tcgcggtggc aaatgaaaca       1620
tacccgtcta tcgtgaaaag aggaggaggt ctgcgtagag tcattggcag gaatttcagt       1680
ccggccgaaa gtgacttagc cacggcgtat gtatcaattg acctgatggt agatgttaag       1740
gatgcaatgg gtgctaatat catcaatagt atccctagaag gtgttgcgga attgtttaga       1800
aaatggttcc agaagaaga atcctgttc tcaattctct ccaatctcgc gacagaaagt        1860
ctggtaacgg cgacgtgctc agttccgttt gataaattgt ccaaaactgg gaatggtcga       1920
caagtagctg gtaaaatagt gcacgcgcg gactttgcta agatagatcc atacagagct        1980
gcccacacaca ataaaggtat tatgaatggc gttgaagcgt taatcttagc caccggtaat      2040
gacacccgtg cggtgtcggc tgcatgccac ggttacgcgg cacgcaatgg gcgaatgcaa       2100
gggcttacct cttggacgat tatcgaagat cggctgatag gctctatcac attacctttg       2160
gctattgcga cagtgggggg tgccacaaaa atcttgccaa aagcacaggc cgccctggcg       2220
ctaactggcg ttgagacggc gtcggaactg ccagcctgg cggcgagtgt gggattagtt        2280
caaaatttgg ccgctttacg agcactagtg agcgagggca ttcagcaagg gcacatgagt       2340
atgcaagcta gatccctggc cattagcgta ggtgcgaaag gtactgaaat agagcaacta       2400
gctgcgaagc tgagggcagc gacgcaaatg aatcaggagc aggctcgtaa atttctgacc       2460
gaaataagaa attaa                                                        2475
```

```
<210> SEQ ID NO 9
<211> LENGTH: 1161
<212> TYPE: DNA
<213> ORGANISM: Enterococcus casseliflavus mvaS

<400> SEQUENCE: 9
```

```
atgaacgttg gaattgataa aatcaatttt ttcgttccgc cctatttcat tgatatggtg        60
gatctcgctc atgcaagaga agttgacccc aacaagttca ctataggaat aggccaagat       120
cagatggcag taaacaagaa aacgcaagat atcgtaacgt tcgcgatgca cgccgcgaag       180
gatattctga ctaaggaaga tttacaggcc atagatatgg taatagtggg gactgagtct       240
gggatcgacg agagcaaggc aagtgctgtc gtattgcatc ggcttttagg tattcagcct       300
```

```
tttgcgcgct cctttgaaat taaggaggca tgctatgggg ccactgccgg ccttcagttt      360
gcaaaagctc atgtgcaggc taatccccag agcaaggtcc tggtggtagc ttccgatata      420
gcacgctacg gactggcatc cggaggagaa ccgactcaag gtgtaggtgc tgtggcaatg      480
ttgatttccg ctgatccagc tatcttgcag ttagaaaatg ataatctcat gttgacccaa      540
gatatatacg attttttggcg cccggtcggg catcaatatc ctatggtaga cggccatctg     600
tctaatgccg tctatataga cagctttaaa caagtctggc aagcacattg cgagaaaaac      660
caacggactg ctaaagatta tgctgcattg tcgttccata ttccgtacac gaaaatgggt      720
aagaaagctc tgttagcggt ttttgcggag gaagatgaga cagaacaaaa gcggttaatg      780
gcacgttatg aagaatcaat tgtatacagt cgtcggactg gaaatctgta tactggctca      840
ctctatctgg gcctgatttc cttactggag aatagtagca gtttacaggc gaacgatcgc      900
ataggtctgt ttagctatgg ttcaggggcc gttgcggaat ttttcagtgg cctcttggta      960
ccgggttacg agaaacaatt agcgcaagct gcccatcaag ctcttctgga cgaccggcaa     1020
aaactgacta tcgcagagta cgaagccatg tttaatgaaa ccattgatat tgatcaggac    1080
cagtcatttg aggatgactt actgtactcc atcagagaga tcaaaaacac tattcgctac    1140
tataacgagg agaatgaata a                                                1161
```

```
<210> SEQ ID NO 10
<211> LENGTH: 125
<212> TYPE: DNA
<213> ORGANISM: Enterobacteria phage lambda

<400> SEQUENCE: 10
aattcatata aaaacatac agataaccat ctgcggtgat aaattatctc tggcggtgtt       60
gacataaata ccactggcgg tgatactgag cacatcagca ggacgcactg accaccatga     120
aggtg                                                                  125

<210> SEQ ID NO 11
<211> LENGTH: 24
<212> TYPE: DNA
<213> ORGANISM: Artificial Sequence
<220> FEATURE:
<223> OTHER INFORMATION: Synthetic Construct

<400> SEQUENCE: 11
cagcaaatag caggtgtatc cagc                                              24

<210> SEQ ID NO 12
<211> LENGTH: 24
<212> TYPE: DNA
<213> ORGANISM: Artificial Sequence
<220> FEATURE:
<223> OTHER INFORMATION: Synthetic Construct

<400> SEQUENCE: 12
gcaaccgact gttgatagaa caac                                              24

<210> SEQ ID NO 13
<211> LENGTH: 24
<212> TYPE: DNA
<213> ORGANISM: Artificial Sequence
<220> FEATURE:
<223> OTHER INFORMATION: Synthetic Construct

<400> SEQUENCE: 13
ggttacaaaa tgattggcgt acgc                                              24
```